(12) United States Patent
Lee et al.

(10) Patent No.: US 11,447,500 B2
(45) Date of Patent: Sep. 20, 2022

(54) THIENOPYRIDINE DERIVATIVES AND PHARMACEUTICAL COMPOSITION COMPRISING SAME

(71) Applicant: WELLMARKER BIO CO., LTD., Seoul (KR)

(72) Inventors: Hyunho Lee, Yongin-si (KR); Chun-Ho Park, Yongin-si (KR); Sun Chul Hur, Hwaseong-si (KR); Jai-Hee Moon, Seoul (KR); Jae-Sik Shin, Seongnam-si (KR); Seung-Woo Hong, Seoul (KR); Yoon-Sun Park, Yongin-si (KR); Joseph Kim, Yongin-si (KR); Sohee Lee, Seoul (KR); Hyojin Kim, Seoul (KR); Hyebin Park, Seoul (KR)

(73) Assignee: WELLMARKER BIO CO., LTD., Seoul (KR)

( * ) Notice: Subject to any disclaimer, the term of this patent is extended or adjusted under 35 U.S.C. 154(b) by 141 days.

(21) Appl. No.: 16/638,668

(22) PCT Filed: Mar. 8, 2019

(86) PCT No.: PCT/KR2019/002743
§ 371 (c)(1),
(2) Date: Feb. 12, 2020

(87) PCT Pub. No.: WO2019/182274
PCT Pub. Date: Sep. 26, 2019

(65) Prior Publication Data
US 2021/0317133 A1    Oct. 14, 2021

(30) Foreign Application Priority Data
Mar. 8, 2018 (KR) .................. 10-2018-0027300

(51) Int. Cl.
*C07D 495/04* (2006.01)
*A61P 35/00* (2006.01)

(52) U.S. Cl.
CPC ............ *C07D 495/04* (2013.01); *A61P 35/00* (2018.01)

(58) Field of Classification Search
CPC ... C07D 495/04; A61P 35/00; A61K 31/4365; A61K 31/444; A61K 31/4436; A61K 31/503; A61K 31/519
See application file for complete search history.

(56) References Cited

U.S. PATENT DOCUMENTS

2007/0197537 A1   8/2007   Blake et al.

FOREIGN PATENT DOCUMENTS

| EP | 3 190 416 A1 | 7/2017 |
|---|---|---|
| KR | 10-1350006 B1 | 2/2014 |
| WO | 2009/026717 A1 | 3/2009 |
| WO | 2017/013160 A1 | 1/2017 |

OTHER PUBLICATIONS

Acute Leukemia, Merck Manual (Online Edition) 6 pages, pp. 1-6 (2013).*
Gura, Systems for identifying New Drugs Are Often Faulty, Cancer Models, Science, vol. 278, No. 5340, pp. 1041-1042, Nov. 1997.*
Hanks et al., The eukaryotic protein kinase superfamily: kinase (catalytic) domain structure and classification, Protein Kinases 6, The FASEB Journal, vol. 9, No. 8, pp. 576-596 (1995).*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1996.*
International Search Report dated Jun. 24, 2019 in International Application No. PCT/KR2019/002743.
Written Opinion of the International Searching Authority dated Jun. 24, 2019 in International Application No. PCT/KR2019/002743.
Donald P. Bottaro, et al.; "Identification of the Hepatocyte Growth Factor Receptor as the c-met Proto-Oncogene Product", Science, New Series, vol. 251, No. 4995. (Feb. 15, 1991), pp. 802-804 (Total 4 pages).
Yong-Qing Zhou, et al.; "Altered expression of the RON receptor tyrosine kinase in primary human colorectal adenocarcinomas: generation of different splicing RON variants and their oncogenic potential", Oncogene (2003) 22, pp. 186-197 (Total 12 pages).
Najme Faham & Alana L. Welm; "RON Signaling Is a Key Mediator of Tumor Progression in Many Human Cancers", Cold Spring Harbor Symposia on Quantitative Biology (2016), vol. LXXXI, pp. 177-188 (Total 12 pages).
Purnima Wagh, et al.; "The Met-Related Receptor Tyrosine Kinase Ron in Tumor Growth and Metastasis", Adv Cancer Res. (2008) 100, pp. Total 28 pages.
Ming-Hai Wang, et al., "Oncogenesis of RON receptor tyrosine kinase: a molecular target for malignant epithelial cancers", Acta Pharmacologica Sinica, Jun. 2006, vol. 27 No. 6, pp. 641-650 (Total 10 pages).

(Continued)

*Primary Examiner* — Deepak R Rao
(74) *Attorney, Agent, or Firm* — Sughrue Mion, PLLC

(57) ABSTRACT

A thienopyridine derivative compound represented by Formula 1 or pharmaceutically acceptable salts thereof have an excellent inhibitory effect on protein kinase activity, and accordingly, pharmaceutical compositions containing the thienopyridine compound can be usefully used for the prevention or treatment of a disease associated with the activity of a protein kinase.

15 Claims, 1 Drawing Sheet

(56) References Cited

OTHER PUBLICATIONS

E. Ramsay Camp, MD, et al., "RON, a Tyrosine Kinase Receptor Involved in Tumor Progression and Metastasis", Annals of Surgical Oncology, vol. 12 No. 4, Published Mar. 15, 2005, pp. 273-281 (Total 9 pages).

* cited by examiner

THIENOPYRIDINE DERIVATIVES AND PHARMACEUTICAL COMPOSITION COMPRISING SAME

TECHNICAL FIELD

The present invention relates to thienopyridine derivatives and a pharmaceutical composition comprising same. More specifically, the present invention pertains to novel thienopyridine derivatives which inhibit the activity of a protein kinase and, therefore, can be used for the prevention or treatment of diseases associated with the protein kinase activity, and a pharmaceutical composition comprising same.

BACKGROUND ART

Protein kinases are enzymes that phosphorylate other proteins to regulate the activity, location and function of the proteins, thereby controlling their various intracellular processes. Exemplary protein kinases include Ab1, ACK, ALK, Arg, ARK5, Aurora, Ax1, Bmx, BTK, CDK, CHK, c-Kit, c-MET, c-RAF, c-SRC, EGFR, FAK, Fes, FGFR, Flt3, GSK3, IGF, IKK, JAK, Lck, LIMK, Lyn, MEK, Mer, MK-2, P38alpha, PDGFR, PDK, Pim, PKA, PKB, PKCR, Plk-1/3, Ret, Ron, Ros, Rse, Tie, Trk, Tyro3, VEGFR, YES, and the like. Abnormalities in the control function of these protein kinases are closely related to the mechanisms of diseases such as cancers, immune diseases, neurological diseases, metabolic diseases and infections.

c-MET is a cell membrane receptor essential for embryonic development and wound healing. HGF (hepatocyte growth factor) is a ligand for the c-MET receptor and promotes the growth, angiogenesis, invasion and metastasis of tumors (Bottaro D P et al., *Science* 1991, 251 (4995): 802-804). Abnormal c-MET activation in cancer cells is closely related to aggravation of the prognosis of chemotherapy, and c-MET overexpression and mutation were observed in various cancer diseases such as non-small cell lung cancer. Because tumor invasion and metastasis are the leading cause of death in cancer patients, inhibiting c-MET signaling may be effective in cancer treatment.

On the other hand, RON (recepteur d'origine nantais) is a protein receptor belonging to the c-MET family, and is a receptor for macrophage-stimulating protein (MSP) secreted by the liver and regulating the action of macrophages (Zhou Y Q et al., *Oncogene* 2003, 22 (2): 186-197). It have been reported that the activity of RON has important functions in tumorigenesis and tumor progression and metastasis, and that overexpression or hyperactivity in colorectal cancer and breast cancer leads to tumor invasion and metastasis and inhibits apoptosis (Faham N. et. al., *Cold Spring Harb Symp Quant Biol.* 2016; Wagh P K et al., *Adv Cancer Res.* 2008; Wang M H et al., *Acta Pharmacologica Sinica.* 2006; Camp E R et al., *Ann Surg Oncol.* 2005).

Accordingly, a molecular-based anticancer agent and an antibody anticancer agent that inhibit the activity of RON kinase in various types of cancers including colorectal cancer have been demanded.

DISCLOSURE OF THE INVENTION

Technical Problem

The inventors of the present invention have been studying compounds that can be used as a protein kinase inhibitor, and have accomplished the present invention by confirming that thienopyridine derivatives having specific structures effectively inhibit the activity of a protein kinase and thus can be effectively used for the prevention or treatment of diseases associated therewith.

Accordingly, an object of the present invention is to provide novel thienopyridine derivatives which can inhibit the activity of a protein kinase and, therefore, can be usefully used in the treatment of diseases associated therewith, and a pharmaceutical composition comprising same

Solution to Problem

In order to achieve the above object, the present invention provides a thienopyridine derivative compound represented by Formula 1 or a pharmaceutically acceptable salt thereof.

The present invention also provides a pharmaceutical composition comprising the compound represented by Formula 1 or a pharmaceutically acceptable salt thereof, and a pharmaceutically acceptable additive.

The present invention also provides a use of the compound represented by Formula 1 or a pharmaceutically acceptable salt thereof for inhibiting the activity of a protein kinase; and a use thereof for the manufacture of a medicament therefor.

The present invention also provides a use of the compound represented by Formula 1 or a pharmaceutically acceptable salt thereof for preventing or treating a disease associated with the activity of a protein kinase; and a use thereof for the manufacture of a medicament therefor.

The present invention also provides a method of inhibiting the activity of a protein kinase, comprising administering the compound represented by Formula 1 or a pharmaceutically acceptable salt thereof to a subject in need thereof.

The present invention also provides a method of preventing or treating a disease associated with the activity of a protein kinase, comprising administering the compound represented by Formula 1 or a pharmaceutically acceptable salt thereof to a subject in need thereof.

Advantageous Effects of Invention

The thienopyridine derivative compounds represented by Formula 1 or pharmaceutically acceptable salts thereof have an excellent inhibitory effect on the activity of a protein kinase, and accordingly, pharmaceutical compositions comprising same are usefully used for the prevention or treatment of a disease associated with the activity of a protein kinase.

BEST MODE FOR CARRYING OUT THE INVENTION

Figure 1:
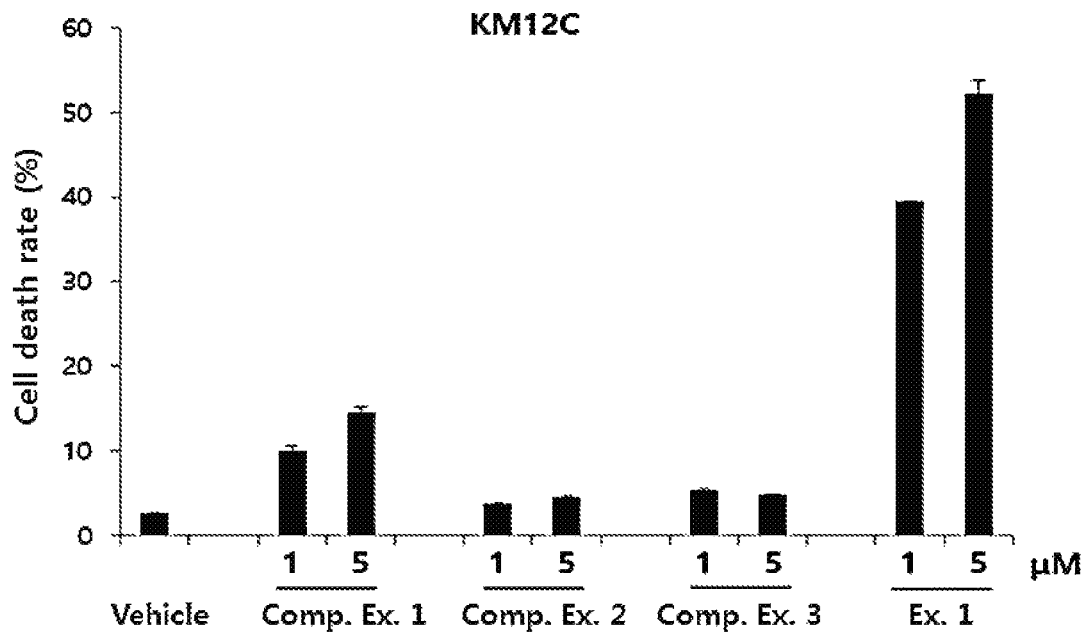
FIGS. 1 and 2 are graphs showing cell death rates (%) according to the concentrations (1 μM and 5 μM) of test compounds in the RON-activated (KM12C) and RON-mutated (HT29) colon cancer cell lines, respectively.

Hereinafter, the present invention will be described in detail.

The term "halogen" as used herein refers to F, Cl, Br, or I, unless otherwise stated.

The term "alkyl," unless otherwise specified, refers to a linear or branched saturated hydrocarbon radical. For example, "$C_{1-10}$ alkyl" means an alkyl having a skeleton consisting of 1 to 10 carbon atoms. Specifically, $C_{1-10}$ alkyl may include methyl, ethyl, n-propyl, i-propyl, n-butyl, i-butyl, t-butyl, n-pentyl, i-pentyl, t-pentyl, sec-pentyl, neopentyl, hexyl, heptyl, octyl, nonyl, decyl, and the like.

The term "haloalkyl" refers to an alkyl substituted with one or more halogen atoms. Specifically, haloalkyl may be an alkyl substituted with two or more halogen atoms of the same kind or substituted with two or more kinds of halogen atoms.

The term "heterocycle" refers to an aromatic or non-aromatic ring having one or more heteroatoms, which may be saturated or unsaturated and may be monocyclic or polycyclic. For example, "4- to 10-membered heterocycle" means a heterocycle comprising a total of 4 to 10 atoms constituting the skeleton, including heteroatom(s) and carbon atoms. Specifically, examples of the 4- to 10-membered heterocycle may include azetidine, diazetidine, pyrrolidine, pyrrole, imidazolidine, imidazole, pyrazolidine, pyrazole, oxazolidine, oxazole, isoxazolidine, isoxazole, thiazolidine, thiazole, isothiazolidine, isothiazole, piperidine, pyridine, piperazine, diazine, morpholine, thiomorpholine, azepane, diazepane, and the like.

The term "heteroatom" refers to an atom other than carbon (C), specifically nitrogen (N), oxygen (O), or sulfur (S) atom.

The term "substitution" refers to replacing a hydrogen atom in a molecular structure with a substituent, such that the valence on the designated atom is not exceeded, and such that a chemically stable compound results from the substitution. For example, "group A is substituted with substituent B" means that a hydrogen atom bonded to an atom such as a carbon atom constituting the skeleton of group A is replaced with substituent B, and group A and substituent B form a covalent bond.

The present invention provides a compound represented by the following Formula 1, or a pharmaceutically acceptable salt thereof:

[Formula 1]

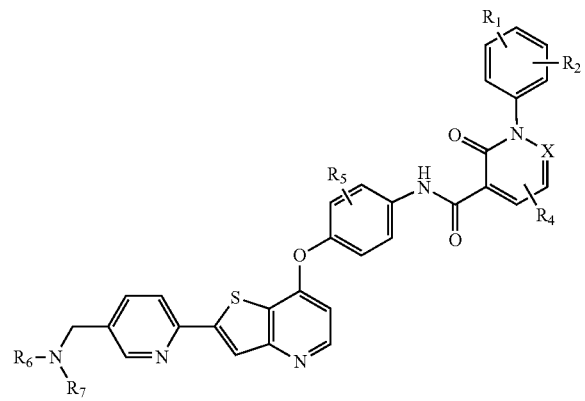

wherein $R_1$ and $R_2$ are each independently H, halogen, $C_{1-10}$ alkoxy, or halo $C_{1-10}$ alkyl;

X is —C(—$R_3$)= or —N=;

$R_3$ and $R_4$ are each independently H, halogen, $C_{1-10}$ alkyl, or $C_{1-10}$ alkoxy;

$R_5$ is H, halogen, or $C_{1-10}$ alkyl; and $R_6$ and $R_7$ are each independently H, $C_{1-10}$ alkyl, or —(CH$_2$)$_n$—Y—$R_8$, or $R_6$ and $R_7$, taken together with the N atom to which they are bonded, form a 4- to 10-membered heterocycle, wherein n is an integer of 0 to 10;

Y is —O—, —C(=O)—, —C(=O)—O—, —S—, or —S(=O)$_2$—;

$R_8$ is a linear or branched $C_{1-10}$ alkyl, wherein $R_8$ is unsubstituted or substituted with one or more substituents selected from the group consisting of halogen, amino, hydroxyl and $C_{1-6}$ alkoxy; and said heterocycle optionally further contain one or two heteroatoms selected from the group consisting of N, O, and S, in addition to the N atom to which $R_6$ and $R_7$ are bonded, and is unsubstituted or substituted with one or more substituents selected from halogen and $C_{1-6}$ alkyl.

In addition, the $C_{1-10}$ alkyl may include $C_{1-6}$ alkyl, $C_{1-3}$ alkyl, $C_{3-10}$ alkyl, $C_{3-6}$ alkyl, $C_{6-10}$ alkyl, and the like. In addition, the $C_{1-10}$ alkoxy may include $C_{1-6}$ alkoxy, $C_{1-3}$ alkoxy, $C_{3-10}$ alkoxy, $C_{3-6}$ alkoxy, $C_{6-10}$ alkoxy, and the like. In addition, the 4- to 10-membered heterocycle may include 4- to 7-membered heterocycle, 4- to 6-membered heterocycle, 5- to 7-membered heterocycle, 5- or 6-membered heterocycle, and the like.

According to one embodiment, in Formula 1, $R_1$ and $R_2$ are each independently H, halogen, methoxy, or —CF$_3$, wherein the halogen may be F, Cl, Br, or I.

According to another embodiment, in Formula 1, $R_3$ and $R_4$ are each independently H, halogen, methyl, methoxy, or ethoxy, wherein the halogen may be F, Cl, Br, or I.

According to a further embodiment, in Formula 1, X is —C(—$R_3$)=; and $R_3$ and $R_4$ are each independently H, halogen, methyl, methoxy, or ethoxy, but not simultaneously H.

According to a still further embodiment, in Formula 1, X is —N=; and $R_4$ is halogen, methyl, methoxy, or ethoxy, wherein the halogen may be F, Cl, Br, or I.

According to a still further embodiment, in Formula 1, $R_5$ is H or halogen, wherein the halogen may be F, Cl, Br, or I.

According to a still further embodiment, in Formula 1, $R_6$ and $R_7$ are each independently H, $C_{1-10}$ alkyl, or —(CH$_2$)$_n$—Y—$R_8$, but not simultaneously H.

According to a still further embodiment, in Formula 1, $R_6$ and $R_7$ are each independently H, $C_{1-6}$ alkyl, —$C_{1-6}$ alkylene-O—$C_{1-10}$ alkyl, or —C(=O)—O—$C_{1-10}$ alkyl, but not simultaneously H. Further, the $C_{1-6}$ alkylene may be —CH$_2$—, —C$_2$H$_4$—, —C$_3$H$_6$—, —C$_4$H$_8$—, —C$_5$H$_{10}$—, —C$_6$H$_{12}$—, and the like. In addition, the $C_{1-10}$ alkyl may be methyl, ethyl, n-propyl, i-propyl, n-butyl, i-butyl, t-butyl, n-pentyl, i-pentyl, t-pentyl, sec-pentyl, neopentyl, hexyl, heptyl, octyl, nonyl, decyl, and the like.

According to a still further embodiment, in Formula 1, $R_6$ and $R_7$, taken together with the N atom to which they are bonded, form

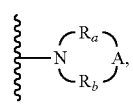

wherein $R_a$ and $R_b$ are each independently $C_{1-3}$ alkylene, A is —N(—$R_9$)— or —O—, and $R_9$ is $C_{1-6}$ alkyl. As specific examples, $R_6$ and $R_7$, together with the N atom to which they are bonded, may form a heterocycle group such as azetidinyl, diazetidinyl, pyrrolidinyl, pyrrolyl, imidazolidinyl, imidazolyl, pyrazolidinyl, pyrazolyl, oxazolidinyl, oxazolyl, isoxazolidinyl, isoxazolyl, thiazolidinyl, thiazolyl, isothiazolidinyl, isothiazolyl, piperidinyl, pyridinyl, piperazinyl, diazinyl, morpholino, thiomorpholino, azepanyl, and diazepanyl, which is optionally substituted with $C_{1-6}$ alkyl. Further, $R_a$ and $R_b$ may each independently be —$CH_2$—, —$C_2H_4$—, or —$C_3H_6$—. In addition, $R_9$ may be methyl, ethyl, n-propyl, i-propyl, n-butyl, i-butyl, t-butyl, n-pentyl, i-pentyl, t-pentyl, sec-pentyl, neopentyl, hexyl, and the like.

According to a still further embodiment, in Formula 1, $R_1$ and $R_2$ are each independently H, halogen, methoxy, or —$CF_3$; $R_3$ and $R_4$ are each independently H, halogen, methyl, methoxy, or ethoxy; $R_5$ is H or halogen; and $R_6$ is —$C_2H_4O$—$CH_3$ and $R_7$ is H, methyl, or t-butoxycarbonyl, or $R_6$ and $R_7$ are bonded together to form a morpholino or methylpiperazinyl group. Said halogen may be F, Cl, Br, or I.

According to one embodiment, the compound of Formula 1 may be represented by Formula 1a below.

[Formula 1a]

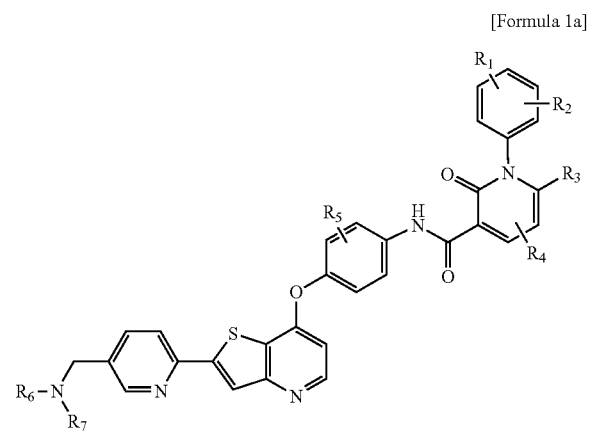

wherein $R_1$ to $R_7$ are the same as defined in the above Formula 1.

Specifically, in the above Formula 1a, $R_1$ and $R_2$ may each independently be H, halogen, or —$CF_3$. Further, $R_3$ and $R_4$ may each independently be H, halogen, methyl, methoxy, or ethoxy, but are not simultaneously H. In addition, $R_5$ may be H or halogen. $R_6$ may be —$C_{1-6}$ alkylene-O—$C_{1-10}$ alky, and $R_7$ may be H, $C_{1-6}$ alky, or —$C(=O)$—O—$C_{1-10}$ alkyl.

More specifically, in the above Formula 1a, $R_1$ and $R_2$ may each independently be H, halogen, or —$CF_3$; $R_3$ and $R_4$ may each independently be H, halogen, methyl, methoxy, or ethoxy; $R_5$ may be H or halogen; $R_6$ may be —$C_2H_4O$—$CH_3$; and $R_7$ may be H, methyl, or t-butoxycarbonyl.

According to another embodiment, the compound of Formula 1 may be represented by Formula 1b below.

[Formula 1b]

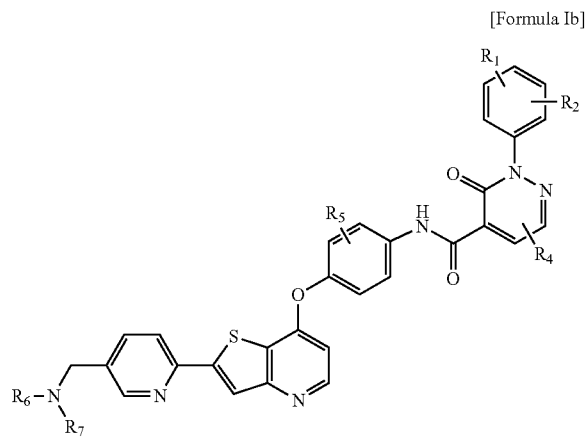

wherein $R_1$ to $R_7$ are the same as defined in the above Formula 1.

Specifically, in the above Formula 1b, $R_1$ and $R_2$ may each independently be H, halogen, or —$CF_3$. Further, $R_4$ may be halogen, methyl, methoxy, or ethoxy. In addition, $R_5$ may be H or halogen. $R_6$ may be —$C_{1-6}$ alkylene-O—$C_{1-10}$ alky, and $R_7$ may be H, $C_{1-6}$ alky, or —$C(=O)$—O—$C_{1-10}$ alkyl.

More specifically, in the above Formula 1b, $R_1$ and $R_2$ may each independently be H, halogen, or —$CF_3$; $R_4$ may be halogen, methyl, methoxy, or ethoxy; $R_5$ may be H or halogen; $R_6$ may be —$C_2H_4O$—$CH_3$; and $R_7$ may be H, methyl, or t-butoxycarbonyl.

According to a further embodiment, the compound of Formula 1 may be represented by Formula 1c below.

[Formula 1c]

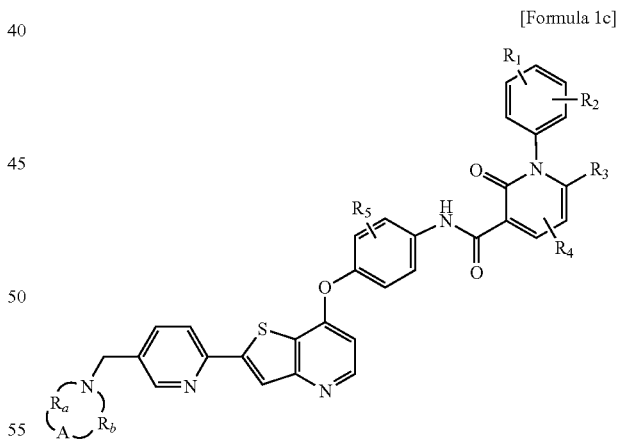

wherein $R_1$ to $R_5$ are the same as defined in the above Formula 1; $R_a$ and $R_b$ may each independently be $C_{1-3}$ alkylene; A may be —N(—$R_9$)—, or —O—; and $R_9$ may be $C_{1-6}$ alkyl.

Specifically, in the above Formula 1c, $R_1$ and $R_2$ may each independently be H, halogen, or —$CF_3$. Further, $R_3$ and $R_4$ may each independently be H, halogen, methyl, methoxy, or ethoxy, but are not simultaneously H. In addition, $R_5$ may be H or halogen. Further, $R_a$ and $R_b$ may be bonded together to form a morpholino or methylpiperazinyl group.

According to a still further embodiment, the compound of Formula 1 may be represented by Formula 1d below.

[Formula 1d]

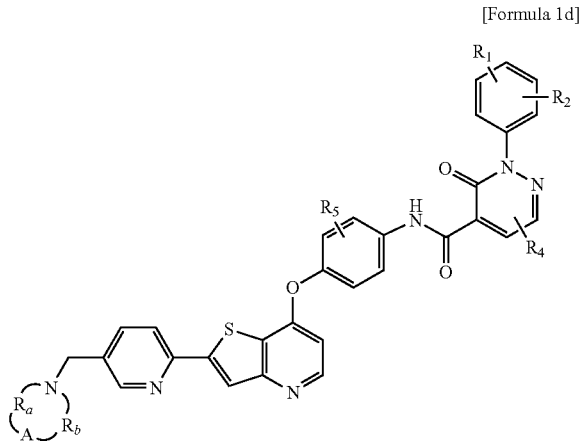

wherein $R_1$ to $R_5$ are the same as defined in the above Formula 1; $R_a$ and $R_b$ may each independently be $C_{1-3}$ alkylene; A may be —N(—$R_9$)— or —O—; and $R_9$ may be $C_{1-6}$ alkyl.

Specifically, in the above Formula 1d, $R_1$ and $R_2$ may each independently be H, halogen, or —$CF_3$. Further, $R_4$ may be halogen, methyl, methoxy, or ethoxy. In addition, $R_5$ may be H or halogen. Further, $R_a$ and $R_b$ may be bonded together to form a morpholino or methylpiperazinyl group.

The present invention includes pharmaceutically acceptable salts of the compounds of Formula 1.

The pharmaceutically acceptable salts should have low toxicity to humans and should not have any adverse effects on the biological activity and physicochemical properties of the parent compound.

For example, the pharmaceutically acceptable salt may be an acid addition salt formed by a pharmaceutically acceptable free acid.

As the free acid, inorganic acids or organic acids may be used. The inorganic acid may be hydrochloric acid, sulfuric acid, nitric acid, phosphoric acid, perchloric acid, bromic acid, and the like. The organic acid may be acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, and the like.

The acid addition salt may be obtained by a conventional method, for example, by dissolving the compound of Formula 1 in an excess amount of an acidic aqueous solution and precipitating the salt using a water-miscible organic solvent such as methanol, ethanol, acetone, or acetonitrile.

In addition, the pharmaceutically acceptable salt may be an alkali metal salt (e.g., sodium salt) or an alkaline earth metal salt (e.g., potassium salt).

The alkali metal salt or alkaline earth metal salt may be obtained, for example, by dissolving the compound of Formula 1 in an excess amount of alkali metal hydroxide or alkaline earth metal hydroxide solution, filtering off the undissolved compound salt, and evaporating and drying the filtrate.

Further, the compounds of the present invention may have a chiral carbon center and thus may exist in the form of R or S isomers, racemic compounds, individual enantiomers or mixtures thereof, individual diastereomers or mixtures thereof. All such stereoisomers and mixtures thereof may fall within the scope of the present invention.

In addition, the compounds of the present invention may include hydrates and solvates of the compound of Formula 1. The hydrates and solvates may be prepared using known methods and are preferably non-toxic and water-soluble. Particularly, the hydrates and the solvates may preferably be combined with one to five molecules of water and an alcoholic solvent (particularly, ethanol, etc.), respectively.

Specific examples of the compound of Formula 1 are listed below:

1) 4-Ethoxy-N-(3-fluoro-4-{[2-(5-{[(2-methoxyethyl) amino]methyl}pyridin-2-yl)thieno[3,2-b]pyridin-7-yl] oxy}phenyl)-2-oxo-1-phenyl-1,2-dihydropyridine-3-carboxamide;

2) N-(3-fluoro-4-{[2-(5-{[(2-methoxyethyl)amino] methyl}pyridin-2-yl)thieno[3,2-b]pyridin-7-yl] oxy}phenyl)-1-(4-fluorophenyl)-4-methoxy-2-oxo-1,2-dihydropyridine-3-carboxamide;

3) N-(3-fluoro-4-{[2-(5-{[(2-methoxyethyl)amino] methyl}pyridin-2-yl)thieno[3,2-b]pyridin-7-yl] oxy}phenyl)-4-methoxy-2-oxo-1-phenyl-1,2-dihydropyridine-3-carboxamide;

4) N-(3-fluoro-4-{[2-(5-{[(2-methoxyethyl)amino] methyl}pyridin-2-yl)thieno[3,2-b]pyridin-7-yl] oxy}phenyl)-1-(4-fluorophenyl)-2-oxo-1,2-dihydropyridine-3-carboxamide;

5) N-(3-fluoro-4-{[2-(5-{[(2-methoxyethyl)amino] methyl}pyridin-2-yl)thieno[3,2-b]pyridin-7-yl] oxy}phenyl)-2-oxo-1-phenyl-1,2-dihydropyridine-3-carboxamide;

6) t-Butyl {[6-(7-{4-[4-ethoxy-1-(4-fluorophenyl)-2-oxo-1, 2-dihydropyridine-3-carboxamido]-2-fluorophenoxy}thieno[3,2-b]pyridin-2-yl)pyridin-3-yl] methyl}(2-methoxyethyl)carbamate;

7) 4-ethoxy-N-(3-fluoro-4-{[2-(5-{[(2-methoxyethyl) amino]methyl}pyridin-2-yl)thieno[3,2-b]pyridin-7-yl] oxy}phenyl)-1-(4-fluorophenyl)-2-oxo-1,2-dihydropyridine-3-carboxamide;

8) 1-(4-chlorophenyl)-N-(3-fluoro-4-{[2-(5-{[(2-methoxyethyl)amino]methyl}pyridin-2-yl)thieno[3,2-b] pyridin-7-yl]oxy}phenyl)-2-oxo-1,2-dihydropyridine-3-carboxamide;

9) N-(3-chloro-4-{[2-(5-{[(2-methoxyethyl)amino] methyl}pyridin-2-yl)thieno[3,2-b]pyridin-7-yl] oxy}phenyl)-1-(4-fluorophenyl)-4-methoxy-2-oxo-1,2-dihydropyridine-3-carboxamide;

10) N-(2-chloro-4-{[-2-(5-{[(2-methoxyethyl)amino] methyl}pyridin-2-yl)thieno[3,2-b]pyridin-7-yl] oxy}phenyl)-1-(4-fluorophenyl)-4-methoxy-2-oxo-1,2-dihydropyridine-3-carboxamide;

11) 1-(4-fluorophenyl)-4-methoxy-N-(4-{[2-(5-{[(2-methoxyethyl)amino]methyl}pyridin-2-yl)thieno[3,2-b] pyridin-7-yl]oxy)phenyl)-2-oxo-1,2-dihydropyridine-3-carboxamide;

12) 4-ethoxy-N-(3-fluoro-4-{[2-(5-{[(2-methoxyethyl) amino]methyl}pyridin-2-yl)thieno[3,2-b]pyridin-7-yl] oxy}phenyl)-2-oxo-1-(4-(trifluoromethyl)phenyl)-1,2-dihydropyridine-3-carboxamide;

13) 1-(4-chlorophenyl)-N-(3-fluoro-4-{[2-(5-{[(2-methoxyethyl)amino]methyl}pyridin-2-yl)thieno[3,2-b]pyridin-7-yl]oxy}phenyl)-4-methoxy-2-oxo-1,2-dihydropyridine-3-carboxamide;

14) 4-ethoxy-N-(3-fluoro-4-{[2-(5-{[(2-methoxyethyl) amino]methyl}pyridin-2-yl)thieno[3,2-b]pyridin-7-yl] oxy}phenyl)-1-(3-fluorophenyl)-2-oxo-1,2-dihydropyridine-3-carboxamide;

15) 4-ethoxy-N-(3-fluoro-4-{[2-(5-{[(2-methoxyethyl) amino]methyl}pyridin-2-yl)thieno[3,2-b]pyridin-7-yl] oxy}phenyl)-1-(4-methoxyphenyl)-2-oxo-1,2-dihydropyridine-3-carboxamide;

16) 4-ethoxy-N-(3-fluoro-4-{[2-(5-{[(2-methoxyethyl) amino]methyl}pyridin-2-yl)thieno[3,2-b]pyridin-7-yl] oxy}phenyl)-1-(3-methoxyphenyl)-2-oxo-1,2-dihydropyridine-3-carboxamide;

17) N-(3-fluoro-4-{[2-(5-{[(2-methoxyethyl)amino] methyl}pyridin-2-yl)thieno[3,2-b]pyridin-7-yl] oxy}phenyl)-2-(4-fluorophenyl)-5-methyl-3-oxo-2,3-dihydropyridazine-4-carboxamide;

18) N-(3-fluoro-4-{[2-(5-{[(2-methoxyethyl)amino] methyl}pyridin-2-yl)thieno[3,2-b]pyridin-7-yl] oxy}phenyl)-5-methyl-3-oxo-2-phenyl-2,3-dihydropyridazine-4-carboxamide;

19) N-(3-fluoro-4-{[2-(5-{[(2-methoxyethyl)amino] methyl}pyridin-2-yl)thieno[3,2-b]pyridin-7-yl] oxy}phenyl)-3-oxo-2-phenyl-2,3-dihydropyridazine-4-carboxamide;

20) N-(3-fluoro-4-[{2-(5-[((2-methoxyethyl)amino}methyl] pyridin-2-yl)thieno[3,2-b]pyridin-7-yl}oxy]phenyl)-2-(4-fluorophenyl)-3-oxo-2,3-dihydropyridazine-4-carboxamide;

21) N-(3-fluoro-4-{[2-(5-{[(2-methoxyethyl)amino] methyl}pyridin-2-yl)thieno[3,2-b]pyridin-7-yl] oxy}phenyl)-6-methyl-2-oxo-1-phenyl-1,2-dihydropyridine-3-carboxamide;

22) N-(3-fluoro-4-{[2-(5-{[(2-methoxyethyl)amino] methyl}pyridin-2-yl)thieno[3,2-b]pyridin-7-yl] oxy}phenyl)-1-(4-fluorophenyl)-6-methyl-2-oxo-1,2-dihydropyridine-3-carboxamide;

23) 5-Bromo-N-(3-fluoro-4-{[2-(5-{[(2-methoxyethyl) amino]methyl}pyridin-2-yl)thieno[3,2-b]pyridin-7-yl] oxy}phenyl)-1-(4-fluorophenyl)-2-oxo-1,2-dihydropyridine-3-carboxamide;

24) 5-Chloro-N-(3-fluoro-4-{[2-(5-{[(2-methoxyethyl) amino]methyl}pyridin-2-yl)thieno[3,2-b]pyridin-7-yl] oxy}phenyl)-1-(4-fluorophenyl)-2-oxo-1,2-dihydropyridine-3-carboxamide;

25) N-(3-fluoro-4-{[2-(5-{[(2-methoxyethyl)amino] methyl}pyridin-2-yl)thieno[3,2-b]pyridin-7-yl] oxy}phenyl)-1-(4-fluorophenyl)-4-methyl-2-oxo-1,2-dihydropyridine-3-carboxamide;

26) N-(2-chloro-4-{[2-(5-{[(2-methoxyethyl)amino] methyl}pyridin-2-yl)thieno[3,2-b]pyridin-7-yl] oxy}phenyl)-4-ethoxy-1-(4-fluorophenyl)-2-oxo-1,2-dihydropyridine-3-carboxamide;

27) N-(3-fluoro-4-([2-(5-{[(2-methoxyethyl)amino)methyl] pyridin-2-yl}thieno[3,2-b]pyridin-7-yl)oxy]phenyl}-1-(4-fluorophenyl)-5,6-dimethyl-2-oxo-1,2-dihydropyridine-3-carboxamide;

28) N-(3-fluoro-4-{[-2-(5-{[(2-methoxyethyl)amino] methyl}pyridin-2-yl)thieno[3,2-b]pyridin-7-yl] oxy}phenyl)-4-methyl-2-oxo-1-phenyl-1,2-dihydropyridine-3-carboxamide;

29) N-(3-fluoro-4-{[-2-(5-{[(2-methoxyethyl)amino] methyl}pyridin-2-yl)thieno[3,2-b]pyridin-7-yl] oxy}phenyl)-1-(4-fluorophenyl)-5-methyl-2-oxo-1,2-dihydropyridine-3-carboxamide;

30) 4-Ethoxy-N-(3-fluoro-4-{[2-(5-{[(2-methoxyethyl) (methyl)amino]methyl}pyridin-2-yl)thieno[3,2-b]pyridin-7-yl]oxy}phenyl)-1-(4-fluorophenyl)-2-oxo-1,2-dihydropyridine-3-carboxamide;

31) 4-ethoxy-N-[3-fluoro-4-({2-[5-(morpholinomethyl) pyridin-2-yl]thieno[3,2-b]pyridin-7-yl}oxy)phenyl]-1-(4-fluorophenyl)-2-oxo-1,2-dihydropyridine-3-carboxamide;

32) 4-ethoxy-N-[3-fluoro-4-({2-[5-(morpholinomethyl) pyridin-2-yl]thieno[3,2-b]pyridin-7-yl}oxy)phenyl]-2-oxo-1-phenyl-1,2-dihydropyridine-3-carboxamide;

33) 4-ethoxy-N-{3-fluoro-4-[(2-{5-[(4-methylpiperazin-1-yl)methyl]pyridin-2-yl}thieno[3,2-b]pyridin-7-yl)oxy] phenyl}-1-(4-fluorophenyl)-2-oxo-1,2-dihydropyridine-3-carboxamide;

34) 4-ethoxy-N-{3-fluoro-4-[(2-{5-[(-methylpiperazin-1-yl) methyl]pyridin-2-yl}thieno[3,2-b]pyridin-7-yl)oxy]phenyl}-2-oxo-1-phenyl-1,2-dihydropyridine-3-carboxamide;

35) 1-(4-chlorophenyl)-4-ethoxy-N-[3-fluoro-4-({2-[5-(morpholinomethyl)pyridin-2-yl]thieno[3,2-b]pyridin-7-yl}oxy)phenyl]-2-oxo-1,2-dihydropyridine-3-carboxamide;

36) N-[3-chloro-4-({2-[5-(morpholinomethyl)pyridin-2-yl] thieno[3,2-b]pyridin-7-yl)oxy)phenyl]-4-ethoxy-1-(4-fluorophenyl)-2-oxo-1,2-dihydropyridine-3-carboxamide; and 37) N-[2-chloro-4-({2-[5-(morpholinomethyl)pyridin-2-yl] thieno[3,2-b]pyridin-7-yl}oxy)phenyl]-4-ethoxy-1-(4-fluorophenyl)-2-oxo-1,2-dihydropyridine-3-carboxamide.

The present invention also provides processes for preparing the compounds of Formula 1.

Preferably, the compounds of Formula 1 may be prepared by the methods shown in the following reaction schemes, but the preparation methods are not limited thereto. In particular, those skilled in the art will fully appreciate that the compounds of Formula 1 of the present invention can be prepared by a variety of methods using the techniques well known in the art.

Reaction Schemes 1 and 2 below illustrate by steps the process for preparing representative compounds according to the present invention. Several compounds of the present invention may be prepared by changing the reagents and solvents used in the following preparation steps or changing the reaction sequence. In addition, some compounds of the examples of the present invention were prepared according to a procedure not included in the scope of the following reaction schemes, and the preparation procedures for these compounds are described in detail in the respective examples.

According to one embodiment, a compound of Formula 1 may be prepared according to the procedure of Reaction Scheme 1 below.

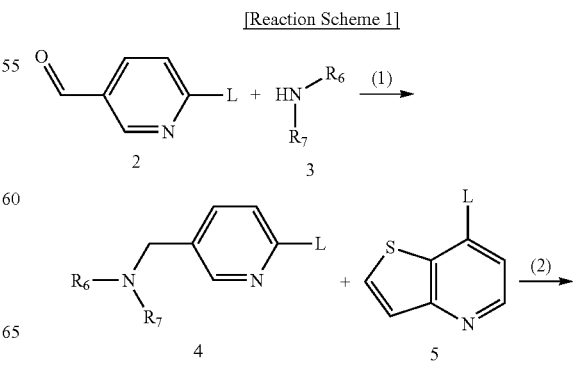

[Reaction Scheme 1]

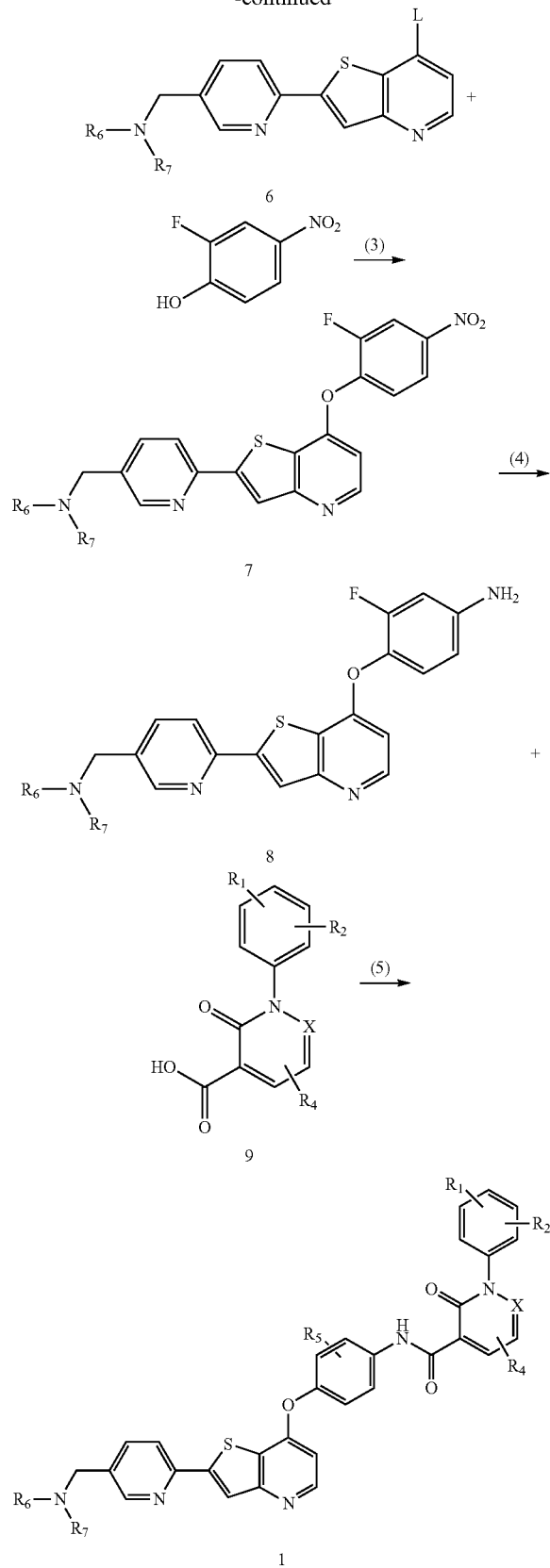

In the above Reaction Scheme 1, $R_1$ to $R_7$ and X are the same as defined in Formula 1, and L is a leaving group.

The above Reaction Scheme 1 gives the compound of Formula 1 through a total of five steps, starting from an aldehyde compound which is commercially available or is prepared by a known method.

Hereinafter, each step of Reaction Scheme 1 will be described in detail.

In Step 1, an aldehyde compound 2 is subjected to a general reductive animation reaction with a substituted amine compound 3 to prepare an amine compound 4. This reaction may be carried out using a base such as trimethylamine and diisopropylethylamine, but is generally carried out using commercially available sodium cyanoborohydride, sodium triacetoxyborohydride or the like under a weak acidic condition without using a base. As the reaction solvent, 1,2-dichloroethane, dichloromethane, methanol, ethanol, isopropanol or the like which does not adversely affect the reaction may be used. The reaction temperature is not particularly limited, but in general, the reaction may be carried out at a temperature ranging from a cold temperature to a warm temperature. Preferably, the reaction may be carried out at a temperature ranging from a cold temperature to room temperature.

In Step 2, the amine compound 4 prepared in the above Step 1 is subjected to a carbon-carbon coupling reaction with commercially available thieno[3,2-b]pyridine 5 to prepare a thienopyridine compound 6. This reaction may be carried out in the presence of an organometallic catalyst which may be used for a common carbon-carbon coupling reaction. Examples of organometallic catalysts which may be used for this purpose include nickel (0), palladium (0) and the like. In this reaction, palladium (0) may typically be used as the organometallic catalyst and, for example, tetrakis (triphenylphosphine) palladium, palladium acetate or the like may be used alone or in combination with n-butyl lithium and zinc chloride (II) to conduct the reaction. In addition, the above reaction may be preferably carried out in a solvent which does not adversely affect the reaction, such as N,N-dimethylformamide, toluene, acetonitrile, tetrahydrofuran, and the like. The reaction temperature is not particularly limited, but in general, the reaction may be carried out at a temperature ranging from a cold temperature to a warm temperature.

In Step 3, the thienopyridine compound 6 prepared in the above Step 2 is reacted with a commercially available phenol compound in the presence of a base such as potassium carbonate to prepare a phenoxy compound 7. This reaction is a general ether-forming reaction of a phenolic compound, and is carried out in the presence of a base which can be used for the ether-forming reaction. Examples of the base which may be used for this purpose include sodium hydrate (NaH), potassium carbonate, sodium carbonate, cesium carbonate, sodium alkoxide, potassium alkoxide, and the like. In addition, the above reaction is preferably carried out in a solvent which does not adversely affect the reaction, and examples of the solvent include dichloromethane, chloroform, tetrahydrofuran, diethyl ether, toluene, N,N-dimethylformamide, acetonitrile, diphenyl ether, and the like. The reaction temperature is not particularly limited, but in general, the reaction may be carried out at a temperature ranging from a cold temperature to a warm temperature. Preferably, the reaction may be carried out at a warm temperature.

In Step 4, the nitro group of the phenoxy compound 7 prepared in the above Step 3 is reduced in the presence of iron and ammonium chloride to prepare an amine compound 8. This reaction is a reduction reaction of a nitro compound to an amine, and may be carried out using various reducing agents such as hydrogen, iron, tin (II) chloride, zinc, and the like. In addition, the above reaction may preferably be carried out using a solvent which does not adversely affect the reaction, such as dichloromethane, ethyl acetate, methanol, ethanol, tetrahydrofuran, N,N-dimethylformamide, and the like. If necessary, water may be used as a co-solvent. The reaction temperature is not particularly limited, but in general, the reaction may be carried out at a temperature ranging from room temperature to a warm temperature. Preferably, the reaction may be carried out at a warm temperature.

In Step 5, the amine compound 8 prepared in the above Step 4 is subjected to a general amidation reaction with a carboxylic acid compound 9, which is commercially available or prepared by a known method, using a coupling reagent to prepare the compound of Formula 1. As the coupling reagent, commercially available 1-(3-dimethylaminopropyl)-3-ethylcarbodiimide (EDCI), 1,3-dicyclohexylcarbodiimide (DCC), 1,1-carbonyldiimidazole, and the like may be used. This reaction may be carried out without using a base, but it may also be carried out in the presence of a general base which can be used for an amidation reaction, such as 4-dimethylaminopyridine, pyridine, triethylamine, diethylisopropylamine, N-methylmorpholine, dimethylphenylamine, and the like. Further, the above reaction may be preferably carried out in a solvent which does not adversely affect the reaction, such as acetonitrile, dimethylformamide, dichloromethane, and the like. The reaction temperature is not particularly limited, but in general, the reaction may be carried out at a temperature ranging from a cold temperature to a warm temperature. Preferably, the reaction may be carried out at room temperature.

According to another embodiment, a compound of Formula 1 may be prepared according to the procedure of Reaction Scheme 2 below.

[Reaction Scheme 2]

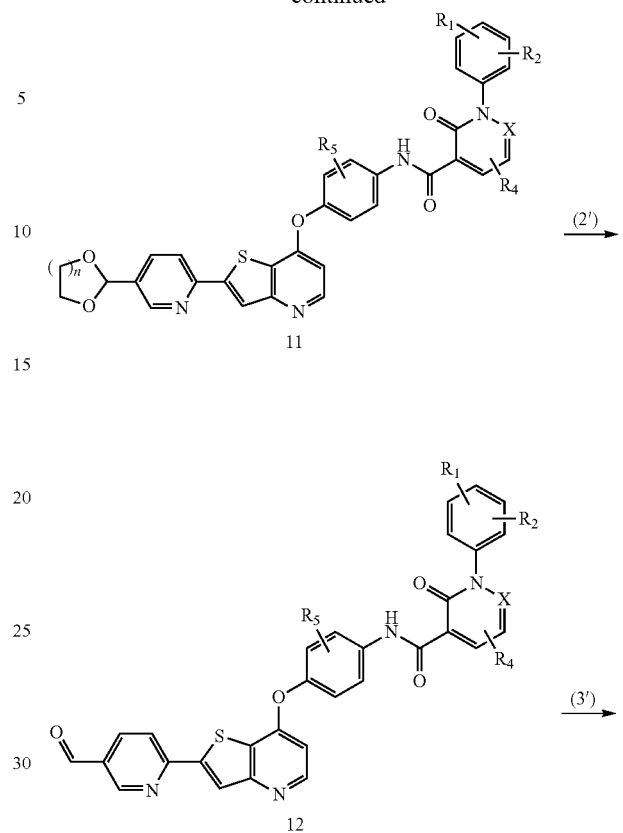

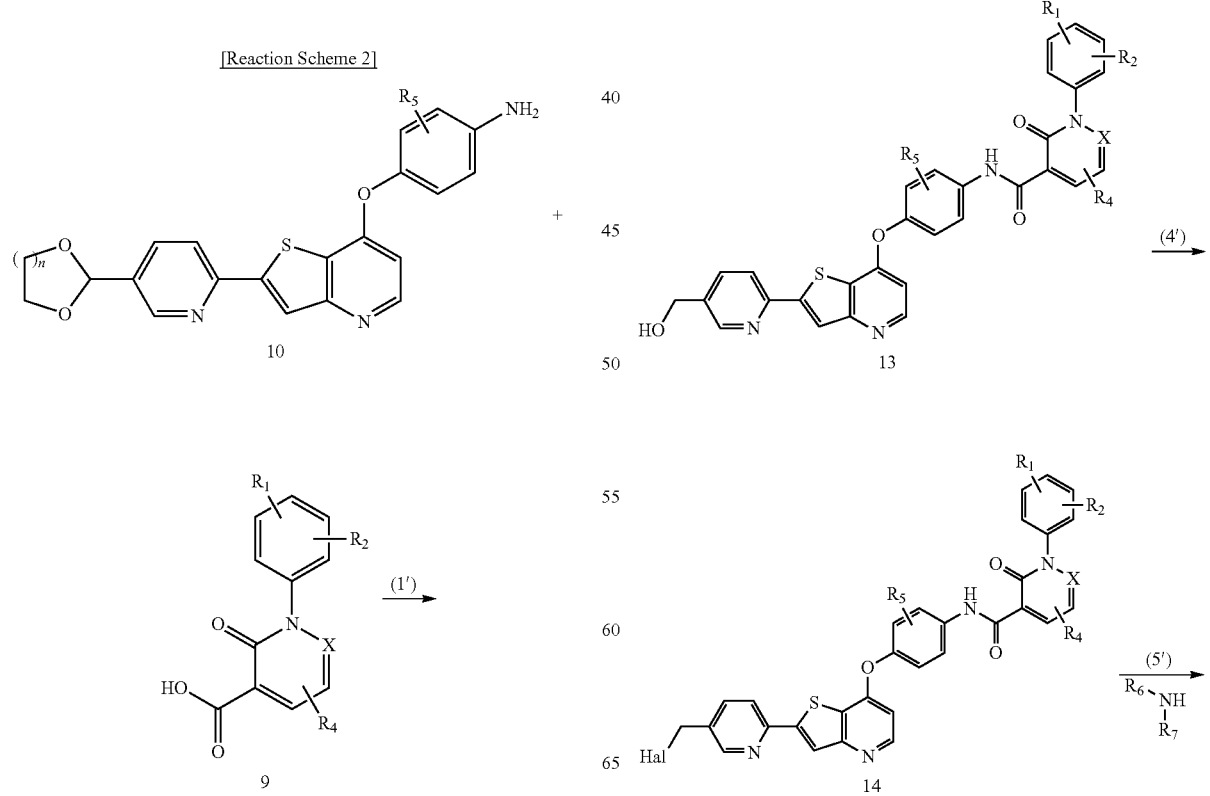

-continued

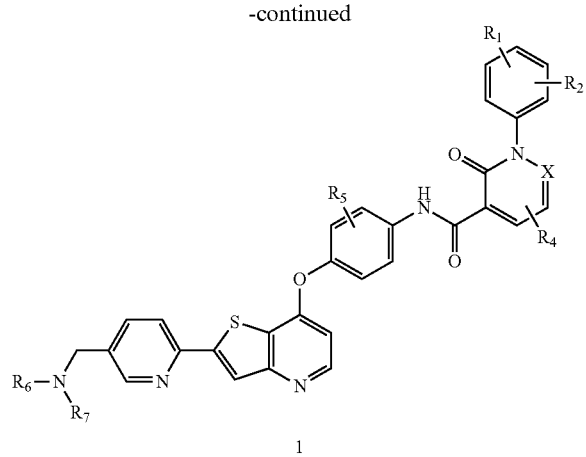

1

In the above Reaction Scheme 2, $R_1$ to $R_7$ and X are the same as defined in Formula 1, and n is an integer of 1 to 3.

The above Reaction Scheme 2 gives the compound of Formula 1 through a total of five steps, starting from an acetal compound which is commercially available or is prepared by a known method.

Hereinafter, each step of the Reaction Scheme 2 will be described in detail.

In Step 1', an acetal-amine compound 10, which can be easily prepared using the method of International Patent Publication No. WO 2009/026717, is subjected to an amidation reaction with a carboxylic acid compound 9 using a coupling reagent to prepare an acetal-amide compound 11. This reaction is generally carried out under the same conditions as in the amidation reaction for producing the compound of Formula 1 from the amine compound 8 in Step 5 of the above Reaction Scheme 1.

In Step 2', the acetal-amide compound 11 prepared in Step 1' above is subjected to a general deprotection reaction known in the art of organic synthesis under acidic conditions such as hydrochloric acid, trifluoroacetic acid, and the like to prepare an aldehyde compound 12.

In Step 3', the aldehyde compound 12 prepared in the above Step 2' is reduced to an alcohol compound 13 using a reducing agent Examples of the reducing agent include lithium aluminum hydride (LAH), sodium triacetoxyborohydride, sodium borohydride (NaBH$_4$), diisobutylaluminum hydride (DIBAL-H), and the like, which are commercially available. The reaction is preferably carried out in a solvent which does not adversely affect the reaction. Examples of solvents that may be used for this purpose include tetrahydrofuran, diethyl ether, 1,2-dichloroethane, alcohol, and the like. The reaction temperature is not particularly limited, but in general, the reaction may be carried out at a temperature ranging from a cold temperature to a warm temperature. Preferably, the reaction may be carried out at room temperature.

In step 4', the alcohol compound 13 prepared in the above Step 3' is subjected to a halogenation reaction to prepare a halogen compound 14. At this time, the conversion to the halogen compound may be generally carried out by using tribromophosphine, tetrabromomethane, thionyl chloride or the like which substitutes a halogen atom for a hydroxyl group. Further, the reaction may preferably be carried out in a solvent which does not adversely affect the reaction, such as chloroform, acetonitrile, dichloromethane, alcohols (e.g., methanol and ethanol), and the like. The reaction temperature is not particularly limited, but in general, the reaction may be carried out at a temperature ranging from a cold temperature to room temperature.

In step 5', the halogen compound 14 prepared in the above Step 4' is subjected to a general amination reaction to prepare the compound of Formula 1. Exemplary bases generally used in the amination reaction may include organic amines such as pyridine, triethylamine, diethylisopropylamine, and the like, and metal salts such as potassium carbonate, and the like. Further, the reaction may preferably be carried out in a solvent which does not adversely affect the reaction, such as dichloromethane, chloroform, tetrahydrofuran, diethyl ether, toluene, N,N-dimethylformamide, acetonitrile, and the like. The reaction temperature is not particularly limited, but in general, the reaction may be carried out at a temperature ranging from a cold temperature to a warm temperature. Preferably, the reaction may be carried out at a temperature ranging from room temperature to a warm temperature.

The desired compounds produced in the above reaction schemes may be separated and purified by a conventional method such as column chromatography, recrystallization, and the like.

Since the compound of Formula 1 or a pharmaceutically acceptable salt thereof has an excellent effect of inhibiting the activity of a protein kinase, the compound or a pharmaceutical composition comprising the same may be usefully used for preventing or treating diseases associated with the activity of a protein kinase.

As used herein, the term "prevention" refers to any action that inhibits or delays the occurrence, progression and recurrence of the above diseases, and the term "treatment" refers to any action that improves or beneficially alters the symptoms of the above disease upon administration of the above compound.

The present invention provides a use of a compound represented by Formula 1 or a pharmaceutically acceptable salt thereof for the prevention or treatment of a disease associated with the activity of a protein kinase.

The present invention also provides a use of a compound represented by Formula 1 or a pharmaceutically acceptable salt thereof for inhibiting the activity of a protein kinase.

The present invention also provides a use of a compound represented by Formula 1 or a pharmaceutically acceptable salt thereof for the manufacture of a medicament for preventing or treating a disease associated with the activity of a protein kinase.

The present invention also provides a use of a compound represented by Formula 1 or a pharmaceutically acceptable salt thereof for the manufacture of a medicament for inhibiting the activity of a protein kinase.

The present invention also provides a method of preventing or treating a disease associated with the activity of a protein kinase, which comprises administering a compound represented by Formula 1 or a pharmaceutically acceptable salt thereof to a subject in need thereof.

The present invention also provides a method for inhibiting the activity of a protein kinase, which comprises administering a compound represented by Formula 1 or a pharmaceutically acceptable salt thereof to a subject in need thereof.

The term "a subject in need" as used herein refers to any animal, in which a disease associated with the activity of the protein kinase has been or may be developed, such as a monkey, a cow, a horse, a sheep, a pig, a chicken, a turkey, a quail, a cat, a dog, a mouse, a rat, a rabbit and a guinea pig, as well as a human (a patient); and specifically, it may mean a mammal. In addition, the subject in need may be a biological sample.

The term "administration" as used herein refers to providing a predetermined substance to a subject in need thereof by any suitable method, and the compound of the present invention may be administered through any common route as long as it can reach the target tissue.

The present invention also provides a pharmaceutical composition for inhibiting the activity of a protein kinase, which comprises a compound represented by Formula 1 or a pharmaceutically acceptable salt thereof as an active ingredient.

The present invention also provides a pharmaceutical composition for preventing or treating a disease associated with the activity of a protein kinase, comprising a compound represented by Formula 1 or a pharmaceutically acceptable salt thereof as an active ingredient.

The compound and pharmaceutical composition of the present invention may inhibit c-MET family tyrosine kinases, more specifically RON tyrosine kinases. In addition, the compound and pharmaceutical composition of the present invention may inhibit the type 2 protein kinases ALK, Aurora B, AXL, DDR1, FLT3, KIT, LCK, LTK, MEK, MER, c-MET, RET, VEGFR2, TIE1, Tyro3, and the like (Pumima Wagh et al., *Adv Cancer Res.* 2008, 100: 1-33).

The disease associated with the activity of a protein kinase may be cancer, psoriasis, rheumatoid arthritis, inflammatory bowel disease or chronic obstructive pulmonary disease. Specifically, the cancer may be selected from the group consisting of breast cancer, lung cancer, stomach cancer, prostate cancer, uterine cancer, ovarian cancer, kidney cancer, pancreatic cancer, liver cancer, colorectal cancer, skin cancer, head and neck cancer, and thyroid cancer.

The present invention provides a pharmaceutical composition comprising the compound represented by Formula 1 or a pharmaceutically acceptable salt thereof, and a pharmaceutically acceptable additive.

The pharmaceutical composition may be used for the prevention or treatment of a disease associated with the activity of a protein kinase. Alternatively, the pharmaceutical composition may be used for inhibiting the activity of a protein kinase.

The pharmaceutical composition of the present invention may comprise as an active ingredient 0.1 wt % to 90 wt %, specifically 0.1 wt % to 75 wt %, more specifically 1 wt % to 50 wt % of a compound represented by Formula 1 or a pharmaceutically acceptable salt thereof, based on the total weight of the composition.

The pharmaceutical composition of the present invention may contain conventional, non-toxic pharmaceutically acceptable additives, which may be formulated into preparations according to conventional methods. For example, the pharmaceutical composition may further comprise a pharmaceutically acceptable carrier, diluent or excipient.

Examples of additives used in the composition of the present invention may include sweeteners, binders, solvents, solubilizers, wetting agents, emulsifiers, isotonic agents, absorbents, disintegrants, antioxidants, preservatives, lubricants, fillers, flavors, and the like. For example, the additive may be lactose, dextrose, sucrose, mannitol, sorbitol, cellulose, glycine, silica, talc, stearic acid, stearin, magnesium stearate, magnesium aluminosilicate, starch, gelatin, tragacanth gum, alginic acid, sodium alginate, methyl cellulose, sodium carboxymethyl cellulose, agar, water, ethanol, polyethylene glycol, polyvinylpyrrolidone, sodium chloride, calcium chloride, orange essence, strawberry essence, vanilla flavor, and the like.

The composition of the present invention may be formulated in various preparation forms for oral administration (e.g., tablets, pills, powders, capsules, syrups, or emulsions) or parenteral administration (e.g., intramuscular, intravenous, or subcutaneous injection).

Preferably, the composition of the present invention may be formulated into preparations for oral administration, and examples of the additives for this purpose include cellulose, calcium silicate, cornstarch, lactose, sucrose, dextrose, calcium phosphate, stearic acid, magnesium stearate, calcium stearate, gelatin, talc, surfactants, suspending agents, emulsifying agents, diluents, and the like.

Specifically, solid preparations for oral administration include tablets, pills, powders, granules, capsules and the like. Such solid preparations may be formulated by mixing at least one excipients, for example, starch, calcium carbonate, sucrose, lactose, gelatin, etc., into the composition. In addition to simple excipients, lubricants such as magnesium stearate and talc may also be used.

Further, examples of the liquid preparation for oral administration include suspensions, solutions, emulsions, syrups, and the like. In addition to water and liquid paraffin which are commonly used simple diluents, various excipients such as wetting agents, sweeteners, preservatives, and the like may also be used.

In addition, formulations for parenteral administration may include sterilized aqueous solutions, non-aqueous solvents, suspensions, emulsions, freeze-dried preparations and suppositories. For non-aqueous solution and suspension, propylene glycol, polyethylene glycol, vegetable oil such as olive oil, injectable ester such as ethyl oleate, and the like may be used. As the suppository base, Witepsol™, macrogol, Tween™ 61, cacao butter, laurin fat, glycerogelatin, and the like may be used. On the other hand, injections may include conventional additives such as solubilizers, isotonic agents, suspending agents, emulsifiers, stabilizers, preservatives, and the like.

The compound or composition of the present invention may be administered to a patient in a therapeutically effective amount or in a pharmaceutically effective amount.

As used herein, the term "therapeutically effective amount" or "pharmaceutically effective amount" refers to an amount of a compound or composition effective to prevent or treat a subject disease, which is sufficient to treat the disease at a reasonable benefit/risk ratio applicable to medical treatment but does not cause side effects. The level of the effective amount may be determined according to factors including the patient's health condition, the type and severity of the disease, the activity of the drug, the patient's sensitivity to the drug, the method of administration, the time of administration, the route of administration, the rate of release, the period of treatment, formulated or co-administered drugs, and other factors well known in the medical art.

The compound or composition of the present invention may be administered as an individual therapeutic agent or in combination with other therapeutic agents, may be administered sequentially or simultaneously with a conventional therapeutic agent, and may be administered in single or multiple doses. It is important to take into account all of the above factors and to administer the amount in which the maximum effect can be obtained in a minimal amount without side effects, and such amount may be easily determined by a person skilled in the art.

Specifically, the effective amount of the compound in the composition of the present invention may vary depending on the age, sex, and body weight of the patient, and is generally 0.1 mg to 1000 mg or 5 mg to 200 mg per 1 kg of body weight per day or every other day. It may be administered once a day or divided up to three doses a day. However, the effective amount may be increased or decreased according to the route of administration and disease severity, sex, weight, age, etc. of the patient, and thus the scope of the present invention is not limited thereto.

Preferably, the compound or composition of the present invention may be administered for tumor therapy in combination with chemotherapy, radiation therapy, immunotherapy, hormone therapy, bone marrow transplantation, stem cell replacement therapy, other biological therapies, surgical intervention, or combinations thereof. For example, the compound or composition of the present invention may be used as an adjunctive therapy in conjunction with other treatment strategies that proceed in the long term, or may be used to maintain the condition of the patient after tumor regression or chemoprevention therapy in severe patients.

Preferably, the pharmaceutical composition of the present invention may further comprise at least one active ingredient, and the further active ingredient may be anti-proliferative compounds such as aromatase inhibitors, anti-estrogens, topoisomerase I inhibitors, topoisomerase II inhibitors, microtubule active compounds, alkylating compounds, histone deacetylase inhibitors, compounds that induce cell differentiation processes, cyclooxygenase inhibitors, MMP inhibitors, mTOR inhibitors, anti-neoplastics, anti-metabolites, platin compounds, compounds that target/decrease the activity of protein or lipid kinase activity, anti-angiogenic compounds, compounds that target, decrease, or inhibit the activity of a protein or lipid phosphatase, gonadorelin agonists, anti-androgens, methionine aminopeptidase inhibitors, bisphosphonates, biological response modifiers, anti-proliferative antibodies, heparanase inhibitors, Ras tumorigenic isotype inhibitors, telomerase inhibitors, proteasome inhibitors, compounds used for the treatment of hematologic malignancies, a compounds which target, decrease or inhibit the activity of Flt-3, Hsp90 inhibitors, kinesin spindle protein inhibitors, MEK inhibitors, leucovorin, EDG binding agents, anti-leukemia compounds, ribonucleotide reductase inhibitors, S-adenosylmethionine decarboxylase inhibitors, hemostatic steroids, corticosteroids, other chemotherapeutic compounds, or photosensitizing compounds, but is not limited thereto.

Preferably, the further active ingredient may be a known anti-cancer agent. Non-limiting examples of such anticancer agent include DNA alkylating agents such as mechloethamine, chlorambucil, phenylalanine, mustard, cyclophosphamide, ifosfamide, carmustine (BCNU), lomustine (CCNU), streptozotocin, busulfan, thiotepa, cisplatin, and carboplatin; anti-cancer antibiotics such as dactinomycin (actinomycin D), doxorubicin (adriamycin), daunorubicin, idarubicin, mitoxantrone, plicamycin, mitomycin C, and bleomycin; and plant alkaloids such as vincristine, vinblastine, paclitaxel, docetaxel, etoposide, teniposide, topotecan, and irinotecan, and the like.

MODES FOR THE INVENTION

Hereinafter, the present invention will be described in detail with reference to examples. However, the following examples are for illustrative purposes only and are not intended to limit the scope of the invention.

Preparation Example 1. 4-ethoxy-1-(4-fluorophenyl)-2-oxo-1,2-dihydropyridine-3-carboxylic Acid Step 1: Synthesis of ethyl 4-ethoxy-2-oxo-1,2-dihydropyridine-3-carboxylate

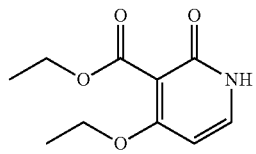

Triethyl orthoacetate (15 mL, 0.08 mol) and acetic acid (1.1 mL, 0.02 mol) were sequentially added to ethyl cyanoacetate (4.7 mL, 0.04 mol), and the mixture was stirred at 120° C. for 12 hours or more. The reaction mixture was concentrated, N,N-dimethylformamide diethyl acetal (8 mL, 0.05 mol) was added thereto, and the mixture was stirred at 70° C. for 2 hours or more. Then, 35 mL of acetic acid and 4 mL of distilled water were added to the reaction mixture, and the mixture was refluxed for 12 hours or more. The reaction mixture was cooled to room temperature, and a saturated aqueous solution of sodium bicarbonate and water were added thereto. The mixture was extracted with dichloromethane, and the organic layer was dried over anhydrous magnesium sulfate, followed by filtration and concentration under reduced pressure. 20 mL of ethyl acetate was added thereto, and the mixture was concentrated. The resulting solid was filtered to obtain the title compound (2.6 g, yield: 28%, orange solid).

$^1$H NMR (500 MHz, DMSO-$d_6$) δ 11.64 (brs, 1H), 7.47 (d, J=10 Hz, 1H), 6.21 (d, J=10 Hz, 1H), 4.18-4.10 (m, 4H), 1.26-1.20 (m, 6H)

Step 2: Synthesis of ethyl 4-ethoxy-1-(4-fluorophenyl)-2-oxo-1,2-dihydropyridine-3-carboxylate

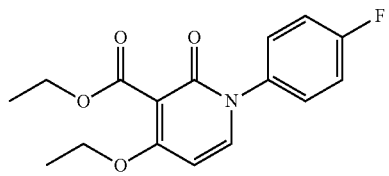 [SMILES: CCOC(=O)c1c(OCC)ccn(-c2ccc(F)cc2)c1=O]

4-Fluorophenylboronic acid (3.1 g, 22.7 mmol) and anhydrous copper (II) acetate (2.7 g, 15.1 mmol) were dissolved in dichloromethane, to the mixture were added 2.4 mL of pyridine and the compound obtained in the above Step 1 (1.6 g, 7.5 mmol), and the mixture was stirred at room temperature for 12 hours or more. The reaction mixture was filtered through a celite pad and extracted with water and dichloromethane. The separated organic layer was dried over anhydrous magnesium sulfate, filtered, and concentrated under reduced pressure. The resulting residue was purified by column chromatography to obtain the title compound (1.5 g, yield: 65%, white solid).

¹H NMR (500 MHz, DMSO-d₆) δ 7.81 (d, J=10.0 Hz, 1H), 7.46-7.43 (m, 2H), 7.36-7.32 (m, 2H), 6.44 (d, J=10.0 Hz, 1H), 4.24-4.16 (m, 4H), 1.28 (t, J=7.5 Hz, 3H), 1.22 (t, J=5.0 Hz, 3H)

Step 3: Synthesis of 4-ethoxy-1-(4-fluorophenyl)-2-oxo-1,2-dihydropyridine-3-carboxylic Acid

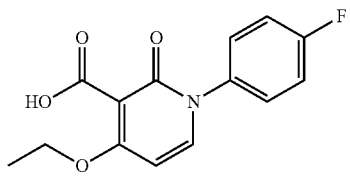 [SMILES: CCOc1ccn(-c2ccc(F)cc2)c(=O)c1C(=O)O]

The compound obtained in the above Step 2 (1.5 g, 4.91 mmol) was dissolved in a mixed solution of ethanol (15 mL) and water (10 mL), lithium hydroxide monohydrate (0.82 g, 19.6 mmol) was added thereto, and the mixture was stirred at 70° C. for 3 hours or more. The mixture was cooled to room temperature, concentrated under reduced pressure, and 1 N aqueous hydrochloric acid solution was slowly added dropwise thereto at 0° C. to maintain the pH at 2.0. The resulting solid was separated by filtration, washed with water, and then dried to give the title compound (1.1 g, yield: 84%, white solid).

¹H NMR (500 MHz, DMSO-d₆) δ 13.80 (brs, 1H), 7.97 (d, J=5.0 Hz, 1H), 7.52-7.50 (m, 2H), 7.49-7.36 (m, 2H), 6.60 (d, J=5.0 Hz, 1H), 4.30 (qt, J=7.5 Hz, 2H), 1.34 (t, J=7.5 Hz, 3H)

Preparation Example 2. 4-ethoxy-1-(3-fluorophenyl)-2-oxo-1,2-dihydropyridine-3-carboxylic Acid

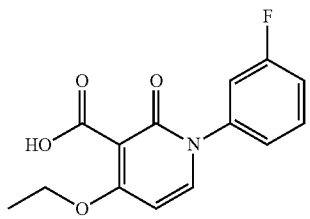 [SMILES: CCOc1ccn(-c2cccc(F)c2)c(=O)c1C(=O)O]

The synthesis route of Preparation Example 1 was repeated except that 3-fluorophenylboronic acid was used instead of 4-fluorophenylboronic acid in Step 2 to obtain the title compound (192 mg, yield: 73%, white solid).

¹H NMR (500 MHz, DMSO-d₆) δ 13.70 (brs, 1H), 7.99 (d, J=10.0 Hz, 1H), 7.60-7.56 (m, 1H), 7.43 (dt, J=10.0 and 5.0 Hz, 1H), 7.36 (td, J=10.0 and 5.0 Hz, 1H), 7.30 (dd, J=10.0 and 5.0 Hz, 1H), 6.61 (d, J=10.0 Hz, 1H), 4.30 (qt, J=5.0 Hz, 2H), 1.34 (t, J=5.0 Hz, 3H)

Preparation Example 3. 4-ethoxy-2-oxo-1-phenyl-1,2-dihydropyridine-3-carboxylic Acid

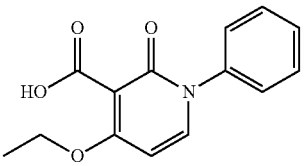 [SMILES: CCOc1ccn(-c2ccccc2)c(=O)c1C(=O)O]

The synthesis route of Preparation Example 1 was repeated except that phenylboronic acid was used instead of 4-fluorophenylboronic acid in Step 2 to obtain the title compound (0.7 g, yield: 80%, white solid).

¹H NMR (500 MHz, DMSO-d₆) δ 13.87 (brs, 1H), 7.98 (d, J=5.0 Hz, 1H), 7.54-7.52 (m, 2H), 7.50-7.49 (m, 1H), 7.44-7.43 (m, 2H), 6.61 (d, J=10.0 Hz, 1H), 4.30 (qt, J=7.5 Hz, 2H), 1.35 (t, J=7.5 Hz, 3H)

Preparation Example 4. 4-ethoxy-1-(4-chlorophenyl)-2-oxo-1,2-dihydropyridine-3-carboxylic Acid

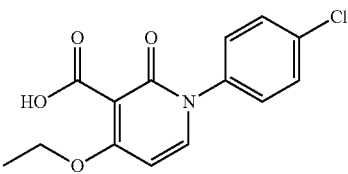 [SMILES: CCOc1ccn(-c2ccc(Cl)cc2)c(=O)c1C(=O)O]

The synthesis route of Preparation Example 1 was repeated except that 4-chlorophenylboronic acid was used instead of 4-fluorophenylboronic acid in Step 2 to obtain the title compound (121 mg, yield: 41%, white solid).

¹H NMR (500 MHz, DMSO-d₆) δ 13.71 (brs, 1H), 7.97 (d, J=5.0 Hz, 1H), 7.60 (d, J=10.0 Hz, 2H), 7.48 (d, J=10.0 Hz, 2H), 6.61 (d, J=10.0 Hz, 1H), 4.30 (qt, J=7.5 Hz, 2H), 1.34 (t, J=7.5 Hz, 3H)

Preparation Example 5. 4-ethoxy-2-oxo-1-[4-(trifluormethyl)phenyl]-1,2-dihydropyridine-3-carboxylic Acid

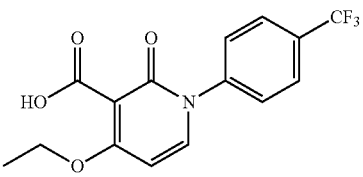 [SMILES: CCOc1ccn(-c2ccc(C(F)(F)F)cc2)c(=O)c1C(=O)O]

The synthesis route of Preparation Example 1 was repeated except that 4-trifluoromethylbenzeneboronic acid was used instead of 4-fluorophenylboronic acid in Step 2 to obtain the title compound (381 mg, yield: 58%, white solid).

¹H NMR (500 MHz, DMSO-d₆) δ 13.80 (brs, 1H), 7.98 (d, J=5.0 Hz, 1H), 7.52-7.49 (m, 2H), 7.39-7.35 (m, 2H), 6.61 (d, J=5.0 Hz, 1H), 4.30 (qt, J=7.5 Hz, 2H), 1.34 (t, J=10 Hz, 3H)

Preparation Example 6. 4-ethoxy-1-(4-methoxyphenyl)-2-oxo-1,2-dihydropyridine-3-carboxylic Acid

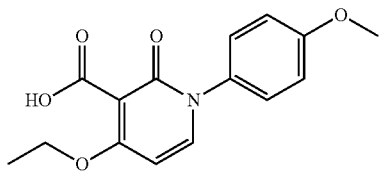 [SMILES: CCOc1ccn(-c2ccc(OC)cc2)c(=O)c1C(=O)O]

The synthesis route of Preparation Example 1 was repeated except that 4-methoxyphenylboronic acid was used instead of 4-fluorophenylboronic acid in Step 2 to obtain the title compound (240 mg, yield: 91%, white solid).

$^1$H NMR (500 MHz, DMSO-$d_6$) δ 14.01 (brs, 1H), 7.96 (d, J=10.0 Hz, 1H), 7.36-7.33 (m, 2H), 7.08-7.04 (m, 2H), 6.59 (d, J=10.0 Hz, 1H), 4.30 (qt, J=5.0 Hz, 2H), 3.81 (s, 3H), 1.35 (t, J=5.0 Hz, 3H)

Preparation Example 7. 4-ethoxy-1-(3-methoxyphenyl)-2-oxo-1,2-dihydropyridine-3-carboxylic Acid

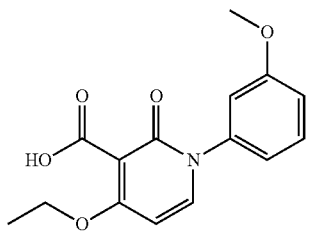 [SMILES: CCOc1ccn(-c2cccc(OC)c2)c(=O)c1C(=O)O]

The synthesis route of Preparation Example 1 was repeated except that 3-methoxyphenylboronic acid was used instead of 4-fluorophenylboronic acid in Step 2 to obtain the title compound (188 mg, yield: 69%, white solid).

$^1$H NMR (500 MHz, DMSO-$d_6$) δ 13.90 (brs, 1H), 7.97 (d, J=10.0 Hz, 1H), 7.43 (t, J=10.0 Hz, 1H), 7.07-7.03 (m, 2H), 6.99 (d, J=10.0 Hz, 1H), 6.60 (d, J=10.0 Hz, 1H), 4.30 (qt, J=5.0 Hz, 2H), 3.79 (s, 3H), 1.34 (t, J=5.0 Hz, 3H)

Preparation Example 8. 1-(4-fluorophenyl)-4-methoxy-2-oxo-1,2-dihydropyridine-3-carboxylic Acid

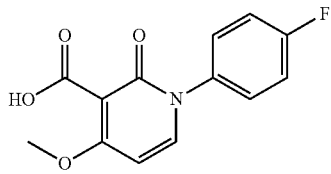 [SMILES: COc1ccn(-c2ccc(F)cc2)c(=O)c1C(=O)O]

The synthesis route of Preparation Example 1 was repeated except that trimethyl orthoacetate was used as a starting material to obtain the title compound (0.1 g, yield: 36.8%, white solid).

$^1$H NMR (500 MHz, DMSO-$d_6$) δ 13.91 (brs, 1H), 8.04 (d, J=5.0 Hz, 1H), 7.53-7.49 (m, 2H), 7.41-7.36 (m, 2H), 6.65 (d, J=5.0 Hz, 1H), 3.98 (s, 3H)

Preparation Example 9. 4-methoxy-1-(4-chlorophenyl)-2-oxo-1,2-dihydropyridine-3-carboxylic Acid

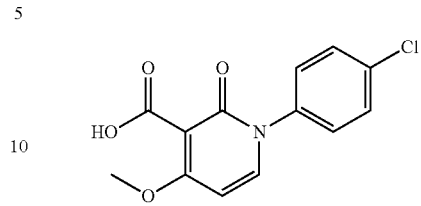

The synthesis route of Preparation Example 8 was repeated except that 4-chlorophenylboronic acid was used instead of 4-fluorophenylboronic acid in Step 2 to obtain the title compound (163 mg, yield: 41%, white solid).

$^1$H NMR (500 MHz, DMSO-$d_6$) δ 13.84 (brs, 1H), 8.03 (d, J=10.0 Hz, 1H), 7.62-7.60 (m, 2H), 7.50-7.48 (m, 2H), 6.64 (d, J=5.0 Hz, 1H), 3.97 (s, 3H)

Preparation Example 10. 1-methoxy-2-oxo-1-phenyl-1,2-dihydropyridine-3-carboxylic Acid

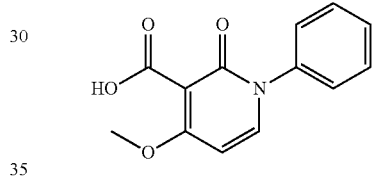

The synthesis route of Preparation Example 8 was repeated except that phenylboronic acid was used instead of 4-fluorophenylboronic acid in Step 2 to obtain the title compound (0.14 g, yield: 32.4%, white solid).

$^1$H NMR (500 MHz, DMSO-$d_6$) δ 13.91 (brs, 1H), 8.05 (d, J=5.0 Hz, 1H), 7.56-7.42 (m, 5H), 6.64 (d, J=10.0 Hz, 1H), 3.98 (s, 3H)

Preparation Example 11. 1-(4-fluorophenyl)-2-oxo-1,2-dihydropyridine-3-carboxylic Acid

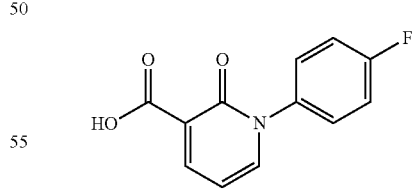

The synthesis route of Steps 2 and 3 of Preparation Example 1 was repeated except that methyl 2-hydroxynicotinate was used as a starting material to obtain the title compound (0.18 g, yield: 94.7%, white solid).

$^1$H NMR (500 MHz, DMSO-$d_6$) δ 14.24 (brs, 1H), 8.50 (d, J=5.0 Hz, 1H), 8.22 (d, J=5.0 Hz, 1H), 7.65-7.60 (m, 2H), 7.45-7.41 (m, 2H), 6.80 (t, J=5.0 Hz, 1H)

Preparation Example 12. 2-oxo-1-phenyl-1,2-dihydropyridine-3-carboxylic Acid

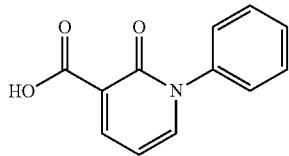 [SMILES: O=C(O)c1cccn(-c2ccccc2)c1=O]

The synthesis route of Steps 2 and 3 of Preparation Example 1 was repeated except that methyl 2-hydroxynicotinate and phenylboronic acid were used as starting materials to obtain the title compound (0.15 g, yield: 81.8%, white solid).

$^1$H NMR (500 MHz, DMSO-d$_6$) δ 14.31 (brs, 1H), 8.50 (d, J=5.0 Hz, 1H), 8.23 (d, J=5.0 Hz, 1H), 7.57-7.54 (m, 5H), 6.80 (t, J=5.0 Hz, 1H)

Preparation Example 13. 6-methyl-2-oxo-1-phenyl-1,2-dihydropyridine-3-carboxylic Acid

Step 1: Synthesis of ethyl 3-oxo-3-(phenylamino)propionate

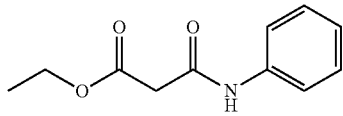

Aniline (98 μL, 1.07 mmol) and triethylamine (0.16 mL, 1.18 mmol) were sequentially added to 2 mL of tetrahydrofuran. The mixture was cooled to 0° C., ethyl malonyl chloride (0.15 mL, 0.18 mmol) was added thereto, and the mixture was stirred at 0° C. for 30 minutes. The reaction was terminated with 1 N aqueous hydrochloric acid solution. The mixture was extracted with ethyl acetate, and the separated organic layer was dried over anhydrous sodium sulfate. The solvent was filtered off and the filtrate was concentrated under reduced pressure. The resulting residue was purified by column chromatography to obtain the title compound (0.22 g, yield: 99%, yellow solid).

$^1$H NMR (500 MHz, DMSO-d$_6$) δ 9.25 (brs, 1H), 7.55 (d, J=5.0 Hz, 2H), 7.33 (t, J=5.0 Hz, 2H), 7.12 (t, J=10.0 Hz, 1H), 4.25 (qt, J=10.0 Hz, 2H), 3.48 (s, 2H), 1.33 (t, J=5.0 Hz, 3H)

Step 2: Synthesis of 6-methyl-2-oxo-1-phenyl-1,2-dihydropyridine-3-carboxylic Acid

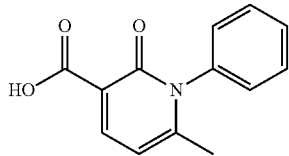 [SMILES: Cc1ccc(C(=O)O)c(=O)n1-c1ccccc1]

To a solution of ethyl 3-oxo-3-(phenylamino)propionate (220 mg, 1.06 mmol) in 3 mL of ethanol, 1,1-dimethoxy-3-butanone (0.17 mL, 1.27 mmol) and sodium ethoxide (20 wt % in EtOH, 1.2 mL) were sequentially added and the mixture was stirred at 80° C. for 3 hours. The mixture was cooled to room temperature and concentrated under reduced pressure. 1 N aqueous hydrochloric acid solution was slowly added dropwise to the resulting residue, followed by extraction with dichloromethane. The separated organic layer was dried over anhydrous sodium sulfate and concentrated under reduced pressure. The resulting residue was washed with a mixture of ethyl acetate:hexane (1:1) and dried to obtain the title compound (0.15 g, yield: 62%, brown solid).

$^1$H NMR (500 MHz, DMSO-d$_6$) δ 14.00 (brs, 1H), 8.52 (d, J=5.0 Hz, 1H), 7.65-7.57 (m, 3H), 7.28-7.24 (m, 2H), 6.56 (d, J=5.0 Hz, 1H), 2.17 (s, 3H)

Preparation Example 14. 6-methyl-2-oxo-1-(4-fluorophenyl)-1,2-dihydropyridine-3-carboxylic Acid

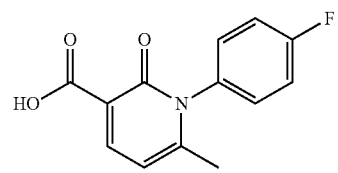 [SMILES: Cc1ccc(C(=O)O)c(=O)n1-c1ccc(F)cc1]

The synthesis route of Preparation Example 13 was repeated except that 4-fluoroaniline was used instead of aniline in Step 1 to obtain the title compound (148 mg, yield: 67%, brown solid).

$^1$H NMR (500 MHz, DMSO-d$_6$) δ 14.22 (brs, 1H), 8.40 (d, J=5.0 Hz, 1H), 7.53-7.51 (m, 2H), 7.46-7.43 (m, 2H), 2.09 (s, 3H)

Preparation Example 15. 5-bromo-1-(4-fluorophenyl)-2-oxo-1,2-dihydropyridine-3-carboxylic Acid

Step 1: Synthesis of methyl-5-bromo-2-oxo-1,2-dihydropyridine-3-carboxylate

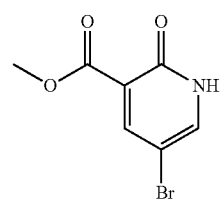

Methyl 2-hydroxynicotinate (500 mg, 3.27 mmol) and N-bromosuccinimide (756 mg, 4.25 mmol) were dissolved in dichloromethane and the mixture was stirred at 50° C. for 48 hours. The mixture was cooled to room temperature and then concentrated under reduced pressure. The resulting residue was filtered with a small amount of dichloromethane to obtain the title compound (0.3 g, yield: 40%, yellow solid).

$^1$H NMR (500 MHz, DMSO-d$_6$) δ 8.07 (d, J=5.0 Hz, 1H), 7.98 (d, J=5.0 Hz, 1H), 3.75 (s, 3H)

Step 2: Synthesis of methyl 5-bromo-2-oxo-1-(4-fluorophenyl)-1,2-dihydropyridine-3-carboxylate

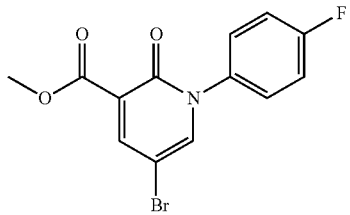 [SMILES: COC(=O)c1cc(Br)cn(-c2ccc(F)cc2)c1=O]

The compound prepared in the above Step 1 (300 mg, 1.29 mmol) was dissolved in dichloromethane, and 4-fluorophenylboronic acid (543 mg, 3.88 mmol), anhydrous copper (II) acetate (469 mg, 2.58 mmol), and pyridine (0.42 mL, 5.16 mmol) were sequentially added to this solution. The mixture was stirred at room temperature for 24 hours. The mixture was filtered through a celite pad and then extracted with dichloromethane. The separated organic layer was dried over anhydrous sodium sulfate, filtered, and concentrated under reduced pressure. The resulting residue was purified by column chromatography to obtain the title compound (0.14 g, yield: 36%, yellow solid).

$^1$H NMR (500 MHz, DMSO-d$_6$) δ 8.30 (s, 1H), 8.16 (s, 1H), 7.54-7.50 (m, 2H), 7.39-7.34 (m, 2H), 3.76 (s, 3H)

Step 3: Synthesis of 5-bromo-1-(4-fluorophenyl)-2-oxo-1,2-dihydropyridine-3-carboxylic Acid

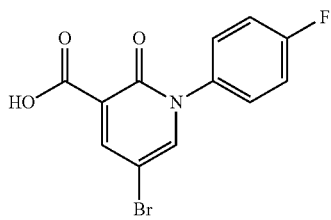

The synthesis route of Step 3 of Preparation Example 1 was repeated except that the compound prepared in the above Step 2 (142 mg, 0.44 mmol) was used as a starting material to obtain the title compound (43.4 mg, yield: 31%, white solid).

$^1$H NMR (500 MHz, DMSO-ds) S 8.55 (d, J=5.0 Hz, 1H), 8.42 (d, J=5.0 Hz, 1H), 7.64-7.59 (m, 2H), 7.44-7.39 (m, 2H)

Preparation Example 16. 5-chloro-1-(4-fluorophenyl)-2-oxo-1,2-dihydropyridine-3-carboxylic Acid

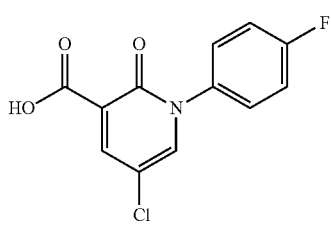 [SMILES: O=C(O)c1cc(Cl)cn(-c2ccc(F)cc2)c1=O]

The synthesis route of Preparation Example 15 was repeated except that N-chlorosuccinimide was used instead of N-bromosuccinimide in Step 1 to obtain the title compound (53 mg, yield: 20%, brown solid).

$^1$H NMR (500 MHz, DMSO-d$_6$) δ 8.53 (d, J=5.0 Hz, 1H), 8.39 (s, 1H), 7.63-7.61 (m, 2H), 7.44-7.40 (m, 2H)

Preparation Example 17. 4-methyl-2-oxo-1-(4-fluorophenyl)-1,2-dihydropyridine-3-carboxylic Acid Step 1: Synthesis of ethyl 2-(4-fluoroanilinocarbonyl)-3-methyl-2-butylate

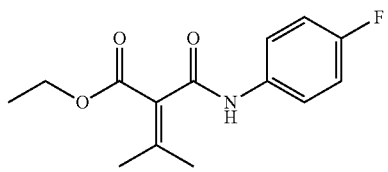 [SMILES: CCOC(=O)C(C(=O)Nc1ccc(F)cc1)=C(C)C]

A mixture of 4-fluoroaniline (0.20 mL, 2.05 mmol), diethyl isopropylidenemalonate (1.60 mL, 8.20 mmol), and imidazole (139 mg, 2.05 mmol) was stirred at 200° C. for 5 hours. The mixture was cooled to room temperature and concentrated under reduced pressure. The resulting residue was purified by column chromatography to obtain the title compound (151 mg, yield: 28%, yellow oil).

$^1$H NMR (500 MHz, DMSO-d$_6$) δ 10.25 (s, 1H), 7.65-7.62 (m, 2H), 7.17-7.13 (m, 2H), 4.12 (qt, J=5.0 Hz, 2H), 2.16 (s, 3H), 1.88 (s, 3H), 1.16 (t, J=5.0 Hz, 3H)

Step 2: Synthesis of ethyl 4-methyl-2-oxo-1-(4-fluorophenyl)-1,2-dihydropyridine-3-carboxylate

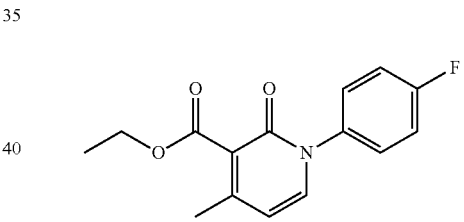

A mixture of the compound prepared in the above Step 1 (96 mg, 0.36 mmol) and 1,1-dimethoxy-N,N-dimethylmethanamine (72 μL, 0.54 mmol) was stirred at 100° C. for 1 hour. The mixture was cooled to room temperature and concentrated under reduced pressure. The resulting residue was purified by column chromatography to obtain the title compound (34 mg, yield: 34%, brown solid).

$^1$H NMR (500 MHz, CDCl$_3$) δ 7.36-7.33 (m, 2H), 7.27-7.26 (m, 1H), 7.17-7.13 (m, 2H), 6.13 (d, J=5.0 Hz, 1H), 4.39 (qt, J=5.0 Hz, 2H), 2.28 (s, 3H), 1.37 (t, J=5.0 Hz, 3H)

Step 3: Synthesis of 4-methyl-2-oxo-1-(4-fluorophenyl)-1,2-dihydropyridine-3-carboxylic Acid

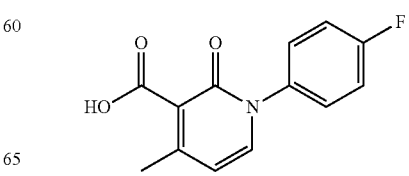

The synthesis route of Step 3 of Preparation Example 1 was repeated except that the compound prepared in the above Step 2 (34 mg, 0.12 mmol) was used as a starting material to obtain the title compound (29 mg, yield: 100%, yellow solid).

$^1$H NMR (500 MHz, DMSO-$d_6$) δ 7.90 (d, J=10.0 Hz, 1H), 7.56-7.52 (m, 2H), 7.42-7.37 (m, 2H), 6.56 (d, J=10.0 Hz, 1H), 2.52 (s, 3H)

Preparation Example 18. 4-methyl-2-oxo-1-phenyl-1,2-dihydropyridine-3-carboxylic Acid

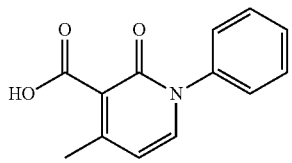 [SMILES: Cc1ccn(-c2ccccc2)c(=O)c1C(=O)O]

The synthesis route of Preparation Example 17 was repeated except that aniline was used instead of 4-fluoroaniline in Step 1 to obtain the title compound (121 mg, yield: 50%, white solid).

$^1$H NMR (500 MHz, DMSO-$d_6$) δ 14.52 (brs, 1H), 7.92 (d, J=10.0 Hz, 1H), 7.57-7.54 (m, 2H), 7.52-7.46 (m, 3H), 6.57 (d, J=5.0 Hz, 1H), 2.53 (s, 3H)

Preparation Example 19. 5-methyl-2-oxo-1-(4-fluorophenyl)-1,2-dihydropyridine-3-carboxylic Acid Step 1: Synthesis of ethyl 3-oxo-3-(4-fluorophenylamino)propionate

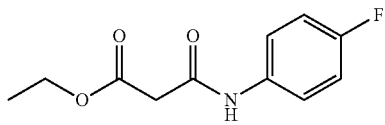 [SMILES: CCOC(=O)CC(=O)Nc1ccc(F)cc1]

4-Fluoroaniline (0.43 mL, 4.50 mmol) and triethylamine (0.69 mL, 4.95 mmol) were sequentially added to 10 mL of tetrahydrofuran. The mixture was cooled to 0° C., ethyl malonyl chloride (0.63 mL, 4.95 mmol) was added thereto, and the mixture was stirred at 0° C. for 30 minutes. The reaction was terminated with 1 N aqueous hydrochloric acid solution, the mixture was extracted with ethyl acetate, and the separated organic layer was dried over anhydrous sodium sulfate. The solvent was filtered off and the filtrate was concentrated under reduced pressure. The resulting residue was purified by column chromatography to obtain the title compound (0.98 g, yield: 97%, white solid).

$^1$H NMR (500 MHz, DMSO-$d_6$) δ 10.23 (brs, 1H), 7.61-7.56 (m, 2H), 7.18-7.13 (m, 2H), 4.12 (qt, J=5.0 Hz, 2H), 3.44 (s, 2H), 1.20 (t, J=5.0 Hz, 3H)

Step 2: Synthesis of ethyl 5-methyl-2-oxo-1-(4-fluorophenyl)-1,2-dihydropyridine-3-carboxylate

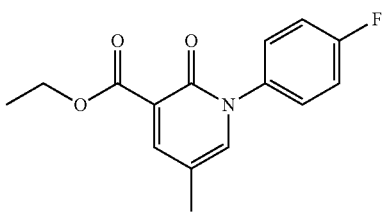 [SMILES: CCOC(=O)c1cc(C)cn(-c2ccc(F)cc2)c1=O]

The compound prepared in the above Step 1 (100 mg, 0.44 mmol) was dissolved in 0.6 mL of ethanol under nitrogen atmosphere, and 3-dimethylamino-2-methylacrylaldehyde (0.16 mL, 1.33 mmol) and acetic acid (0.04 mol) were added thereto. The mixture was stirred at 80° C. for 41 hours. The mixture was cooled to room temperature, washed with ethyl acetate and saturated aqueous sodium bicarbonate, and then the organic layer was dried over anhydrous sodium sulfate. The solvent was filtered off and the filtrate was concentrated under reduced pressure. The resulting residue was purified by column chromatography to obtain the title compound (39.1 mg, yield: 32%, yellow solid).

$^1$H NMR (500 MHz, DMSO-$d_6$) δ 7.98 (s, 1H), 7.77 (s, 1H), 7.49-7.46 (m, 2H), 7.37-7.34 (m, 2H), 4.21 (qt, J=5.0 Hz, 2H), 2.09 (s, 3H), 1.25 (t, J=5.0 Hz, 3H)

Step 3: Synthesis of 5-methyl-2-oxo-1-(4-fluorophenyl)-1,2-dihydropyridine-3-carboxylic Acid

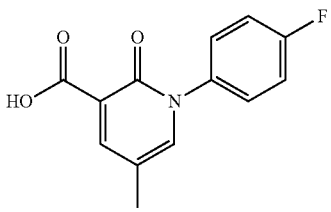 [SMILES: Cc1cc(C(=O)O)c(=O)n(-c2ccc(F)cc2)c1]

The synthesis route of Step 3 of Preparation Example 1 was repeated except that the compound prepared in the above Step 2 (39 mg, 0.14 mmol) was used as a starting material to obtain the title compound (26 mg, yield: 75%, white solid).

$^1$H NMR (500 MHz, DMSO-$d_6$) δ 14.51 (brs, 1H), 8.40 (s, 1H), 8.09 (s, 1H), 7.63-7.60 (m, 2H), 7.44-7.41 (m, 2H), 2.20 (s, 3H)

Preparation Example 20. 1-(4-fluorophenyl)-5,6-dimethyl-2-oxo-1,2-dihydropyridine-3-carboxylic Acid Step 1: Synthesis of 2-methyl-3-oxobutanal Sodium Salt

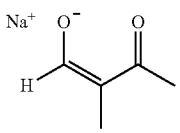

Sodium methoxide (750 mg, 13.9 mmol) was added to 11 mL of diethyl ether and 0.2 mL of methanol, and a mixed solution of 2-butanone (1.42 mL, 13.9 mmol) and ethyl formate (1.14 mL, 14.1 mmol) was slowly added dropwise thereto at 0° C. After 30 minutes, the mixture was warmed to room temperature and stirred for 12 hours. The solid formed during the reaction was filtered, washed with diethyl ether, and then dried to obtain the title compound (1.29 g, yield: 76%, white solid).

Step 2: Synthesis of 4-fluorophenyl-2-cyanoacetamide

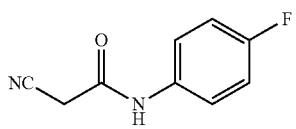 [SMILES: N#CCC(=O)Nc1ccc(F)cc1]

Ethyl cyanoacetate (0.94 mL, 8.84 mmol) was dissolved in N, N-dimethylformamide, 4-fluoroaniline (0.85 mL, 8.84 mmol) was added thereto, and the mixture was refluxed for 12 hours. The mixture was cooled to room temperature, an excessive amount of water was slowly added thereto, and the resulting solid was filtered and dried to obtain the title compound (800 mg, yield: 51%, brown solid).

$^1$H NMR (500 MHz, DMSO-$d_6$) δ 10.35 (s, 1H), 7.58-7.54 (m, 2H), 7.20-7.15 (m, 2H), 3.89 (s, 2H)

Step 3: Synthesis of 1-(4-fluorophenyl)-5,6-dimethyl-2-oxo-1,2-dihydropyridine-3-carbonitrile

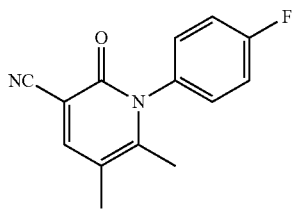 [SMILES: Cc1cc(C#N)c(=O)n(-c2ccc(F)cc2)c1C]

The compound prepared in Step 1 (480 mg, 3.93 mmol) and the compound prepared in Step 2 (538 mg, 3.02 mmol) were dissolved in N, N-dimethylformamide, and then piperidine (0.06 mL, 0.60 mmol) and acetic acid (0.23 mL, 3.93 mmol) were sequentially added thereto. The mixture was stirred at 135° C. for 12 hours. The mixture was cooled to room temperature and extracted with ethyl acetate. The separated organic layer was dried over anhydrous sodium sulfate, and then concentrated under reduced pressure. The resulting residue was purified by column chromatography to obtain the title compound (411 mg, yield: 56%, orange solid).

$^1$H NMR (500 MHz, DMSO-$d_6$) δ 8.14 (s, 1H), 7.43-7.36 (m, 4H), 2.10 (s, 3H), 1.94 (s, 3H)

Step 4: Synthesis of 1-(4-fluorophenyl)-5,6-dimethyl-2-oxo-1,2-dihydropyridine-3-carboxylic Acid

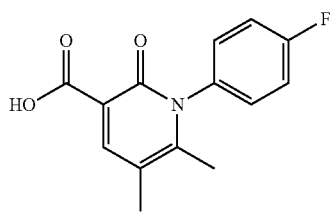 [SMILES: Cc1cc(C(=O)O)c(=O)n(-c2ccc(F)cc2)c1C]

An aqueous solution of sulfuric acid (0.5 mL of sulfuric acid+0.5 mL of water) was added to the compound prepared in the above Step 3 (100 mg, 0.41 mmol), and the mixture was stirred at 120° C. for 1.5 hours. The mixture was cooled to room temperature and then an excessive amount of water was added thereto. The resulting solid was filtered to obtain the title compound (80 mg, yield: 74%, yellow solid).

$^1$H NMR (500 MHz, DMSO-$d_6$) δ 14.44 (s, 1H), 8.37 (s, 1H), 7.47-7.45 (m, 4H), 2.23 (s, 3H), 2.03 (s, 3H)

Preparation Example 21. 2-(4-fluorophenyl)-3-oxo-2,3-dihydropyridazine-4-carboxylic Acid Step 1: Synthesis of (E)-2-[2-(4-fluorophenyl)hydrazinylidene]acetaldehyde

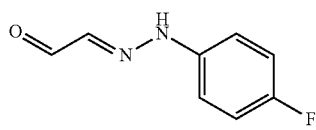 [SMILES: O=C/C=N/Nc1ccc(F)cc1]

1-(4-Fluorophenyl)hydrazine hydrochloride (0.50 g, 3.0 mmol) was dissolved in water and acetic acid, and an aqueous glyoxal solution (40 wt % in $H_2O$, 1.76 ml, 15.4 mmol) was added thereto. The mixture was stirred for 3 hours or more. The resulting solid was filtered and dried to obtain the title compound (0.43 g, yield: 84%, brown solid).

$^1$H NMR (500 MHz, CDCl$_3$) δ 11.76 (brs, 1H), 9.47 (d, J=5.0 Hz, 1H), 7.34 (d, J=5.0 Hz, 1H), 7.23-7.17 (m, 4H)

Step 2: Synthesis of (E)-5-{2-[2-(4-fluorophenyl)hydrazinylidene]ethylidene}-2,2-dimethyl-1,3-dioxane-4,6-dione

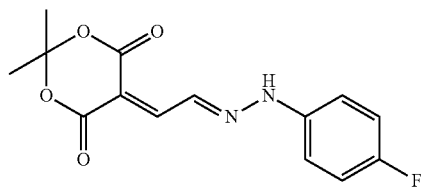 [SMILES: CC1(C)OC(=O)C(=C/C=N/Nc2ccc(F)cc2)C(=O)O1]

The compound prepared in the above Step 1 (0.43 g, 2.59 mmol) was dissolved in toluene, and isopropylidene malonate (0.37 g, 2.59 mmol) was added thereto. Then, to the mixture were added 0.2 ml each of piperidine and acetic acid, and the mixture was stirred at room temperature for 3 hours or more. The resulting solid was filtered and dried to obtain the title compound (0.73 g, yield: 97%, red solid).
¹H NMR (500 MHz, CDCl₃) δ 8.83 (d, J=10.0 Hz, 1H), 8.29 (d, J=10.0 Hz, 1H), 7.34-7.05 (m, 4H), 1.76 (6H, S)

Step 3: Synthesis of 2-(4-fluorophenyl)-3-oxo-2,3-dihydropyridazine-4-carboxylic Acid

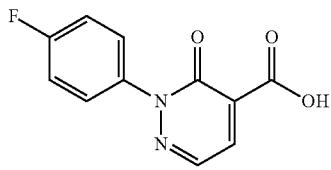 [SMILES: O=C(O)c1ccnn(-c2ccc(F)cc2)c1=O]

The compound obtained in the above Step 2 (0.73 g, 2.5 mmol) was dissolved in methanol, sodium methoxide (0.16 g, 3.0 mmol) was added thereto, and the mixture was refluxed for 2 hours or more. The mixture was cooled to room temperature, and the resulting solid was filtered and dissolved in purified water. The resulting solution was acidified with a 1 N aqueous hydrochloric acid solution. The re-formed solid was filtered and dried to obtain the title compound (0.36 g, yield: 61%, yellow solid).
¹H NMR (500 MHz, CDCl₃) δ 8.31 (s, 2H), 7.66-7.62 (m, 2H), 7.28-7.23 (m, 2H)

Preparation Example 22. 2-(4-fluorophenyl)-5-methyl-3-oxo-2,3-dihydropyridazine-4-carboxylic Acid

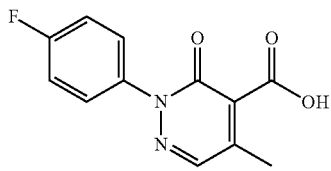 [SMILES: Cc1cnn(-c2ccc(F)cc2)c(=O)c1C(=O)O]

The synthesis route of Preparation Example 21 was repeated except that pyruvic aldehyde (35~45 wt % in H₂O) was used as a starting material to obtain the title compound (0.12 g, yield: 15.7%, white solid).
¹H NMR (500 MHz, CDCl₃) δ 13.84 (brs, 1H), 8.19 (s, 1H), 7.61-7.58 (m, 2H), 7.26-7.19 (m, 2H), 2.54 (s, 3H)

Preparation Example 23. 5-methyl-3-oxo-2-phenyl-2,3-dihydropyridazine-4-carboxylic Acid

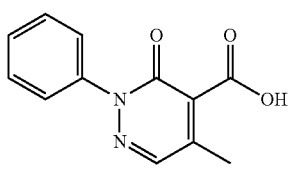 [SMILES: Cc1cnn(-c2ccccc2)c(=O)c1C(=O)O]

The synthesis route of Preparation Example 21 was repeated except that pyruvic aldehyde (35~45 wt % in H₂O) and phenylhydrazine hydrochloride were used as starting materials to obtain the title compound (0.13 g, yield: 18.6%, brown solid).

¹H NMR (500 MHz, CDCl₃) δ 13.95 (brs, 1H), 8.20 (s, 1H), 7.59-7.26 (m, 5H), 2.55 (s, 3H)

Preparation Example 24. 3-oxo-2-phenyl-2,3-dihydropyridazine-4-carboxylic Acid

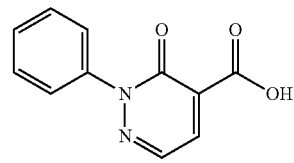 [SMILES: O=C(O)c1ccnn(-c2ccccc2)c1=O]

The synthesis route of Preparation Example 21 was repeated except that phenylhydrazine hydrochloride was used as a starting material to obtain the title compound (0.07 g, yield: 10.8%, brown solid).
¹H NMR (500 MHz, DMSO-d₆) δ 13.76 (brs, 1H), 8.27 (d, J=5.0 Hz, 1H), 7.98 (d, J=5.0 Hz, 1H), 7.58-7.46 (m, 5H)

Example 1. 4-ethoxy-N-(3-fluoro-4-{[2-(5-{[(2-methoxyethyl)amino]methyl}pyridin-2-yl)thieno[3,2-b]pyridin-7-yl]oxy}phenyl)-2-oxo-1-phenyl-1,2-dihydropyridine-3-carboxamide hydrochloride Step 1: Synthesis of N-{{6-bromopyridin-3-yl)methyl}-2-methoxyethanamine

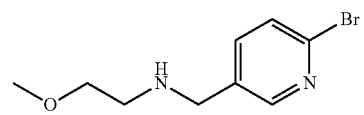

6-bromopyridine-3-carboxaldehyde (5 g, 26.88 mmol) was dissolved in 1,2-dichloroethane, 2-methoxyethylamine (3.5 mL, 40.32 mmol) and acetic acid (1.6 mL, 28.76 mmol) were sequentially added thereto, and the mixture was stirred for 20 minutes. Subsequently, sodium triacetoxy borohydride (8.5 g, 40.32 mmol) was added thereto, and the mixture was stirred at room temperature for 2 hours. The reaction was terminated with 1 N aqueous hydrochloric acid solution, the pH was adjusted to 9 with 2 N aqueous sodium hydroxide solution and the mixture was extracted with dichloromethane. The separated organic layer was dried over anhydrous sodium sulfate, filtered and concentrated under reduced pressure. The resulting residue was purified by column chromatography to obtain the title compound (4.05 g, yield: 70%, light red oil).
¹H NMR (500 MHz, DMSO-d₆) δ 8.31 (d, J=5.0 Hz, 1H), 7.70 (dd, J=10.0 and 5.0 Hz, 1H), 7.58 (d, J=10.0 Hz, 1H), 3.69 (s, 2H), 3.37 (t, J=5.0 Hz, 1H), 3.22 (s, 3H), 2.60 (d, J=5.0 Hz, 2H)

Step 2: Synthesis of t-butyl [(6-bromopyridin-3-yl)methyl](2-methoxyethyl)carbonate

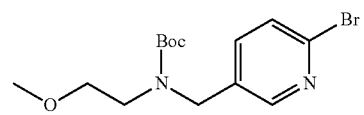 [SMILES: COCCN(Cc1ccc(Br)nc1)C(=O)OC(C)(C)C]

The compound prepared in the above Step 1 (4.05 g, 16.52 mmol) was dissolved in tetrahydrofuran, di-t-butyl dicarbonate (3.9 mL, 17.02 mmol) was added thereto, and the mixture was stirred at room temperature for 30 minutes. The mixture was extracted with ethyl acetate, and the separated organic layer was dried over anhydrous sodium sulfate, filtered and concentrated under reduced pressure. The resulting residue was purified by column chromatography to obtain the title compound (5.52 g, yield: 97%, colorless oil).

$^1$H NMR (500 MHz, DMSO-$d_6$) δ 8.27 (s, 1H), 7.64-7.59 (m, 2H), 4.40 (s, 2H), 3.40 (m, 4H), 3.21 (s, 3H), 1.42-1.31 (m, 9H)

Step 3: Synthesis of t-butyl {[6-(7-chlorothieno[3,2-b]pyridin-2-yl)pyridin-3-yl]methyl}(2-methoxyethyl)carbamate

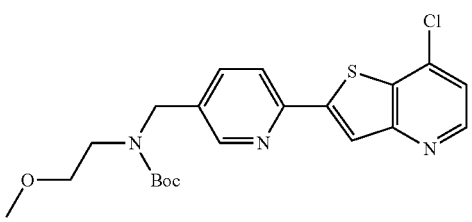 [SMILES: COCCN(Cc1ccc(-c2cc3nccc(Cl)c3s2)nc1)C(=O)OC(C)(C)C]

7-Chlorothieno [3,2-b] pyridine (5.4 g, 31.86 mmol) was dissolved in tetrahydrofuran, 2.5 M n-butyllithium hexane solution (2.7 mL, 31.86 mmol) was slowly added thereto at −78° C., and the mixture was stirred for 30 minutes. 1 M solution of zinc chloride diethyl ether (31.9 mL, 31.86 mmol) was slowly added thereto, and after 10 minutes, the temperature was gradually raised to room temperature, followed by stirring for 1 hour. Sequentially, tetrakis(triphenylphosphine)palladium (920 mg, 0.79 mmol) and the compound prepared in Step 2 (5.5 g, 15.93 mmol) were added to the mixture, which was then refluxed for 2 hours. The mixture was cooled to room temperature and concentrated under reduced pressure. The resulting residue was filtered with acetonitrile and dried to obtain the title compound (5.2 g, yield: 75%, off-white solid).

$^1$H NMR (500 MHz, DMSO-$d_6$) δ 8.66 (d, J=5.0 Hz, 1H), 8.54 (s, 1H), 8.42 (s, 1H), 8.29 (d, J=5.0 Hz, 1H), 7.82 (dd, J=10.0 and 5.0 Hz, 1H), 7.59 (d, J=5.0 Hz, 1H), 4.50 (s, 2H), 3.45-3.36 (m, 4H), 3.23 (s, 3H), 1.45-1.34 (m, 9H)

Step 4: Synthesis of t-butyl {[6-(7-(2-fluoro-4-nitrophenoxy)thieno[3,2-b]pyridin-2-yl]pyridin-3-yl]methyl}(2-methoxyethyl)carbamate

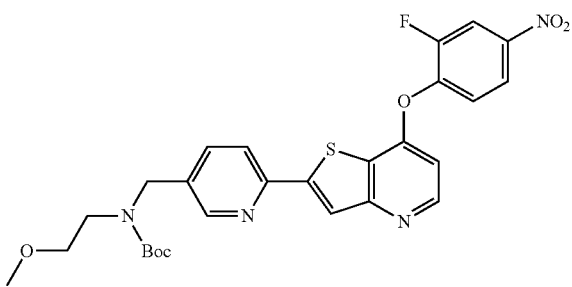 [SMILES: COCCN(Cc1ccc(-c2cc3nccc(Oc4ccc([N+](=O)[O-])cc4F)c3s2)nc1)C(=O)OC(C)(C)C]

The compound prepared in Step 3 (2.0 g, 4.61 mmol) was dissolved in diphenyl ether, anhydrous potassium carbonate (765 mg, 5.53 mmol) and 2-fluoro-4-nitrophenol (1.4 g, 9.22 mmol) were sequentially added thereto, and the mixture was stirred at 160° C. for 5 hours. The mixture was cooled to room temperature and extracted with ethyl acetate. The separated organic layer was dried over anhydrous sodium sulfate, filtered and concentrated under reduced pressure. The residue was dissolved in tetrahydrofuran, di-t-butyl dicarbonate (1.06 mL, 4.61 mmol) was added thereto, and the mixture was stirred at room temperature for 30 minutes. The mixture was concentrated under reduced pressure and the resulting residue was purified by column chromatography to obtain the title compound (1.2 g, yield: 46%, off-white solid).

$^1$H NMR (500 MHz, DMSO-$d_6$) δ 8.62 (d, J=5.0 Hz, 1H), 8.50-8.48 (m, 2H), 8.39 (s, 1H), 8.28 (d, J=5.0 Hz, 1H), 8.21 (d, J=10.0 and 5.0 Hz, 1H), 7.80 (d, J=10.0 Hz, 1H), 7.72 (t, J=10.0 Hz, 1H), 6.98 (d, J=5.0 Hz, 1H), 4.48 (s, 2H), 3.43-3.35 (m, 4H), 3.23 (s, 3H), 1.44-1.33 (m, 9H)

Step 5: Synthesis of t-butyl {[6-[7-(4-amino-2-fluorophenoxy)thieno[3,2-b]pyridin-2-yl]pyridin-3-yl]methyl}(2-methoxyethyl)carbamate

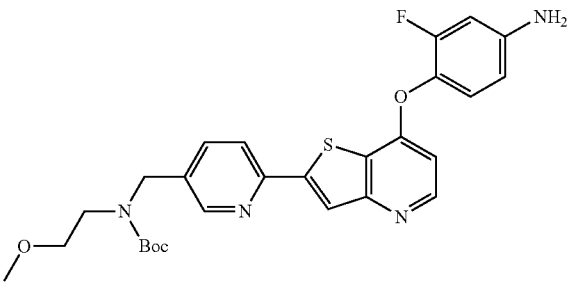

The compound prepared in the above Step 4 (1.2 g, 2.16 mmol) was dissolved in ethanol and water, iron (363 mg, 6.49 mmol) and ammonium chloride (1.16 g, 21.64 mmol) were sequentially added at room temperature, and the mixture was heated to 100° C. and stirred for 3 hours. After completion of the reaction, the reaction mixture was filtered using a celite pad in a warm state, and the filtrate was concentrated under reduced pressure. The residue was extracted with dichloromethane. The separated organic layer was dried over anhydrous sodium sulfate, concentrated under reduced pressure, and then filtered with diethyl ether to obtain the title compound (833 mg, yield: 73%, off-white solid).

$^1$H NMR (500 MHz, DMSO-$d_6$) δ 8.51-8.49 (m, 2H), 8.30 (s, 1H), 8.24 (d, J=5.0 Hz, 1H), 7.78 (dd, J=10.0 and 5.0 Hz, 1H), 7.13 (t, J=10.0 Hz, 1H), 6.60 (d, J=5.0 Hz, 1H), 6.53 (dd, J=15.0 and 5.0 Hz, 1H), 6.45 (dd, J=10.0 and 5.0 Hz, 1H), 5.55 (s, 2H), 4.48 (s, 2H), 3.43-3.33 (m, 4H), 3.23 (s, 3H), 1.44-1.34 (m, 9H)

Step 6: Synthesis of t-butyl [(6-{7-[4-(4-ethoxy-2-oxo-1-phenyl-1,2-dihydropyridine-3-carboxamido)-2-fluorophenoxy]thieno[3,2-b]pyridin-2-yl)pyridin-3-yl)methyl](2-methoxyethyl)carbamate

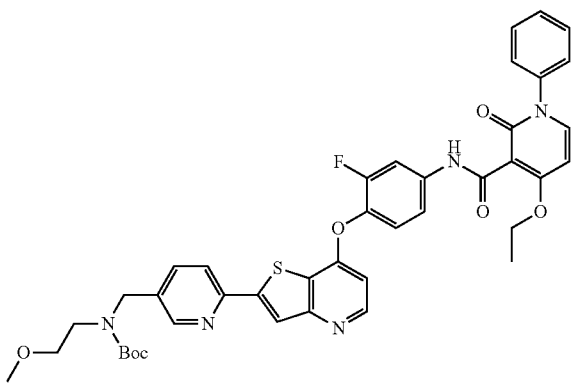 [SMILES: CCOc1ccn(-c2ccccc2)c(=O)c1C(=O)Nc1ccc(Oc2ccnc3cc(-c4ccc(CN(CCOC)C(=O)OC(C)(C)C)cn4)sc23)c(F)c1]

4-Ethoxy-2-oxo-1-phenyl-1,2-dihydropyridine-3-carboxylic acid (0.57 g, 2.2 mmol) of Preparation Example 3, 1-(3-dimethylaminopropyl)-3-ethyl carbodiimide hydrochloride (0.42 g, 2.2 mmol), and hydroxybenzotriazole (0.3 g, 2.2 mmol) were dissolved in dichloromethane, and then triethylamine (0.22 g, 2.2 mmol) and the compound prepared in Step 5 (0.58 g, 1.1 mmol) were sequentially added thereto, and the mixture was stirred at room temperature for 24 hours or more. After terminating the reaction with a saturated aqueous sodium bicarbonate solution, the mixture was extracted with dichloromethane. The separated organic layer was dried over anhydrous magnesium sulfate and concentrated under reduced pressure. The resulting residue was purified by column chromatography to obtain the title compound (0.69 g, yield: 82%, off-white solid).
$^1$H NMR (500 MHz, DMSO-d$_6$) δ 10.64 (brs, 1H), 8.52-8.51 (m, 2H), 8.33 (s, 1H), 7.95 (d, J=10.0 Hz, 1H), 7.87 (d, J=5.0 Hz, 1H), 7.79 (d, J=10.0 Hz, 1H), 7.56-7.40 (m, 8H), 6.71 (d, J=5.0 Hz, 1H), 6.52 (d, J=10.0 Hz, 1H), 4.48 (s, 2H), 4.27 (qt, J=7.5 Hz, 2H), 3.43-3.36 (m, 4H), 3.23 (s, 3H), 1.14-1.30 (m, 12H)

Step 7: Synthesis of 4-ethoxy-N-(3-fluoro-4-{[2-(5-{[(2-methoxyethyl)amino]methyl}pyridin-2-yl)thieno[3,2-b]pyridin-7-yl]oxy}phenyl)-2-oxo-1-phenyl-1,2-dihydropyridine-3-carboxamide Hydrochloride 10 mL of 4 M hydrochloric acid in 1,4-dioxane was added to the compound prepared in the above Step 6 (0.69 g, 0.9 mmol), and the mixture was stirred at room temperature for 1 hour or more. The reaction mixture was concentrated under reduced pressure, dissolved in a small amount of ethanol, and diethyl ether was added thereto. The resulting solid was filtered and dried to obtain the title compound (0.61 g, yield: 96%, off-white solid).
$^1$H NMR (500 MHz, DMSO-d$_6$) δ 10.70 (brs, 1H), 9.50 (brs, 2H), 8.80 (s, 1H), 8.69 (d, J=5.0 Hz, 1H), 8.47 (s, 1H), 8.44 (d, J=5.0 Hz, 1H), 8.22 (dd, J=10.0 and 5.0 Hz, 1H), 7.99 (d, J=10.0 Hz, 1H), 7.88 (d, J=5.0 Hz, 1H), 7.57-7.40 (m, 7H), 6.97 (d, J=5.0 Hz, 1H), 6.53 (d, J=5.0 Hz, 1H), 4.29-4.25 (m, 4H), 3.65 (t, J=5.0 Hz, 2H), 3.31 (s, 3H), 3.16-3.12 (m, 2H), 1.31 (t, J=5.0 Hz, 3H)

Example 2. N-(3-fluoro-4-{[2-(5-{[(2-methoxyethyl)amino]methyl}pyridin-2-yl)thieno[3,2-b]pyridin-7-yl]oxy}phenyl)-1-(4-fluorophenyl)-4-methoxy-2-oxo-1,2-dihydropyridine-3-carboxamide Hydrochloride The synthesis route of Example 1 was repeated except that 1-(4-fluorophenyl)-4-methoxy-2-oxo-1,2-dihydropyridine-3-carboxylic acid of Preparation Example 8 was used as a starting material of Step 6 to obtain the title compound.

Example 3. N-(3-fluoro-4-{[2-(5-{[(2-methoxyethyl)amino]methyl}pyridin-2-yl)thieno[3,2-b]pyridin-7-yl]oxy}phenyl)-4-methoxy-2-oxo-1-phenyl-1,2-dihydropyridine-3-carboxamide Hydrochloride The synthesis route of Example 1 was repeated except that 1-methoxy-2-oxo-1-phenyl-1,2-dihydropyridine-3-carboxylic acid of Preparation Example 10 was used as a starting material of Step 6 to obtain the title compound.

Example 4. N-(3-fluoro-4-{[2-(5-{[(2-methoxyethyl)amino]methyl}pyridin-2-yl)thieno[3,2-b]pyridin-7-yl]oxy}phenyl)-1-(4-fluorophenyl)-2-oxo-1,2-dihydropyridine-3-carboxamide Hydrochloride The synthesis route of Example 1 was repeated except that 1-(4-fluorophenyl)-2-oxo-1,2-dihydropyridine-3-carboxylic acid of Preparation Example 11 was used as a starting material of Step 6 to obtain the title compound.

Example 5. N-(3-fluoro-4-{[2-(5-{[(2-methoxyethyl)amino]methyl}pyridin-2-yl)thieno[3,2-b]pyridin-7-yl]oxy}phenyl)-2-oxo-1-phenyl-1,2-dihydropyridine-3-carboxamide Hydrochloride The synthesis route of Example 1 was repeated except that 2-oxo-1-phenyl-1,2-dihydropyridine-3-carboxylic acid of Preparation Example 12 was used as a starting material of Step 6 to obtain the title compound.

Example 6. t-butyl {[6-(7-{4-[4-ethoxy-1-(4-fluorophenyl)-2-oxo-1,2-dihydropyridine-3-carboxamido]-2-fluorophenoxy}thieno[3,2-b]pyridin-2-yl)pyridin-3-yl]methyl}(2-methoxyethyl)carbamate The synthesis route of Example 1 was repeated except that 4-ethoxy-1-(4-fluorophenyl)-2-oxo-1,2-dihydropyridine-3-carboxylic acid of Preparation Example 1 was used as a starting material of Step 6 and Step 7 was omitted to obtain the title compound.

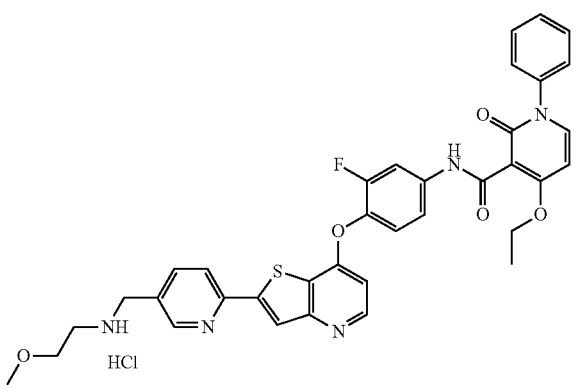 [SMILES: CCOc1ccn(-c2ccccc2)c(=O)c1C(=O)Nc1ccc(Oc2ccnc3cc(-c4ccc(CNCCOC)cn4)sc23)c(F)c1 ; Cl]

Example 7. 4-ethoxy-N-(3-fluoro-4-{[2-(5-{[(2-methoxyethyl)amino]methyl}pyridin-2-yl)thieno[3,2-b]pyridin-7-yl]oxy}phenyl)-1-(4-fluorophenyl)-2-oxo-1,2-dihydropyridine-3-carboxamide Hydrochloride The synthesis route of Example 1 was repeated except that 4-ethoxy-1-(4-fluorophenyl)-2-oxo-1,2-dihydropyridine-3-carboxylic acid of Preparation Example 1 was used as a starting material of Step 6 to obtain the title compound.

Example 8. 1-(4-chlorophenyl)-4-ethoxy-N-(3-fluoro-4-{[2-(5-{[(2-methoxyethyl)amino]methyl}pyridin-2-yl)thieno[3,2-b]pyridin-7-yl]oxy}phenyl)-2-oxo-1,2-dihydropyridine-3-carboxamide Hydrochloride The synthesis route of Example 1 was repeated except that 4-ethoxy-1-(4-chlorophenyl)-2-oxo-1,2-dihydropyridine-3-carboxylic acid of Preparation Example 4 was used as a starting material of Step 6 to obtain the title compound.

Example 9. N-(3-chloro-4-{[2-(5-{[(2-methoxyethyl)amino]methyl}pyridin-2-yl)thieno[3,2-b]pyridin-7-yl]oxy}phenyl)-1-(4-fluorophenyl)-4-methoxy-2-oxo-1,2-dihydropyridine-3-carboxamide Hydrochloride The synthesis route of Example 2 was repeated except that 2-chloro-4-nitrophenol was used instead of 2-fluoro-4-nitrophenol in Step 4 to obtain the title compound.

Example 10. N-(2-chlor-4-{[-2-(5-{[(2-methoxyethyl)amino]methyl}pyridin-2-yl)thieno[3,2-b]pyridin-7-yl]oxy}phenyl)-1-(4-fluorophenyl)-4-methoxy-2-oxo-1,2-dihydropyridine-3-carboxamide Hydrochloride The synthesis route of Example 2 was repeated except that 3-chloro-4-nitrophenol was used instead of 2-fluoro-4-nitrophenol in Step 4 to obtain the title compound.

Example 11. 1-(4-fluorophenyl)-4-methoxy-N-(4-{[2-(5-{[(2-methoxyethyl)amino]methyl}pyridin-2-yl)thieno[3,2-b]pyridin-7-yl]oxy)phenyl)-2-oxo-1,2-dihydropyridine-3-carboxamide Hydrochloride The synthesis route of Example 2 was repeated except that 4-nitrophenol was used instead of 2-fluoro-4-nitrophenol in Step 4 to obtain the title compound.

Example 12. 4-ethoxy-N-(3-fluoro-4-{[2-(5-{[(2-methoxyethyl)amino]methyl}pyridin-2-yl)thieno[3,2-b]pyridin-7-yl]oxy}phenyl)-2-oxo-1-(4-(trifluoromethyl)phenyl)-1,2-dihydropyridine-3-carboxamide Hydrochloride The synthesis route of Example 1 was repeated except that 4-ethoxy-2-oxo-1-[4-(trifluoromethyl)phenyl]-1,2-dihydropyridine-3-carboxylic acid of Preparation Example 5 was used as a starting material of Step 6 to obtain the title compound.

Example 13. 1-(4-chlorophenyl)-N-(3-fluoro-4-{[2-(5-{[(2-methoxyethyl)amino]methyl}pyridin-2-yl)thieno[3,2-b]pyridin-7-yl]oxy}phenyl)-4-methoxy-2-oxo-1,2-dihydropyridine-3-carboxamide Hydrochloride The synthesis route of Example 1 was repeated except that 4-methoxy-1-(4-chlorophenyl)-2-oxo-1,2-dihydropyridine-3-carboxylic acid of Preparation Example 9 was used as a starting material of Step 6 to obtain the title compound.

Example 14. 4-ethoxy-N-(3-fluoro-4-{[2-(5-{[(2-methoxyethyl)amino]methyl}pyridin-2-yl)thieno[3,2-b]pyridin-7-yl]oxy}phenyl)-1-(3-fluorophenyl)-2-oxo-1,2-dihydropyridine-3-carboxamide Hydrochloride The synthesis route of Example 1 was repeated except that 4-ethoxy-1-(3-fluorophenyl)-2-oxo-1,2-dihydropyridine-3-carboxylic acid of Preparation Example 2 was used as a starting material of Step 6 to obtain the title compound.

Example 15. 4-ethoxy-N-(3-fluoro-4-{[2-(5-{[(2-methoxyethyl)amino]methyl}pyridin-2-yl)thieno[3,2-b]pyridin-7-yl]oxy}phenyl)-1-(4-methoxyphenyl)-2-oxo-1,2-dihydropyridine-3-carboxamide Hydrochloride The synthesis route of Example 1 was repeated except that 4-ethoxy-1-(4-methoxyphenyl)-2-oxo-1,2-dihydropyridine-3-carboxylic acid of Preparation Example 6 was used as a starting material of Step 6 to obtain the title compound.

Example 16. 4-ethoxy-N-(3-fluoro-4-{[2-(5-{[(2-methoxyethyl)amino]methyl}pyridin-2-yl)thieno[3,2-b]pyridin-7-yl]oxy}phenyl)-1-(3-methoxyphenyl)-2-oxo-1,2-dihydropyridine-3-carboxamide Hydrochloride The synthesis route of Example 1 was repeated except that 4-ethoxy-1-(3-methoxyphenyl)-2-oxo-1,2-dihydropyridine-3-carboxylic acid of Preparation Example 7 was used as a starting material of Step 6 to obtain the title compound.

Example 17. N-(3-fluoro-4-{[2-(5-{[(2-methoxyethyl)amino]methyl}pyridin-2-yl)thieno[3,2-b]pyridin-7-yl]oxy}phenyl)-2-(4-fluorophenyl)-5-methyl-3-oxo-2,3-dihydropyridazine-4-carboxamide Hydrochloride The synthesis route of Example 1 was repeated except that 2-(4-fluorophenyl)-5-methyl-3-oxo-2,3-dihydropyridazine-4-carboxylic acid of Preparation Example 22 was used as a starting material of Step 6 to obtain the title compound.

Example 18. N-(3-fluoro-4-{[2-(5-{[(2-methoxyethyl)amino]methyl}pyridin-2-yl)thieno[3,2-b]pyridin-7-yl]oxy}phenyl)-5-methyl-3-oxo-2-phenyl-2,3-dihydropyridazine-4-carboxamide Hydrochloride The synthesis route of Example 1 was repeated except that 5-methyl-3-oxo-2-phenyl-2,3-dihydropyridazine-4-carboxylic acid of Preparation Example 23 was used as a starting material of Step 6 to obtain the title compound.

Example 19. N-(3-fluoro-4-{[2-(5-{[(2-methoxyethyl)amino]methyl}pyridin-2-yl)thieno[3,2-b]pyridin-7-yl]oxy}phenyl)-3-oxo-2-phenyl-2,3-dihydropyridazine-4-carboxamide Hydrochloride The synthesis route of Example 1 was repeated except that 3-oxo-2-phenyl-2,3-dihydropyridazine-4-carboxylic acid of Preparation Example 24 was used as a starting material of Step 6 to obtain the title compound.

Example 20. N-(3-fluoro-4-[{2-(5-[{(2-methoxyethyl)amino}methyl]pyridin-2-yl)thieno[3,2-b]pyridin-7-yl}oxy]phenyl)-2-(4-fluorophenyl)-3-oxo-2,3-dihydropyridazine-4-carboxamide Hydrochloride The synthesis route of Example 1 was repeated except that 2-(4-fluorophenyl)-3-oxo-2,3-dihydropyridazine-4-carboxylic acid of Preparation Example 21 was used as a starting material of Step 6 to obtain the title compound.

Example 21. N-(3-fluoro-4-{[2-(5-{[(2-methoxyethyl)amino]methyl}pyridin-2-yl)thieno[3,2-b]pyridin-7-yl]oxy}phenyl)-6-methyl-2-oxo-1-phenyl-1,2-dihydropyridine-3-carboxamide Hydrochloride The synthesis route of Example 1 was repeated except that 6-methyl-2-oxo-1-phenyl-1,2-dihydropyridine-3-carboxylic acid of Preparation Example 13 was used as a starting material of Step 6 to obtain the title compound.

Example 22. N-(3-fluoro-4-{[2-(5-{[(2-methoxyethyl)amino]methyl}pyridin-2-yl)thieno[3,2-b]pyridin-7-yl]oxy}phenyl)-1-(4-fluorophenyl)-6-methyl-2-oxo-1,2-dihydropyridine-3-carboxamide Hydrochloride The synthesis route of Example 1 was repeated except that 6-methyl-2-oxo-1-(4-fluorophenyl)-1,2-dihydropyridine-3-carboxylic acid of Preparation Example 14 was used as a starting material of Step 6 to obtain the title compound.

Example 23. 5-bromo-N-(3-fluoro-4-{[2-(5-1 [(2-methoxyethyl)amino]methyl}pyridin-2-yl)thieno[3,2-b]pyridin-7-yl]oxy}phenyl)-1-(4-fluorophenyl)-2-oxo-1,2-dihydropyridine-3-carboxamide Hydrochloride The synthesis route of Example 1 was repeated except that 5-bromo-1-(4-fluorophenyl)-2-oxo-1,2-dihydropyridine-3-carboxylic acid of Preparation Example 15 was used as a starting material of Step 6 to obtain the title compound.

Example 24. 5-chloro-N-(3-fluoro-4-{[2-(5-{[(2-methoxyethyl)amino]methyl}pyridin-2-yl)thieno[3,2-b]pyridin-7-yl]oxy}phenyl)-1-(4-fluorophenyl)-2-oxo-1,2-dihydropyridine-3-carboxamide Hydrochloride The synthesis route of Example 1 was repeated except that 5-chloro-1-(4-fluorophenyl)-2-oxo-1,2-dihydropyridine-3-carboxylic acid of Preparation Example 16 was used as a starting material of Step 6 to obtain the title compound.

Example 25. N-(3-fluoro-4-{[2-(5-{[(2-methoxyethyl)amino]methyl}pyridin-2-yl)thieno[3,2-b]pyridin-7-yl]oxy}phenyl)-1-(4-fluorophenyl)-4-methyl-2-oxo-1,2-dihydropyridine-3-carboxamide Hydrochloride The synthesis route of Example 7 was repeated except that 4-methyl-2-oxo-1-(4-fluorophenyl)-1,2-dihydropyridine-3-carboxylic acid of Preparation Example 17 was used as a starting material of Step 6 to obtain the title compound.

Example 26. N-(2-chloro-4-{[2-(5-{[(2-methoxyethyl)amino]methyl}pyridin-2-yl)thieno[3,2-b]pyridin-7-yl]oxy}phenyl)-4-ethoxy-1-(4-fluorophenyl)-2-oxo-1,2-dihydropyridine-3-carboxamide Hydrochloride The synthesis route of Example 7 was repeated except that 3-chloro-4-nitrophenol was used instead of 2-fluoro-4-nitrophenol in Step 4 to obtain the title compound.

Example 27. N-(3-fluoro-4-([2-(5-{[(2-methoxyethyl)amino)methyl]pyridin-2-yl}thieno[3,2-b]pyridin-7-yl)oxy]phenyl}-1-(4-fluorophenyl)-5,6-dimethyl-2-oxo-1,2-dihydropyridine-3-carboxamide Hydrochloride The synthesis route of Example 1 was repeated except that 1-(4-fluorophenyl)-5,6-dimethyl-2-oxo-1,2-dihydropyridine-3-carboxylic acid of Preparation Example 20 was used as a starting material of Step 6 to obtain the title compound.

Example 28. N-(3-fluoro-4-{[-2-(5-{[(2-methoxyethyl)amino]methyl}pyridin-2-yl)thieno[3,2-b]pyridin-7-yl]oxy}phenyl)-4-methyl-2-oxo-1-phenyl-1,2-dihydropyridine-3-carboxamide Hydrochloride The synthesis route of Example 1 was repeated except that 4-methyl-2-oxo-1-phenyl-1,2-dihydropyridine-3-carboxylic acid of Preparation Example 18 was used as a starting material of Step 6 to obtain the title compound.

Example 29. N-(3-fluoro-4-{[-2-(5-{[(2-methoxyethyl)amino]methyl}pyridin-2-yl)thieno[3,2-b]pyridin-7-yl]oxy}phenyl)-1-(4-fluorophenyl)-5-methyl-2-oxo-1,2-dihydropyridine-3-carboxamide Hydrochloride The synthesis route of Example 1 was repeated except that 5-methyl-2-oxo-1-(4-fluorophenyl)-1,2-dihydropyridine-3-carboxylic acid of Preparation Example 19 was used as a starting material of Step 6 to obtain the title compound.

The chemical structures, yields and NMR spectrum data of the compounds of the above Examples 2 to 29 are summarized in Table 1 below.

TABLE 1
| Ex. | Chemical structure | Yield | $^1$H NMR spectrum data |
|---|---|---|---|
| 2 | 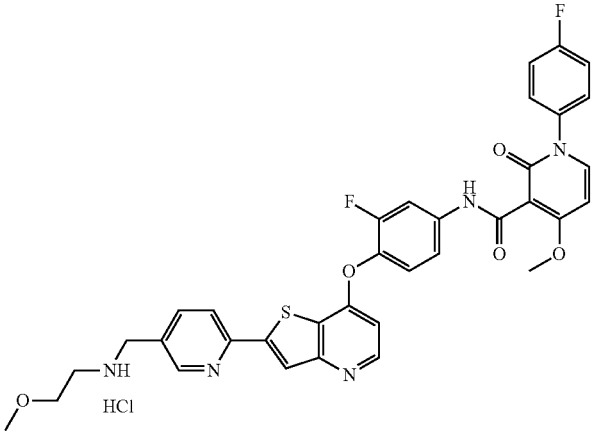 [SMILES: COCCNCc1ccc(-c2cc3nccc(Oc4ccc(NC(=O)c5c(OC)ccn(-c6ccc(F)cc6)c5=O)cc4F)c3s2)nc1 ; Cl] | 90.9% | $^1$H NMR (500 MHz, DMSO-d$_6$) δ 10.72 (brs, 1H), 9.31 (brs, 2H), 8.78 (s, 1H), 8.62 (d, J = 5.0 Hz, 1H), 8.46 (s, 1H), 8.41 (d, J = 5.0 Hz, 1H), 8.18-8.16 (m, 1H), 7.99-7.97 (m, 1H), 7.93 (d, J = 10.0 Hz, 1H), 7.53-7.39 (m, 6H), 6.85 (d, J = 5.0 Hz, 1H), 6.57 (d, J = 5.0 Hz, 1H), 4.28 (t, J = 5.0 Hz, 2H), 3.95 (s, 3H) 3.65 (t, J = 5.0 Hz, 2H), 3.33 (s, 3H), 3.19-3.15 (m, 2H) |
| 3 | 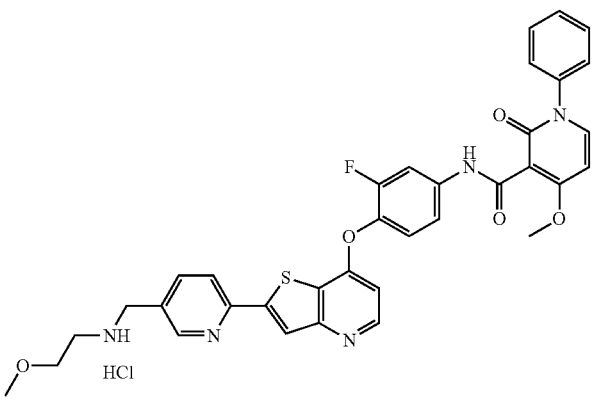 [SMILES: COCCNCc1ccc(-c2cc3nccc(Oc4ccc(NC(=O)c5c(OC)ccn(-c6ccccc6)c5=O)cc4F)c3s2)nc1 ; Cl] | 32.5% | $^1$H NMR (500 MHz, DMSO-d$_6$) δ 10.74 (brs, 1H), 9.37 (brs, 2H), 8.79 (s, 1H), 8.64 (d, J = 5.0 Hz, 1H), 8.46 (s, 1H), 8.42 (d, J = 10.0 Hz, 1H), 8.19 (dd, J = 10.0 and 5.0 Hz, 1H), 8.00-7.98 (m, 1H), 7.93 (d, J = 10.0 Hz, 1H), 7.58-7.42 (m, 7H), 6.88 (d, J = 5.0 Hz, 1H), 6.56 (d, J = 10.0 Hz, 1H), 4.28 (t, J = 5.0 Hz, 2H), 3.95 (s, 3H) 3.65 (t, J = 5.0 Hz, 2H), 3.33 (s, 3H), 3.18-3.15 (m, 2H) |
| 4 | 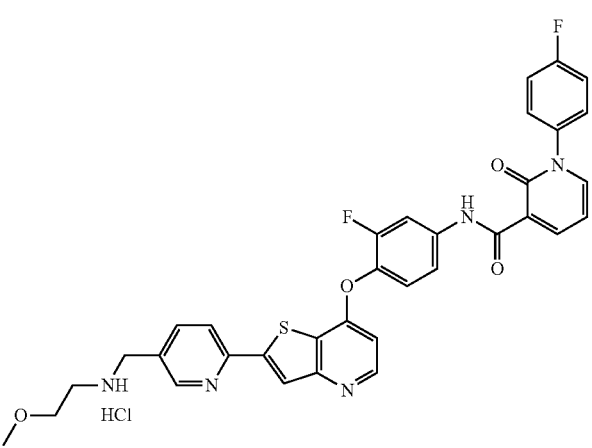 [SMILES: COCCNCc1ccc(-c2cc3nccc(Oc4ccc(NC(=O)c5cccn(-c6ccc(F)cc6)c5=O)cc4F)c3s2)nc1 ; Cl] | 5.8% | $^1$H NMR (500 MHz, DMSO-d$_6$) δ 12.18 (brs, 1H), 9.35 (brs, 2H), 8.78 (s, 1H), 8.64-8.60 (m, 2H), 8.46 (s, 1H), 8.41 (d, J = 10.0 Hz, 1H), 8.19-8.09 (m, 3H), 7.65-7.43 (m, 6H), 6.84 (d, J = 5.0 Hz, 1H), 6.76 (t, J = 5.0 Hz, 1H), 4.28 (t, J = 5.0 Hz, 2H), 3.65 (t, J = 5.0 Hz, 2H), 3.33 (s, 3H), 3.18-3.15 (m, 2H) |

TABLE 1-continued
| Ex. | Chemical structure | Yield | ¹H NMR spectrum data |
|---|---|---|---|
| 5 | 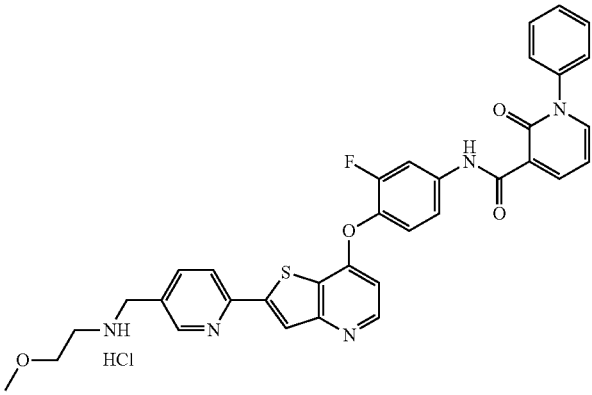 [SMILES: COCCNCc1ccc(-c2cc3nccc(Oc4ccc(NC(=O)c5cccn(-c6ccccc6)c5=O)cc4F)c3s2)nc1 ; Cl] | 39.6% | ¹H NMR (500 MHz, DMSO-$d_6$) δ 12.23 (brs, 1H), 9.44 (brs, 2H), 8.80 (d, J = 10.0 Hz, 1H), 8.67 (d, J = 5.0 Hz, 1H), 8.63-8.61 (m, 1H), 8.47 (s, 1H), 8.43 (d, J = 10.0 Hz, 1H), 8.22-8.10 (m, 3H), 7.59-7.55 (m, 7H), 6.89 (d, J = 5.0 Hz, 1H), 6.76 (t, J = 5.0 Hz, 1H), 4.28 (t, J = 5.0 Hz, 2H), 3.66 (t, J = 5.0 Hz, 2H), 3.33 (s, 3H), 3.18-3.15 (m, 2H) |
| 6 | 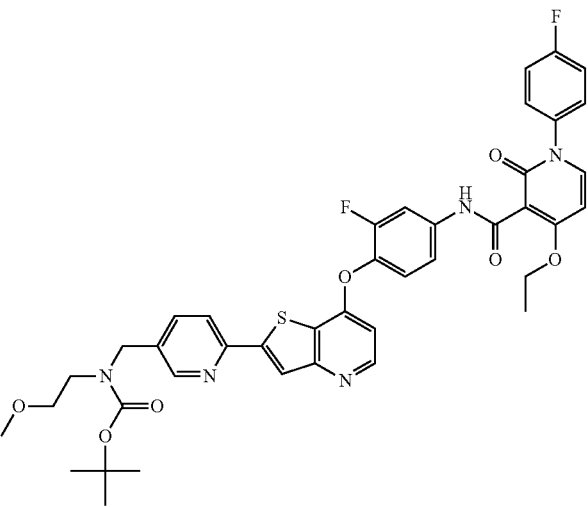 [SMILES: CCOc1ccn(-c2ccc(F)cc2)c(=O)c1C(=O)Nc1ccc(Oc2ccnc3cc(-c4ccc(CN(CCOC)C(=O)OC(C)(C)C)cn4)sc23)c(F)c1] | 72.1% | ¹H NMR (500 MHz, DMSO-$d_6$) δ 10.64 (br s, 1H), 8.52-8.51 (m, 2H), 8.33 (s, 1H), 7.95 (d, J = 10.0 Hz, 1H), 7.87 (d, J = 10.0 Hz, 1H), 7.79 (d, J = 10..0, 1H), 7.50-7.35 (m, 7H), 6.71 (d, J = 5.0 Hz, 1H), 6.53 (d, J = 5.0 Hz, 1H), 4.48 (s, 2H), 4.27 (qt, J = 7.5 Hz, 2H), 3.43-3.36 (m, 4H), 3.23 (s, 3H), 1.44-1.29 (m, 12H) |
| 7 | 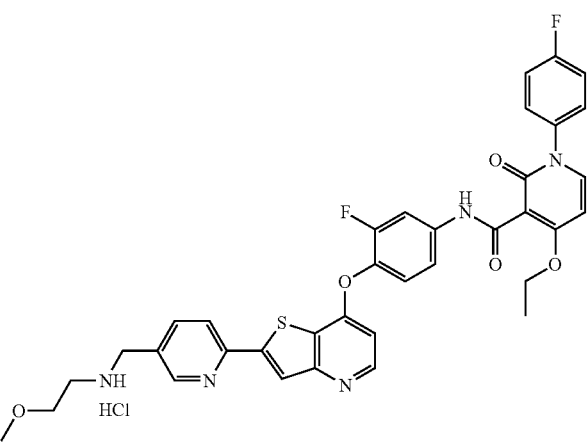 [SMILES: CCOc1ccn(-c2ccc(F)cc2)c(=O)c1C(=O)Nc1ccc(Oc2ccnc3cc(-c4ccc(CNCCOC)cn4)sc23)c(F)c1 ; Cl] | 52.8% | ¹H NMR (500 MHz, DMSO-$d_6$) δ 10.67 (br s, 1H), 9.32 (br s, 2H), 8.78 (s, 1H), 8.62 (d, J = 5.0Hz, 1H), 8.46 (s, 1H), 8.41 (d, J = 10.0 Hz, 1H), 8.18 (d, J = 5.0 Hz, 1H), 7.99-7.96 (m, 1H), 7.90-7.88 (d, J = 10.0 Hz, 1H), 7.53-7.39 (m, 6H), 6.86 (d, J = 5.0 Hz, 1H), 6.55 (d, J = 5.0 Hz, 1H), 4.30-4.26 (m, 4H), 3.64 (m, 2H), 3.33 (s, 3H), 3.19-3.14 (m, 2H), 1.32 (t, J = 5.0 Hz, 3H) |

TABLE 1-continued

| Ex. | Chemical structure | Yield | ¹H NMR spectrum data |
|---|---|---|---|
| 8 | 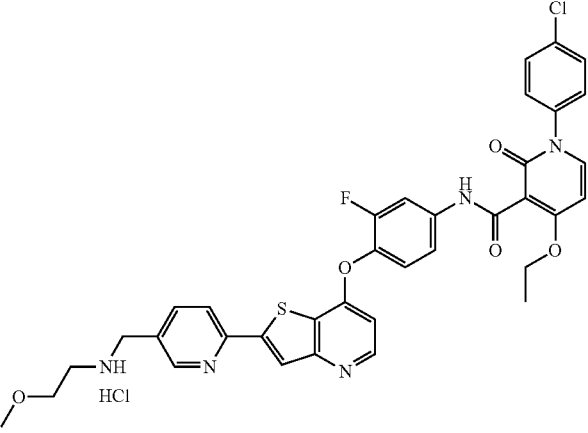 | 81.0% | ¹H NMR (500 MHz, DMSO-d$_6$) δ 10.70 (brs, 1H), 9.54 (brs, 2H), 8.82 (s, 1H), 8.69 (d, J = 10.0 Hz, 1H), 8.48 (s, 1H), 8.44 (d, J = 10.0 Hz, 1H), 8.24 (dd, J = 10.0 and 5.0 Hz, 1H), 8.01-7.98 (m, 1H), 7.90 (d, J = 10.0 Hz, 1H), 7.64-7.46 (m, 6H), 6.97 (d, J = 5.0 Hz, 1H), 6.57 (d, J = 5.0 Hz, 1H), 4.31-4.27 (m, 4H), 3.67 (t, J = 5.0 Hz, 2H), 3.33 (s, 3H), 3.18-3.15 (m, 2H), 1.32 (t, J = 5.0 Hz, 3H) |
| 9 | 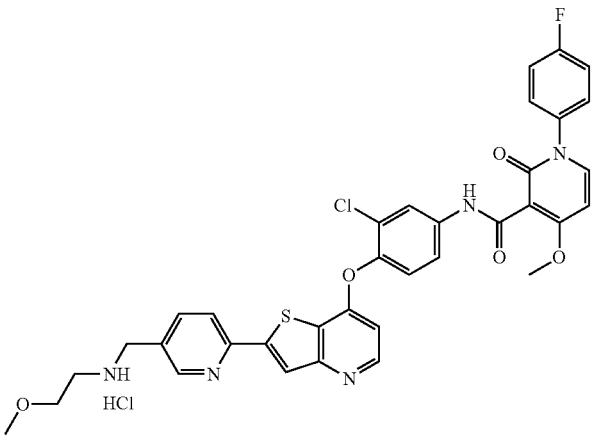 [SMILES: COCCNCc1ccc(-c2cc3nccc(Oc4ccc(NC(=O)c5c(OC)ccn(-c6ccc(F)cc6)c5=O)cc4Cl)c3s2)nc1 ; Cl] | 88.6% | ¹H NMR (500 MHz, DMSO-d$_6$) δ 10.72 (brs, 1H), 9.44 (brs, 2H), 8.79 (s, 1H), 8.65 (d, J = 5.0 Hz, 1H), 8.45 (s, 1H), 8.42 (d, J = 10.0 Hz, 1H), 8.21-8.17 (m, 2H), 7.92 (d, J = 10.0 Hz, 1H), 7.70 (dd, J = 10.0 and 5.0 Hz, 1H), 7.54 (d, J = 10.0 Hz, 1H), 7.49-7.36 (m, 4H), 6.84 (d, J = 5.0 Hz, 1H), 6.56 (d, J = 5.0 Hz, 1H), 4.27 (t, J = 5.0 Hz, 2H), 3.94 (s, 3H), 3.65 (t, J = 5.0 Hz, 2H), 3.31 (s, 3H), 3.16-3.12 (m, 2H) |
| 10 | 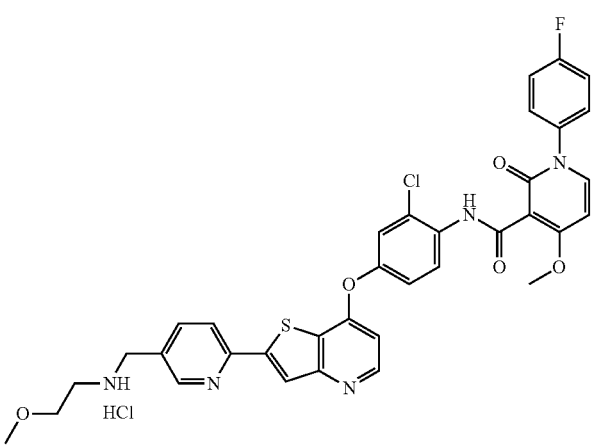 [SMILES: COCCNCc1ccc(-c2cc3nccc(Oc4ccc(NC(=O)c5c(OC)ccn(-c6ccc(F)cc6)c5=O)c(Cl)c4)c3s2)nc1 ; Cl] | 19.7% | ¹H NMR (500 MHz, DMSO-d$_6$) δ 11.33 (s, 1H), 9.39 (brs, 2H), 8.77 (s, 1H), 8.65 (d, J = 5.0 Hz, 1H), 8.45 (s, 1H), 8.42-8.40 (m, 2H), 8.18 (d, J = 10.0 Hz, 1H), 8.01 (d, J = 5.0 Hz, 1H), 7.63 (s, 1H), 7.54-7.51 (m, 2H), 7.42-7.35 (m, 3H), 6.91 (d, J = 10.0 Hz, 1H), 6.62 (d, J = 10.0 Hz, 1H), 4.26 (t, J = 5.0 Hz, 2H), 3.99 (s, 3H) 3.64-3.63 (m, 2H), 3.31 (s, 3H), 3.15-3.13 (m, 2H) |

TABLE 1-continued

| Ex. | Chemical structure | Yield | ¹H NMR spectrum data |
|---|---|---|---|
| 11 | 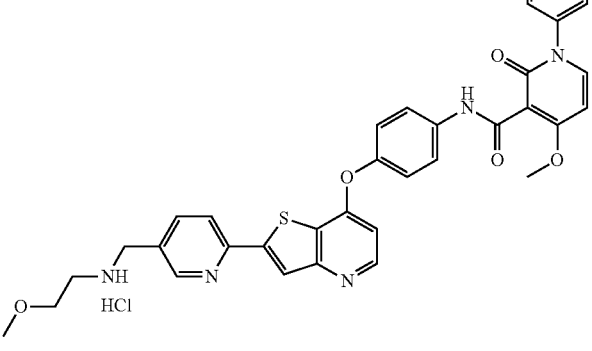 | 60.3% | ¹H NMR (500 MHz, DMSO-d$_6$) δ 10.52 (brs, 1H), 9.44 (brs, 2H), 8.80-8.78 (m, 1H), 8.69-8.68 (m, 1H), 8.46-8.42 (m, 2H), 8.21-7.81 (m, 4H), 7.57-7.34 (m, 5H), 6.91 (t, J = 5.0 Hz, 1H), 6.55 (d, J = 5.0 Hz, 1H), 6.35 (d, J = 5.0 Hz, 1H), 4.27 (t, J = 5.0 Hz, 2H), 3.93 (s, 3H), 3.65 (t, J = 5.0 Hz, 2H), 3.31 (s, 3H), 3.16-3.12 (m, 2H) |
| 12 | 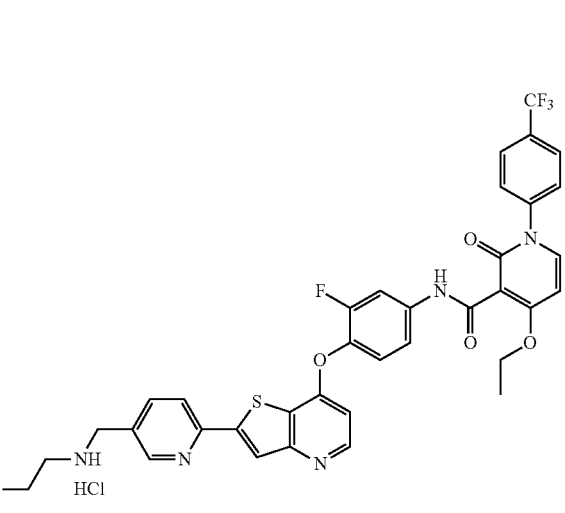 | 92.3% | ¹H NMR (500 MHz, DMSO-d$_6$) δ 10.66 (brs, 1H), 9.25 (brs, 2H), 8.76 (d, J = 5.0 Hz, 1H), 8.59 (d, J = 5.0 Hz, 1H), 8.44 (s, 1H), 8.39 (d, J = 10.0 Hz, 1H), 8.14 (d, J = 10.0 Hz, 1H), 7.97-7.92 (4H, m), 7.69 (d, J = 10.0 Hz, 2H), 7.51 (m, 2H), 6.81 (d, J = 5.0 Hz, 1H), 6.60 (d, J = 5.0 Hz, 1H), 4.31-4.26 (m, 4H), 3.63 (t, J = 5.0 Hz, 2H), 3.32 (s, 3H), 3.18-3.13 (m, 2H), 1.31 (t, J = 5.0 Hz, 3H) |
| 13 | 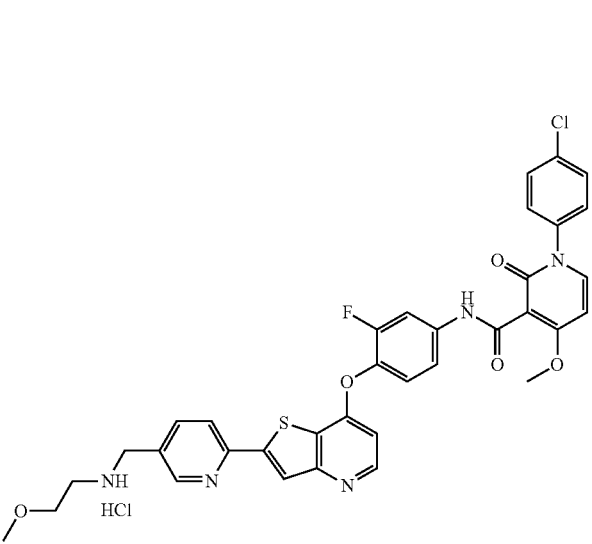 | 6.7% | ¹H NMR (500 MHz, DMSO-d$_6$) δ 10.70 (s, 1H), 9.26 (brs, 2H), 8.76 (s, 1H), 8.58 (d, J = 5.0 Hz, 1H), 8.44 (s, 1H), 8.39 (d, J = 10.0 Hz, 1H), 8.14 (dd, J = 10.0 Hz and 5.0 Hz, 1H), 7.97 (d, J = 15.0 Hz, 1H), 7.92 (d, J = 5.0 Hz, 1H), 7.62-7.60 (m, 2H), 7.51-7.45 (m, 4H), 6.81 (d, J = 5.0 Hz, 1H), 6.57 (d, J = 10.0 Hz, 1H), 4.27 (t, J = 5.0 Hz, 2H), 3.94 (s, 3H), 3.63 (t, J = 5.0 Hz, 2H), 3.32 (s, 3H), 3.17-3.13 (m, 2H) |

TABLE 1-continued

| Ex. | Chemical structure | Yield | $^1$H NMR spectrum data |
|---|---|---|---|
| 14 | 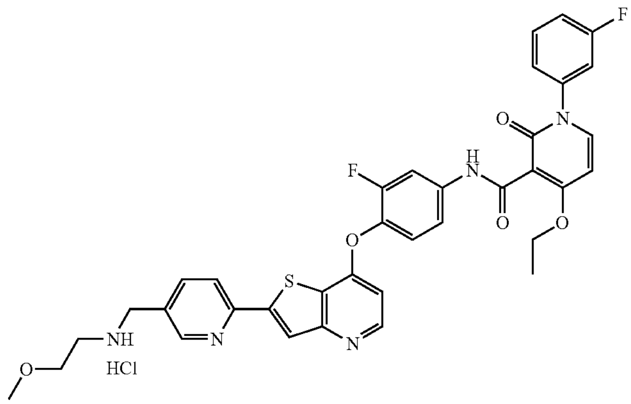 [SMILES: CCOc1ccn(-c2cccc(F)c2)c(=O)c1C(=O)Nc1ccc(Oc2ccnc3cc(-c4ccc(CNCCOC)cn4)sc23)c(F)c1 ; Cl] | 73.5% | $^1$H NMR (500 MHz, DMSO-d$_6$) δ 10.70 (s, 1H), 9.47 (brs, 2H), 8.79 (s, 1H), 8.66 (d, J = 5.0 Hz, 1H), 8.46 (s, 1H), 8.43 (d, J = 10.0 Hz, 1H), 8.21 (dd, J = 10.0 Hz and 5.0 Hz, 1H), 7.98 (d, J = 15.0 Hz, 1H), 7.91 (d, J = 10.0 Hz, 1H), 7.61-7.53 (m, 3H), 7.39-7.33 (m, 2H), 7.28 (d, J = 10.0 Hz, 1H), 6.93 (d, J = 5.0 Hz, 1H), 6.55 (d, J = 5.0 Hz, 1H), 4.30-4.26 (m, 4H), 3.65 (t, J = 5.0 Hz, 2H), 3.31 (s, 3H), 3.16-3.12 (m, 2H), 1.30 (t, J = 5.0 Hz, 3H) |
| 15 | 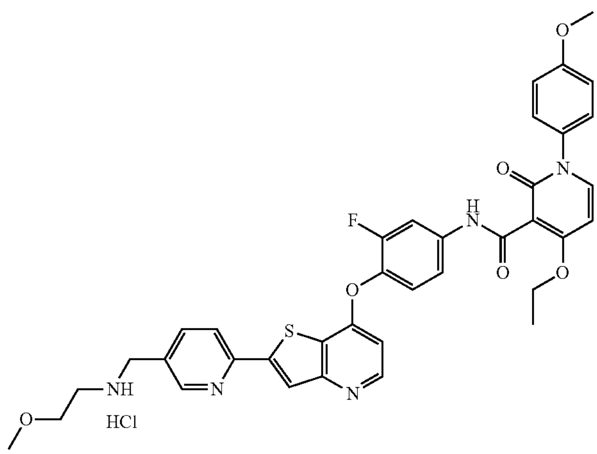 | 74.8% | $^1$H NMR (500 MHz, DMSO-d$_6$) δ 10.67 (s, 1H), 9.32 (brs, 2H), 8.77 (s, 1H), 8.61 (d, J = 10.0 Hz, 1H), 8.45 (s, 1H), 8.40 (d, J = 10.0 Hz, 1H), 8.16 (dd, J = 10.0 Hz and 5.0 Hz, 1H), 7.98-7.95 (m, 1H), 7.83 (d, J = 10.0 Hz, 1H), 7.52-7.51 (m, 2H), 7.33-7.31 (m, 2H), 7.07-7.05 (m, 2H), 6.84 (d, J = 5.0 Hz, 1H), 6.49 (d, J = 10.0 Hz, 1H), 4.29-4.24 (m, 4H), 3.81 (s, 3H), 3.63 (t, J = 5.0 Hz, 2H), 3.32 (s, 3H), 3.17-3.13 (m, 2H), 1.30 (t, J = 5.0 Hz, 3H) |
| 16 | 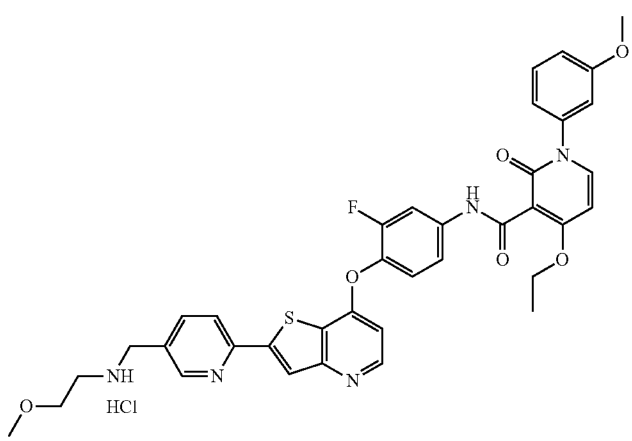 | 79.9% | $^1$H NMR (500 MHz, DMSO-d$_6$) δ 10.67 (s, 1H), 9.31 (brs, 2H), 8.77 (s, 1H), 8.61 (d, J = 5.0 Hz, 1H), 8.45 (s, 1H), 8.40 (d, J = 10.0 Hz, 1H), 8.16 (d, J = 10.0 Hz, 1H), 7.97 (d, J = 15.0 Hz, 1H), 7.86 (d, J = 10.0 Hz, 1H), 7.52-7.51 (m, 2H), 7.44 (t, J = 10.0 Hz, 1H), 7.05 (d, J = 10.0 Hz, 1H), 6.97-6.96 (m, 2H), 6.85 (d, J = 10.0 Hz, 1H), 6.51 (d, J = 5.0 Hz, 1H), 4.29-4.24 (m, 4H), 3.80 (s, 3H), 3.63 (t, J = 5.0 Hz, 2H), 3.32 (s, 3H), 3.17-3.13 (m, 2H), 1.31 (t, J = 5.0 Hz, 3H) |

TABLE 1-continued

| Ex. | Chemical structure | Yield | ¹H NMR spectrum data |
|---|---|---|---|
| 17 | 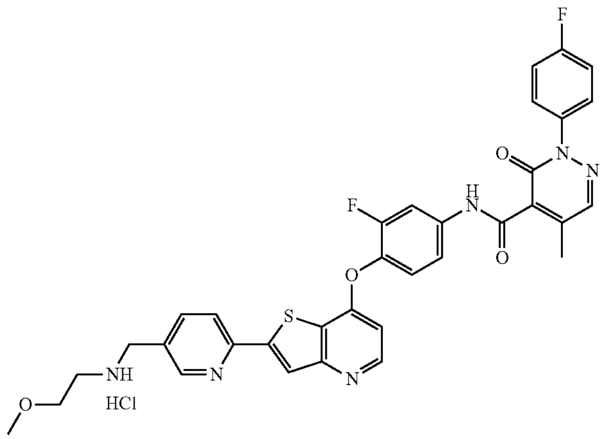 [SMILES: COCCNCc1ccc(-c2cc3nccc(Oc4ccc(NC(=O)c5c(C)cnn(-c6ccc(F)cc6)c5=O)cc4F)c3s2)nc1 ; Cl] | 45.2% | ¹H NMR (500 MHz, DMSO-$d_6$) δ 11.87 (brs, 1H), 9.39 (brs, 2H), 8.77 (s, 1H), 8.64 (d, J = 5.0 Hz, 1H), 8.46 (s, 1H), 8.41 (d, J = 10.0 Hz, 1H), 8.24 (s, 1H), 8.18 (d, J = 10.0 Hz, 1H), 8.08 (d, J = 10.0 Hz, 1H), 7.67-7.57 (m, 4H), 7.42-7.38 (m, 2H), 6.86 (d, J = 10.0 Hz, 1H), 4.27 (t, J = 5.0 Hz, 2H), 3.62 (m, 2H), 3.32 (s, 3H), 3.17-3.13 (m, 2H), 2.47 (s, 3H) |
| 18 | 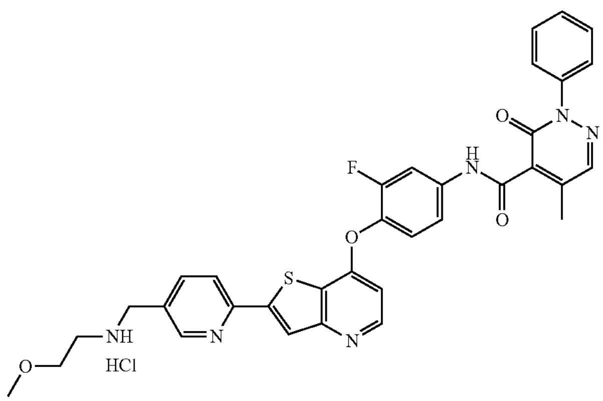 [SMILES: COCCNCc1ccc(-c2cc3nccc(Oc4ccc(NC(=O)c5c(C)cnn(-c6ccccc6)c5=O)cc4F)c3s2)nc1 ; Cl] | 67.3% | ¹H NMR (500 MHz, DMSO-$d_6$) δ 11.91 (brs, 1H), 9.39 (brs, 2H), 8.77 (s, 1H), 8.64 (d, J = 5.0 Hz, 1H), 8.46 (s, 1H), 8.41 (d, J = 10.0 Hz, 1H), 8.24 (s, 1H), 8.18 (d, J = 5.0 Hz, 1H), 8.08 (d, J = 10.0 Hz, 1H), 7.64-7.48 (m, 7H), 6.86 (d, J = 10.0 Hz, 1H), 4.27 (t, J = 5.0 Hz, 2H), 3.64 (t, J = 5.0 Hz, 2H), 3.32 (s, 3H), 3.17-3.12 (m, 2H), 2.47 (s, 3H) |
| 19 | 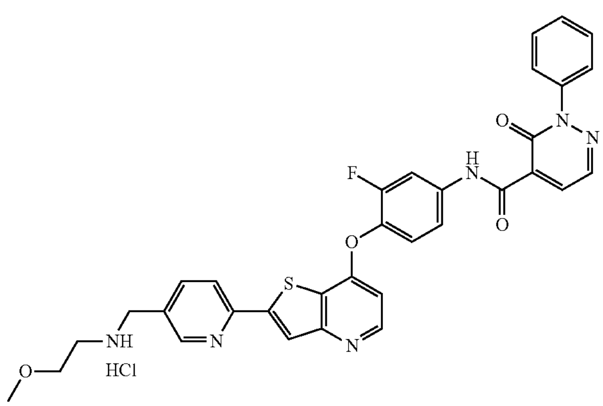 [SMILES: COCCNCc1ccc(-c2cc3nccc(Oc4ccc(NC(=O)c5ccnn(-c6ccccc6)c5=O)cc4F)c3s2)nc1 ; Cl] | 35.2% | ¹H NMR (500 MHz, DMSO-$d_6$) δ 11.77 (brs, 1H), 8.77 (s, 1H), 8.62 (d, J = 10.0 Hz, 1H), 8.46-8.39 (m, 3H), 8.18-8.16 (d, J = 5.0 Hz, 1H), 8.08 (d, J = 10.0 Hz, 1H), 7.64-7.50 (m, 8H), 6.84 (d, J = 5.0 Hz, 1H), 4.27 (t, J = 5.0 Hz, 2H), 3.64 (t, J = 5.0 Hz, 2H), 3.32 (s, 3H), 3.17-3.13 (m, 2H) |

TABLE 1-continued

| Ex. | Chemical structure | Yield | $^1$H NMR spectrum data |
|---|---|---|---|
| 20 | 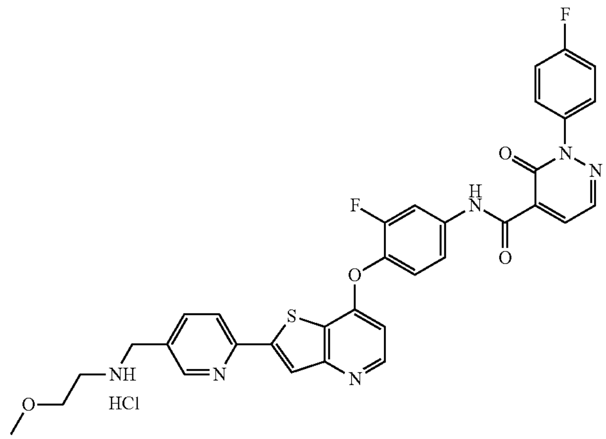 [SMILES: COCCNCc1ccc(-c2cc3nccc(Oc4ccc(NC(=O)c5ccnn(-c6ccc(F)cc6)c5=O)cc4F)c3s2)nc1 ; Cl] | 40.1% | $^1$H NMR (500 MHz, DMSO-d$_6$) δ 9.54 (br s, 2H), 8.80 (s, 1H), 8.67 (d, J = 10.0 Hz, 1H), 8.47-8.20 (m, 6H), 7.71-7.40 (m, 6H), 6.91 (d, J = 5.0 Hz, 1H), 4.26 (m, 2H), 3.66 (t, J = 5.0 Hz, 2H), 3.32 (s, 3H), 3.14 (m, 2H) |
| 21 | 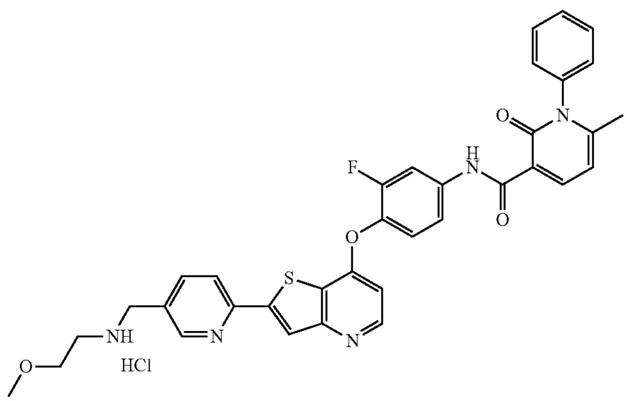 | 42.3% | $^1$H NMR (500 MHz, DMSO-d$_6$) δ 12.18 (s, 1H), 9.32 (brs, 2H), 8.77 (s, 1H), 8.62 (d, J = 5.0 Hz, 1H), 8.52 (d, J = 5.0 Hz, 1H), 8.46 (s, 1H), 8.40 (d, J = 10.0 Hz, 1H), 8.17 (d, J = 10.0 Hz, 1H), 8.09 (dd, J = 15.0 and 5.0 Hz, 1H), 7.64-7.51 (m, 5H), 7.44-7.42 (m, 2H), 6.82 (d, J = 5.0 Hz, 2H), 6.75 (d, J = 10.0 Hz, 1H), 4.28 (t, J = 5.0 Hz, 2H), 3.64 (t, J = 5.0 Hz, 2H), 3.33 (s, 3H), 3.19-3.14 (m, 2H), 2.09 (s, 3H) |
| 22 | 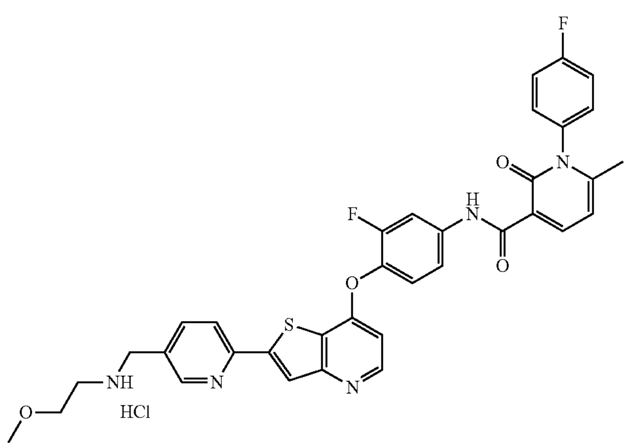 | 51.4% | $^1$H NMR (500 MHz, DMSO-d$_6$) δ 12.13 (s, 1H), 9.23 (brs, 2H), 8.75 (s, 1H), 8.59 (d, J = 5.0 Hz, 1H), 8.50 (d, J = 10.0 Hz, 1H), 8.44 (s, 1H), 8.38 (d, J = 10.0 Hz, 1H), 8.14 (dd, J = 10.0 and 5.0 Hz, 1H), 8.07 (d, J = 15.0 Hz, 1H), 7.56-7.43 (m, 6H), 6.77 (d, J = 5.0 Hz, 1H), 6.72 (d, J = 10.0 Hz, 1H), 4.26 (t, J = 5.0 Hz, 2H), 3.65-6.62 (m, 2H), 3.32 (s, 3H), 3.18-3.14 (m, 2H), 2.09 (s, 3H) |

TABLE 1-continued

| Ex. | Chemical structure | Yield | ¹H NMR spectrum data |
|---|---|---|---|
| 23 | 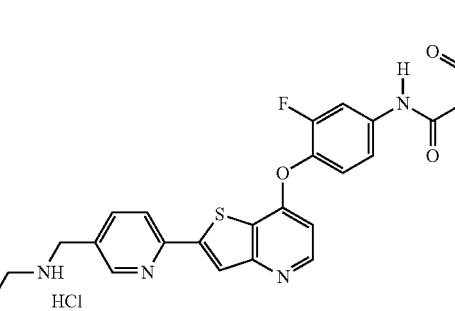 | 45.1% | ¹H NMR (500 MHz, DMSO-d₆) δ 11.99 (s, 1H), 9.34 (brs, 2H), 8.76 (d, J = 5.0 Hz, 1H), 8.61 (d, J = 10.0 Hz, 1H), 8.54-8.83 (m, 2H), 8.45 (s, 1H), 8.39 (d, J = 5.0 Hz, 1H), 8.16 (dd, J = 10.0 and 5.0 Hz, 1H), 8.07 (dd, J = 15.0 and 5.0 Hz, 1H), 7.65-7.63 (m, 2H), 7.60-7.52 (m, 2H), 7.45-7.42 (m, 2H), 6.81 (d, J = 5.0 Hz, 1H), 4.26 (t, J = 5.0 Hz, 2H), 3.64 (t, J = 5.0 Hz, 2H), 3.32 (s, 3H), 3.17-3.13 (m, 2H) |
| 24 | 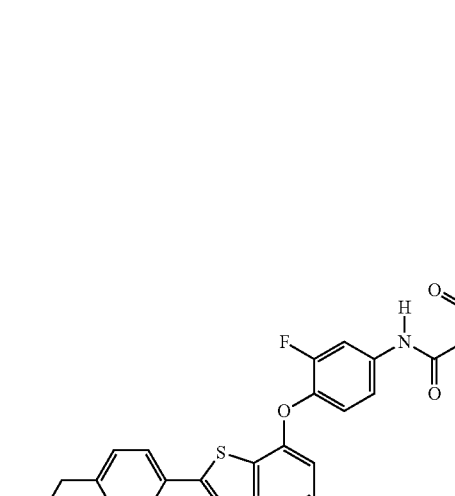 | 33.8% | ¹H NMR (500 MHz, DMSO-d₆) δ 11.99 (s, 1H), 9.11 (brs, 2H), 8.73 (s, 1H), 8.56 (d, J = 5.0 Hz, 1H), 8.51-8.48 (m, 2H), 8.44 (s, 1H), 8.38 (d, J = 10.0 Hz, 1H), 8.11 (dd, J = 10.0 and 5.0 Hz, 1H), 8.06 (dd, J = 15.0 and 5.0 Hz, 1H), 7.66-7.63 (m, 2H), 7.59-7.57 (m, 1H), 7.52 (t, J = 10.0 Hz, 1H), 7.46-7.42 (m, 2H), 6.74 (d, J = 5.0 Hz, 1H), 4.27 (t, J = 5.0 H, 2H), 3.62 (t, J = 5.0 Hz, 2H), 3.32 (s, 3H), 3.19-3.14 (m, 2H) |
| 25 | 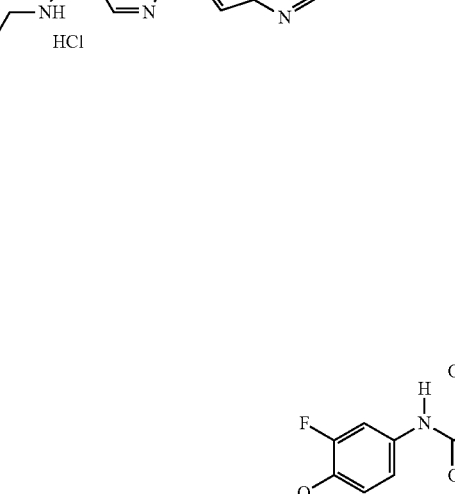 | 67.4% | ¹H NMR (500 MHz, DMSO-d₆) δ 10.95 (s, 1H), 9.24 (brs, 2H), 8.75 (s, 1H), 8.58 (d, J = 5.0 Hz, 1H), 8.44 (s, 1H), 8.39 (d, J = 10.0 Hz, 1H), 8.14 (d, J = 10.0 Hz, 1H), 7.98 (d, J = 15.0 Hz, 1H), 7.75 (d, J = 10.0 Hz, 1H), 7.53-7.49 (m, 4H), 7.41-7.37 (m, 2H), 6.79 (d, J = 5.0 Hz, 1H), 6.38 (d, J = 5.0 Hz, 1H), 4.27 (t, J = 5.0 H, 2H), 3.63 (t, J = 5.0 Hz, 2H), 3.32 (s, 3H), 3.17-3.13 (m, 2H), 2.31 (s, 3H) |

TABLE 1-continued

| Ex. | Chemical structure | Yield | ¹H NMR spectrum data |
|---|---|---|---|
| 26 | 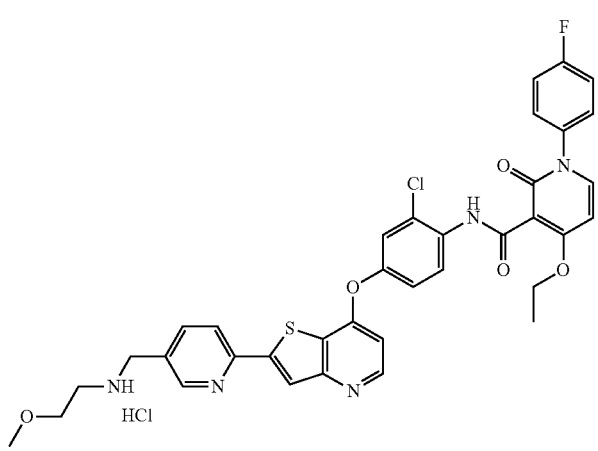 [SMILES: CCOc1ccn(-c2ccc(F)cc2)c(=O)c1C(=O)Nc1ccc(Oc2ccnc3cc(-c4ccc(CNCCOC)cn4)sc23)cc1Cl ; Cl] | 17.2% | ¹H NMR (500 MHz, DMSO-d$_6$) δ 11.18 (s, 1H), 9.18 (brs, 2H), 8.74 (s, 1H), 8.60 (d, J = 5.0 Hz, 1H), 8.44 (s, 1H), 8.40-8.35 (m, 2H), 8.13 (dd, J = 10.0 and 5.0 Hz, 1H), 7.96 (d, J = 10.0 Hz, 1H), 7.60 (s, 1H), 7.53-7.50 (m, 2H), 7.41-7.37 (m, 2H), 7.33 (dd, J = 10.0 and 5.0 Hz, 1H), 6.84 (d, J = 5.0 Hz, 1H), 6.58 (d, J = 5.0 Hz, 1H), 4.27 (t, J = 5.0 H, 2H), 3.62 (t, J = 5.0 Hz, 2H), 3.32 (s, 3H), 3.18-3.14 (m, 2H) |
| 27 | 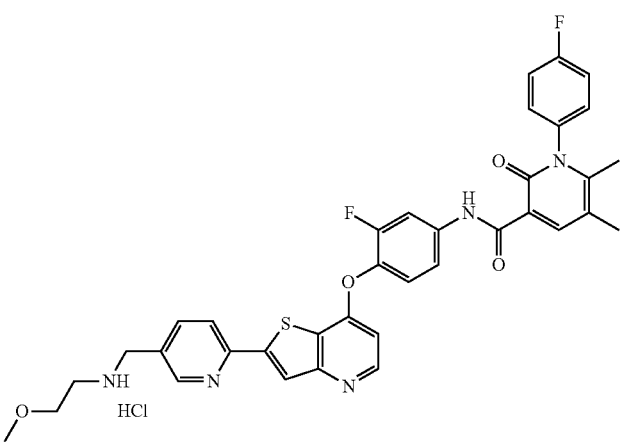 | 57.0% | ¹H NMR (500 MHz, DMSO-d$_6$) δ 12.26 (s, 1H), 9.22 (brs, 2H), 8.75 (s, 1H), 8.58 (d, J = 5.0 Hz, 1H), 8.45 (s, 1H), 8.44 (s, 1H), 8.38 (d, J = 5.0 Hz, 1H), 8.13 (dd, J = 10.0 and 5.0 Hz, 1H), 8.07 (dd, J = 15.0 and 5.0 Hz, 1H), 7.56-7.48 (m, 2H), 7.46-7.45 (m, 4H), 6.76 (d, J = 5.0 Hz, 1H), 4.26 (t, J = 5.0 H, 2H), 3.62 (t, J = 5.0 Hz, 2H), 3.32 (s, 3H), 3.18-3.13 (m, 2H) |
| 28 | 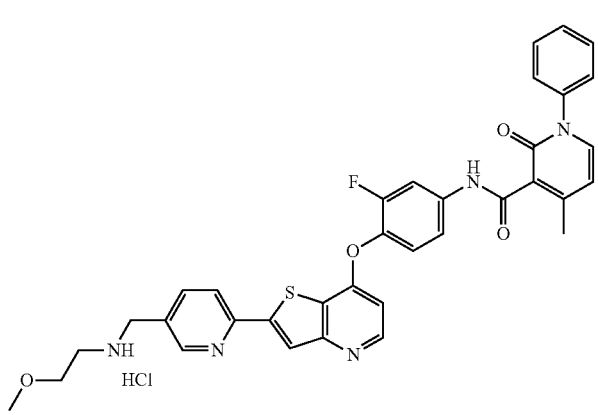 [SMILES: COCCNCc1ccc(-c2cc3nccc(Oc4ccc(NC(=O)c5c(C)ccn(-c6ccccc6)c5=O)cc4F)c3s2)nc1 ; Cl] | 57.0% | ¹H NMR (500 MHz, DMSO-d$_6$) δ 10.98 (s, 1H), 9.34 (brs, 2H), 8.77 (s, 1H), 8.61 (d, J = 5.0 Hz, 1H), 8.45 (s, 1H), 8.40 (d, J = 10.0 Hz, 1H), 8.17 (dd, J = 10.0 Hz and 5.0 Hz, 1H), 7.99 (d, J = 15.0 Hz, 1H), 7.75 (d, J = 5.0 Hz, 1H), 7.57-7.54 (m, 4H), 7.50-7.44 (m, 3H), 6.84 (d, J = 5.0 Hz, 1H), 6.38 (d, J = 5.0 Hz, 1H), 4.26 (t, J = 5.0 Hz, 2H), 3.65-3.63 (m, 2H), 3.31 (s, 3H), 3.17-3.13 (m, 2H), 2.31 (s, 3H) |

TABLE 1-continued

| Ex. | Chemical structure | Yield | ¹H NMR spectrum data |
|---|---|---|---|
| 29 | 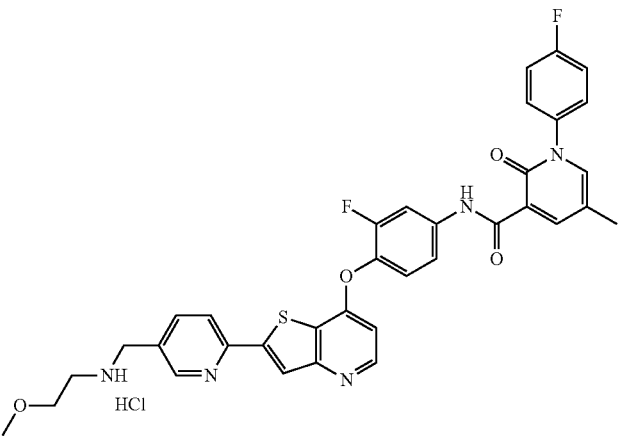 | 38.2% | ¹H NMR (500 MHz, DMSO-$d_6$) δ 12.32 (s, 1H), 9.30 (brs, 2H), 8.76 (s, 1H), 8.60 (d, J = 5.0 Hz, 1H), 8.48 (d, J = 5.0 Hz, 1H), 8.45 (s, 1H), 8.40 (d, J = 10.0 Hz, 1H), 8.16 (d, J = 10.0 Hz, 1H), 8.08 (d, J = 15.0 Hz, 1H), 8.01 (s, 1H), 7.62-7.51 (m, 4H), 7.45-7.41 (m, 2H), 6.80 (d, J = 5.0 Hz, 1H), 4.26 (t, J = 5.0 Hz, 2H), 3.63 (t, J = 5.0 Hz, 2H), 3.32 (s, 3H), 3.17-3.13 (m, 2H), 2.22 (s, 3H) |

Example 30. 4-ethoxy-N-(3-fluoro-4-{[2-(5-{[(2-methoxyethyl)(methyl)amino]methyl}pyridin-2-yl) thieno[3,2-b]pyridin-7-yl]oxy}phenyl)-1-(4-fluorophenyl)-2-oxo-1,2-dihydropyridine-3-carboxamide Hydrochloride

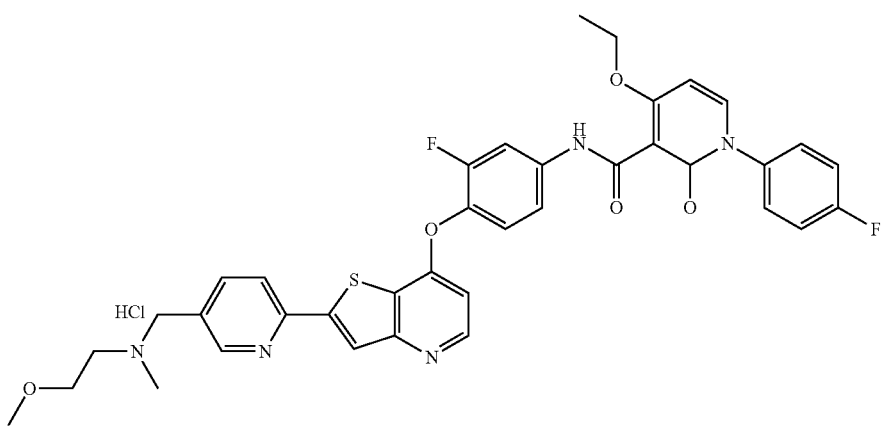 [SMILES: CCOC1=C(C(=O)Nc2ccc(Oc3ccnc4cc(-c5ccc(CN(C)CCOC)cn5)sc34)c(F)c2)C(O)N(c2ccc(F)cc2)C=C1 ; Cl]

4-Ethoxy-N-(3-fluoro-4-{[2-(5-([(2-methoxyethyl) amino]methyl}pyridin-2-yl)thieno[3,2-b]pyridin-7-yl] oxy}phenyl)-1-(4-fluorophenyl)-2-oxo-1,2-dihydropyridine-3-carboxamide hydrochloride (34 mg, 0.05 mmol) of Example 7 was dissolved in 1 mL of methanol, and formaldehyde (0.02 mL, 0.28 mmol) was added dropwise thereto. After stirring for 1 hour, sodium cyanohydride (12 mg, 0.19 mmol) was added thereto and the mixture was stirred for 12 hours. After completion of the reaction, the reaction mixture was extracted with dichloromethane and washed with a saturated aqueous sodium chloride solution. The organic layer was dried over anhydrous sodium sulfate and concentrated under reduced pressure. The resulting residue was purified by column chromatography, and 0.2 mL of 4 M hydrochloric acid in 1,4-dioxane was used to obtain the title compound (17.5 mg, yield: 50.5%, off-white solid).

¹H NMR (500 MHz, DMSO-$d_6$) δ 10.67 (s, 1H), 10.51 (brs, 1H), 8.80 (s, 1H), 8.60 (d, J=5.0 Hz, 1H), 8.48 (s, 1H), 8.43 (d, J=10.0 Hz, 1H), 8.21 (d, J=5.0 Hz, 1H), 7.96 (d, J=15.0 Hz, 1H), 7.88 (d, J=10.0 Hz, 1H), 7.52-7.45 (m, 4H), 7.39-7.36 (m, 2H), 6.83 (d, J=5.0 Hz, 1H), 6.53 (d, J=10.0 Hz, 1H), 4.51-4.36 (m, 2H), 4.27 (q, J=5.0 Hz, 2H), 3.73 (t, J=5.0 Hz, 2H), 3.38-3.29 (m, 2H), 3.32 (s, 3H), 2.75 (d, J=5.0 Hz, 3H)

Example 31. 4-ethoxy-N-[3-fluoro-4-({2-[5-(morpholinomethyl)pyridin-2-yl]thieno[3,2-b]pyridin-7-yl}oxy)phenyl]-1-(4-fluorophenyl)-2-oxo-1,2-dihydropyridine-3-carboxamide Hydrochloride Step 1: Synthesis of N-[4-({2-[5-(1,3-dioxolan-2-yl)pyridin-2-yl]thieno[3,2-b]pyridin-7-yl}oxy)-3-fluorophenyl]-4-ethoxy-1-(4-fluorophenyl)-2-oxo-1,2-dihydropyridine-3-carboxamide

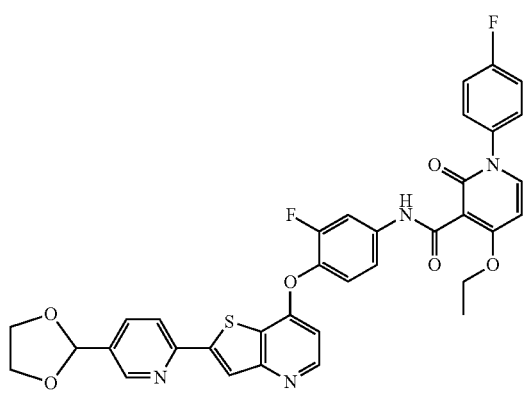 [SMILES: CCOc1ccn(-c2ccc(F)cc2)c(=O)c1C(=O)Nc1ccc(Oc2ccnc3cc(-c4ccc(C5OCCO5)cn4)sc23)c(F)c1]

The procedure of Step 6 of Example 1 was repeated except that 4-({2-[5-(1,3-dioxolan-2-yl)pyridin-2-yl]thieno[3,2-b]pyridin-7-yl}oxy)-3-fluoroaniline, which can be easily prepared by the method of International Patent Publication No. WO 2009/026717, was used as a starting material to obtain the title compound (135 mg, yield: 64%, off-white solid).

$^1$H NMR (500 MHz, DMSO-$d_6$) δ 10.63 (s, 1H), 8.70 (s, 1H), 8.52 (d, J=5.0 Hz, 1H), 8.41 (s, 1H), 8.32 (d, J=5.0 Hz, 1H), 7.99 (dd, J=10.0 and 5.0 Hz, 1H), 7.94 (d, J=10.0 Hz, 1H), 7.87 (d, J=10.0 Hz, 1H), 7.50-7.45 (m, 4H), 7.39-7.35 (m, 2H), 6.71 (d, J=5.0 Hz, 1H), 6.52 (d, J=5.0 Hz, 1H), 5.90 (s, 1H), 4.27 (qt, J=5.0H, 2H), 4.12-4.07 (m, 2H), 4.04-3.99 (m, 2H), 1.31 (t, J=5.0 Hz, 3H)

Step 2: Synthesis of 4-ethoxy-N-{3-fluoro-4-[2-(5-formylpyridin-2-yl)thieno[3,2-b]pyridin-7-yl]oxy}phenyl}-1-(4-fluorophenyl)-2-oxo-1,2-dihydropyridine-3-carboxamide

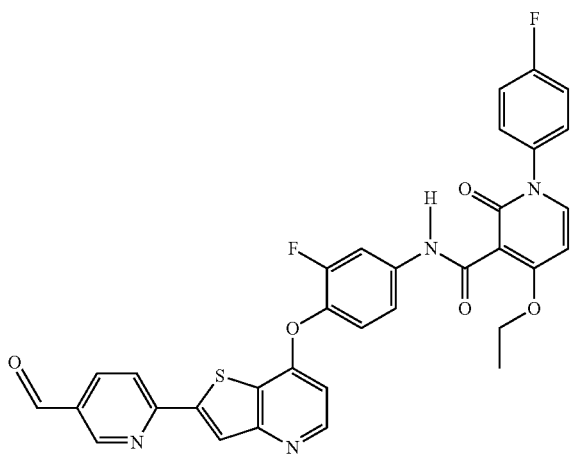 [SMILES: CCOc1ccn(-c2ccc(F)cc2)c(=O)c1C(=O)Nc1ccc(Oc2ccnc3cc(-c4ccc(C=O)cn4)sc23)c(F)c1]

The compound prepared in Step 1 (100 mg, 0.15 mmol) was dissolved in a mixed solution of acetone and water, and then 2 mL of trifluoroacetic acid was added dropwise thereto at room temperature. The mixture was stirred at 60° C. for 12 hours and then cooled to room temperature. The resulting solid was filtered off under reduced pressure, washed with water and diethyl ether, and dried to obtain the title compound (82 mg, yield: 88%, off-white solid).

$^1$H NMR (500 MHz, DMSO-$d_6$) δ 10.64 (s, 1H), 10.14 (s, 1H), 9.15 (s, 1H), 8.59-8.58 (m, 2H), 8.52 (d, J=5.0 Hz, 1H), 8.39 (d, J=10.0 Hz, 1H), 7.95 (d, J=10.0 Hz, 1H), 7.87 (d, J=10.0 Hz, 1H), 7.51-7.45 (m, 4H), 7.39-7.36 (m, 2H), 6.78 (d, J=5.0 Hz, 1H), 6.53 (d, J=10.0 Hz, 1H), 4.27 (qt, J=5.0H, 2H), 1.31 (t, J=5.0 Hz, 3H)

Step 3: Synthesis of 4-ethoxy-N-[3-fluoro-4-({2-[5-(hydroxymethyl)pyridin-2-yl]thieno[3,2-b]pyridin-7-yl}oxy)phenyl]-1-(4-fluorophenyl)-2-oxo-1,2-dihydropyridine-3-carboxamide

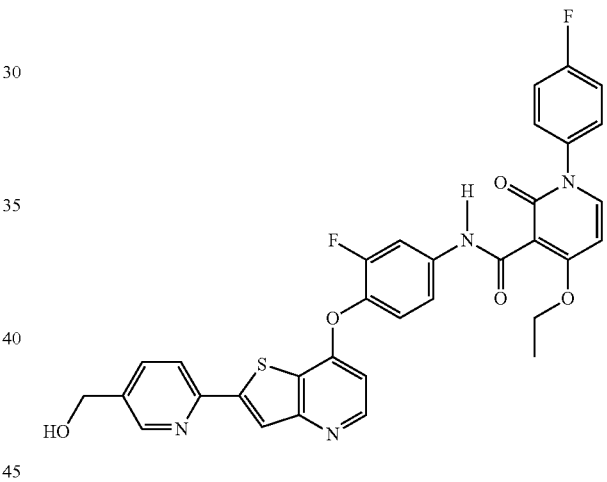

The compound prepared in Step 2 (82 mg, 0.13 mmol) was dissolved in 1,2-dichloroethane, and sodium triacetoxy borohydride (83 mg, 0.39 mmol) was added thereto, followed by stirring at room temperature for 12 hours. The reaction was terminated with a saturated aqueous sodium bicarbonate solution, and the mixture was extracted with dichloromethane. The separated organic layer was dried over anhydrous sodium sulfate and concentrated under reduced pressure. The resulting residue was purified by column chromatography to obtain the title compound (53 mg, yield: 64%, white solid).

$^1$H NMR (500 MHz, DMSO-$d_6$) δ 10.63 (s, 1H), 8.58 (s, 1H), 8.51 (d, J=5.0 Hz, 1H), 8.33 (s, 1H), 8.25 (d, J=10.0 Hz, 1H), 7.94 (d, J=10.0 Hz, 1H), 7.89-7.86 (m, 2H), 7.50-7.45 (m, 4H), 7.39-7.36 (m, 2H), 6.69 (d, J=5.0 Hz, 1H), 6.52 (d, J=5.0 Hz, 1H), 5.43 (t, J=5.0 Hz, 1H), 4.59 (d, J=5.0 Hz, 2H), 4.27 (qt, J=5.0H, 2H), 1.31 (t, J=5.0 Hz, 3H)

Step 4: Synthesis of N-[4-({2-[5-(chloromethyl)pyridin-2-yl]thieno[3,2-b]pyridin-7-yl}oxy)-3-fluorophenyl]-4-ethoxy-1-(4-fluorophenyl)-2-oxo-1,2-dihydropyridine-3-carboxamide

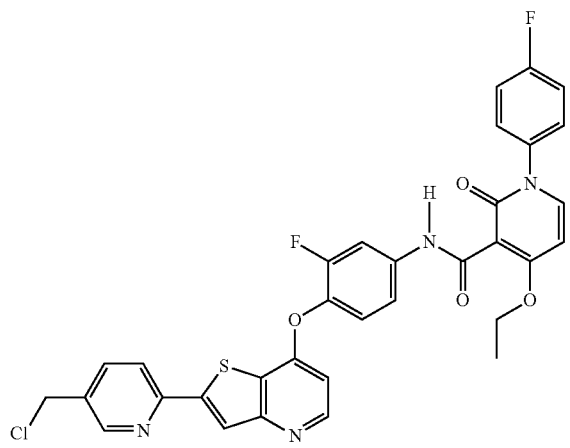 [SMILES: CCOc1ccn(-c2ccc(F)cc2)c(=O)c1C(=O)Nc1ccc(Oc2ccnc3cc(-c4ccc(CCl)cn4)sc23)c(F)c1]

The compound prepared in Step 3 (296 mg. 0.49 mmol) was dissolved in dichloromethane, thionyl chloride (0.07 mL, 0.97 mmol) was added thereto, and the mixture was stirred at room temperature for 3 hours. The reaction was terminated with a saturated aqueous sodium bicarbonate solution at 0° C., and the mixture was extracted with dichloromethane. The separated organic layer was dried over anhydrous sodium sulfate and concentrated under reduced pressure to obtain the title compound (240 mg, yield: 78%, yellow solid).

$^1$H NMR (500 MHz, DMSO-d$_6$) δ 10.63 (s, 1H), 8.72 (s, 1H), 8.52 (d, J=5.0 Hz, 1H), 8.40 (s, 1H), 8.32 (d, J=10.0 Hz, 1H), 8.04 (dd, J=10.0 and 5.0 Hz, 1H), 7.94 (d, J=15.0 Hz, 1H), 7.87 (d, J=10.0 Hz, 1H), 7.50-7.46 (m, 4H), 7.39-7.36 (m, 2H), 6.71 (d, J=5.0 Hz, 1H), 6.53 (d, J=10.0 Hz, 1H), 4.88 (s, 2H), 4.27 (qt, J=5.0H, 2H), 1.31 (t, J=5.0 Hz, 3H)

Step 5: Synthesis of 4-ethoxy-N-[3-fluoro-4-({2-[5-(morpholinomethyl)pyridin-2-yl]thieno[3,2-b]pyridin-7-yl}oxy)phenyl]-1-(4-fluorophenyl)-2-oxo-1,2-dihydropyridine-3-carboxamide Hydrochloride

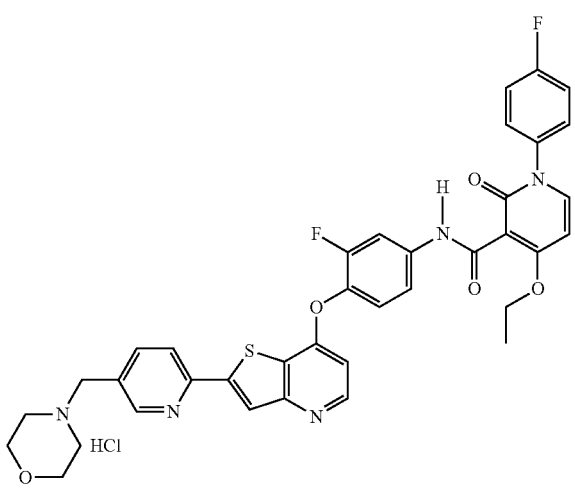 [SMILES: CCOc1ccn(-c2ccc(F)cc2)c(=O)c1C(=O)Nc1ccc(Oc2ccnc3cc(-c4ccc(CN5CCOCC5)cn4)sc23)c(F)c1 ; Cl]

The compound (40 mg, 0.06 mmol) prepared in Step 4 was dissolved in acetonitrile, morpholine (0.01 mL, 0.12 mmol) and potassium carbonate (13 mg, 0.09 mmol) were added thereto, and the mixture was stirred at 80° C. for 5 hours. After cooling to room temperature, the mixture was concentrated under reduced pressure, and then extracted with dichloromethane and a small amount of methanol. The separated organic layer was dried over anhydrous sodium sulfate and concentrated under reduced pressure. The residue was purified by column chromatography, and 0.2 mL of 4 M hydrochloric acid in 1,4-dioxane was used to obtain the title compound (16.6 mg, yield: 30%, off-white solid).

$^1$H NMR (500 MHz, DMSO-d$_6$) δ 10.66 (s, 1H), 8.81 (s, 1H), 8.60 (d, J=5.0 Hz, 1H), 8.48 (s, 1H), 8.43 (d, J=5.0 Hz, 1H), 8.23 (d, J=5.0 Hz, 1H), 7.96 (d, J=15.0 Hz, 1H), 7.87 (d, J=5.0 Hz, 1H), 7.52-7.45 (m, 4H), 7.39-7.36 (m, 2H), 6.83 (d, J=5.0 Hz, 1H), 6.53 (d, J=10.0 Hz, 1H), 4.44 (s, 2H), 4.26 (qt, J=5.0H, 2H), 3.96-3.94 (m, 2H), 3.77 (t, J=10.0 Hz, 2H), 3.32-3.30 (m, 2H), 3.14 (qt, J=10.0 2H), 1.31 (t, J=5.0 Hz, 3H)

Example 32. 4-ethoxy-N-[3-fluoro-4-({2-[5-(morpholinomethyl)pyridin-2-yl]thieno[3,2-b]pyridin-7-yl}oxy)phenyl]-2-oxo-1-phenyl-1,2-dihydropyridine-3-carboxamide Hydrochloride The synthesis route of Example 31 was repeated except that 4-ethoxy-2-oxo-1-phenyl-1,2-dihydropyridine-3-carboxylic acid of Preparation Example 3 was used as a starting material in Step 1 to obtain the title compound.

Example 33. 4-ethoxy-N-{3-fluoro-4-[(2-{5-[(4-methylpiperazin-1-yl)methyl]pyridin-2-yl}thieno[3,2-b]pyridin-7-yl)oxy]phenyl}-1-(4-fluorophenyl)-2-oxo-1,2-dihydropyridine-3-carboxamide Hydrochloride The synthesis route of Example 31 was repeated except that N-methylpiperazine was used instead of morpholine in Step 5 to obtain the title compound.

Example 34. 4-ethoxy-N-{3-fluoro-4-[(2-{5-[(-methylpiperazin-1-yl)methyl]pyridin-2-yl}thieno[3,2-b]pyridin-7-yl)oxy]phenyl}-2-oxo-1-phenyl-1,2-dihydropyridine-3-carboxamide Hydrochloride The synthesis route of Example 32 was repeated except that N-methylpiperazine was used instead of morpholine in Step 5 to obtain the title compound.

Example 35. 1-(4-chlorophenyl)-4-ethoxy-N-[3-fluoro-4-({2-[5-(morpholinomethyl)pyridin-2-yl]thieno[3,2-b]pyridin-7-yl}oxy)phenyl]-2-oxo-1,2-dihydropyridine-3-carboxamide Hydrochloride The synthesis route of Example 31 was repeated except that 4-ethoxy-1-(4-chlorophenyl)-2-oxo-1,2-dihydropyridine-3-carboxylic acid of Preparation Example 4 was used as a starting material in Step 1 to obtain the title compound.

Example 36. N-[3-chloro-4-({2-[5-(morpholinomethyl)pyridin-2-yl]thieno[3,2-b]pyridin-7-yl}oxy)phenyl]-4-ethoxy-1-(4-fluorophenyl)-2-oxo-1,2-dihydropyridine-3-carboxamide Hydrochloride The synthesis route of Example 31 was repeated except that 4-({2-[5-(1,3-dioxolan-2-yl)pyridin-2-yl]thieno[3,2-b]pyridin-7-yl}oxy)-3-chloroaniline, which can be easily prepared by the method of International Patent Publication No.

WO 2009/026717, was used as a starting material to obtain the title compound.

Example 37. N-[2-chloro-4-({2-[5-(morpholinomethyl)pyridin-2-yl]thieno[3,2-b]pyridin-7-yl}oxy)phenyl]-4-ethoxy-1-(4-fluorophenyl)-2-oxo-1,2-dihydropyridine-3-carboxamide Hydrochloride The synthesis route of Example 31 was repeated except that 4-({2-[5-(1,3-dioxolan-2-yl)pyridin-2-yl]thieno[3,2-b]pyridin-7-yl}oxy)-2-chloroaniline, which can be easily prepared by the method of International Patent Publication No. WO 2009/026717, was used as a starting material to obtain the title compound.

The chemical structures, yields and NMR spectrum data of the compounds of the above Examples 32 to 37 are summarized in Table 2 below.

TABLE 2

| Ex. | Chemical structure | Yield | $^1$H NMR spectrum data |
|---|---|---|---|
| 32 | 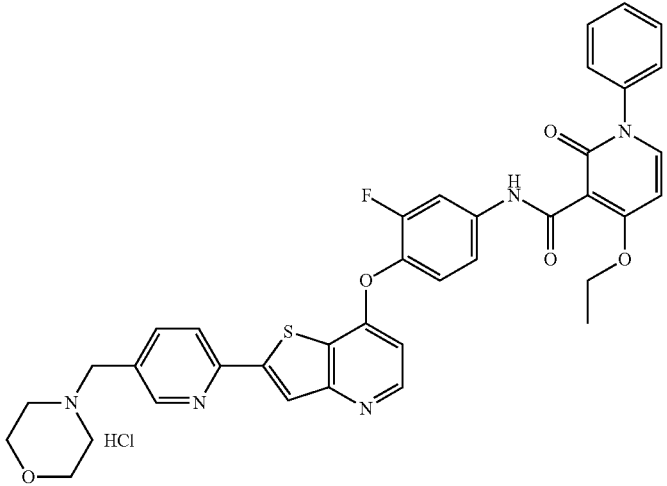 [SMILES: CCOc1ccn(-c2ccccc2)c(=O)c1C(=O)Nc1ccc(Oc2ccnc3cc(-c4ccc(CN5CCOCC5)cn4)sc23)c(F)c1 ; Cl] | 52.3% | $^1$H NMR (500 MHz, DMSO-d$_6$) δ 10.66 (s, 1H), 8.80 (s, 1H), 8.58 (d, J = 5.0 Hz, 1H), 8.47 (s, 1H), 8.43 (d, J = 10.0 Hz, 1H), 8.20 (d, J = 10.0 Hz, 1H), 7.96 (d, J = 15.0 Hz, 1H), 7.87 (d, J = 5.0 Hz, 1H), 7.56-7.47 (m, 5H), 7.43-7.40 (m, 2H), 6.80 (d, J = 5.0 Hz, 1H), 6.52 (d, J = 5.0 Hz, 1H), 4.44 (s, 2H), 4.26 (qt, J = 5.0 H, 2H), 3.97-3.95 (m, 2H), 3.74 (t, J = 10.0 Hz, 2H), 3.33-3.30 (m, 2H), 3.14 (qt, J = 10.0 2H), 1.31 (t, J = 5.0 Hz, 3H) |
| 33 | 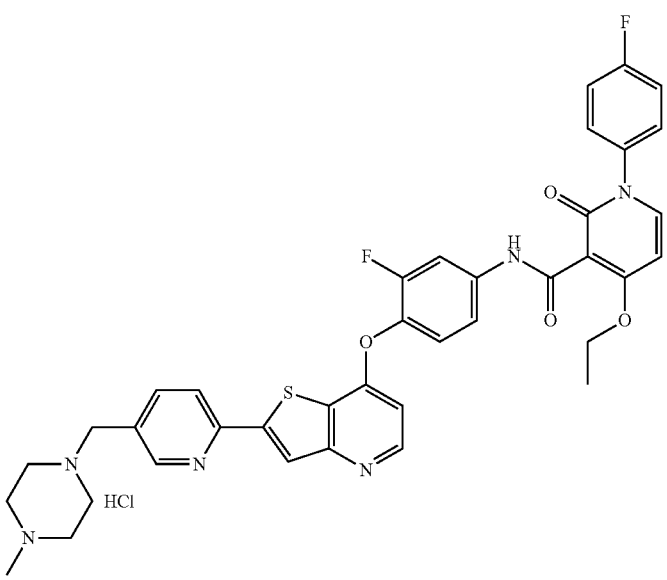 [SMILES: CCOc1ccn(-c2ccc(F)cc2)c(=O)c1C(=O)Nc1ccc(Oc2ccnc3cc(-c4ccc(CN5CCN(C)CC5)cn4)sc23)c(F)c1 ; Cl] | 22.2% | $^1$H NMR (500 MHz, DMSO-d$_6$) δ 10.67 (s, 1H), 8.81 (brs, 1H), 8.60 (d, J = 5.0 Hz, 1H), 8.46 (s, 1H), 8.41 (d, J = 10.0 Hz, 1H), 8.20 (s, 1H), 7.96 (d, J = 15.0 Hz, 1H), 7.87 (d, J = 5.0 Hz, 1H), 7.52-7.45 (m, 4H), 7.39-7.36 (m, 2H), 6.84 (d, J = 5.0 Hz, 1H), 6.53 (d, J = 10.0 Hz, 1H), 4.26 (qt, J = 5.0 H, 2H), 4.07 (brs, 8H), 3.56 (brs, 2H), 2.80 (s, 3H), 1.31 (t, J = 5.0 Hz, 3H) |

TABLE 2-continued

| Ex. | Chemical structure | Yield | ¹H NMR spectrum data |
|---|---|---|---|
| 34 | 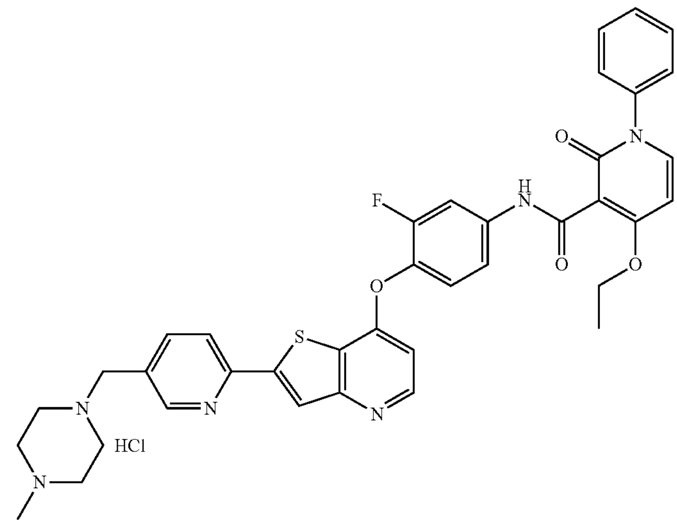 [SMILES: CCOc1ccn(-c2ccccc2)c(=O)c1C(=O)Nc1ccc(Oc2ccnc3cc(-c4ccc(CN5CCN(C)CC5)cn4)sc23)c(F)c1 ; Cl] | 31.4% | ¹H NMR (500 MHz, DMSO-d$_6$) δ 10.68 (s, 1H), 8.82 (brs, 1H), 8.61 (d, J = 5.0 Hz, 1H), 8.47 (s, 1H), 8.41 (d, J = 5.0 Hz, 1H), 8.23 (s, 1H), 7.97 (d, J = 15.0 Hz, 1H), 7.87 (d, J = 5.0 Hz, 1H), 7.56-7.46 (m, 5H), 7.42-7.40 (m, 2H), 6.86 (d, J = 5.0 Hz, 1H), 6.52 (d, J = 5.0 Hz, 1H), 4.26 (qt, J = 5.0 H, 2H), 3.93 (brs, 8H), 3.58 (brs, 2H), 2.81 (s, 3H), 1.31(t, J = 5.0Hz, 3H) |
| 35 | 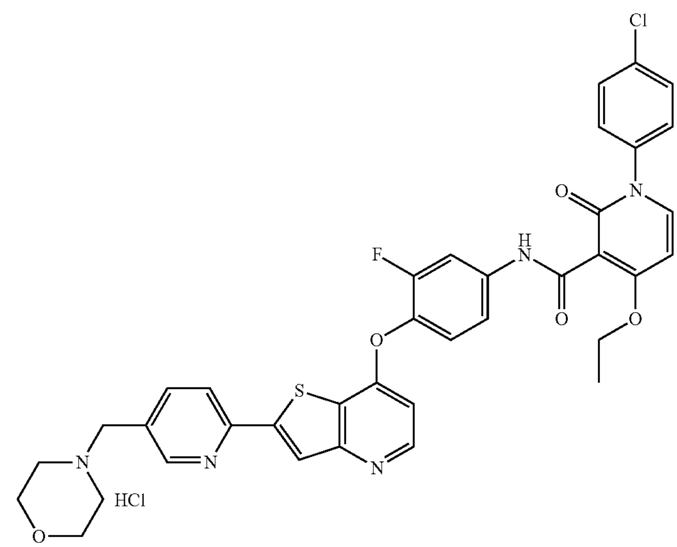 [SMILES: CCOc1ccn(-c2ccc(Cl)cc2)c(=O)c1C(=O)Nc1ccc(Oc2ccnc3cc(-c4ccc(CN5CCOCC5)cn4)sc23)c(F)c1 ; Cl] | 8.7% | ¹H NMR (500 MHz, DMSO-d$_6$) δ 11.04 (brs, 1H), 10.65 (s, 1H), 8.80 (s, 1H), 8.59 (d, J = 5.0 Hz, 1H), 8.48 (s, 1H), 8.43 (d, J = 10.0 Hz, 1H), 8.21 (d, J = 10.0 Hz, 1H), 7.96 (d, J = 10.0 Hz, 1H), 7.88 (d, J = 5.0 Hz, 1H), 7.61-7.60 (m, 2H), 7.51-7.45 (m, 4H), 6.81 (d, J = 5.0 Hz, 1H), 6.55 (d, J = 10.0 Hz, 1H), 4.45 (s, 2H), 4.27 (qt, J = 5.0 H, 2H), 3.97-3.95 (m, 2H), 3.74 (t, J = 10.0 Hz, 2H), 3.32 (d, J = 10.0 Hz, 2H), 3.16-3.14 (m, 2H), 1.30 (t, J = 5.0 Hz, 3H) |
| 36 | 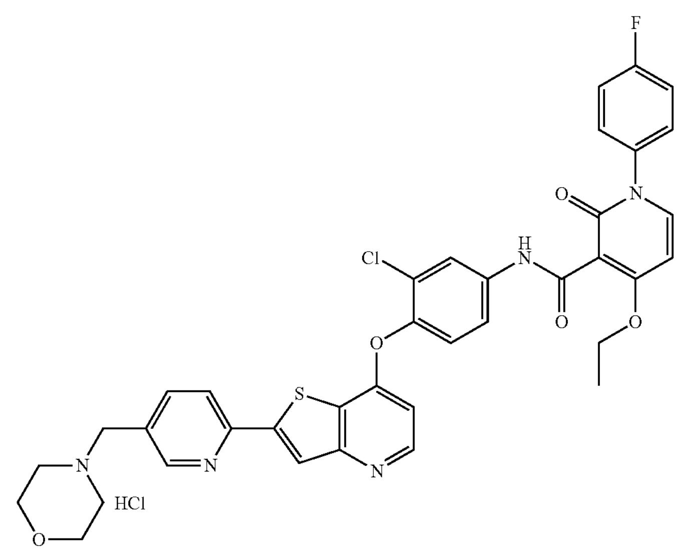 [SMILES: CCOc1ccn(-c2ccc(F)cc2)c(=O)c1C(=O)Nc1ccc(Oc2ccnc3cc(-c4ccc(CN5CCOCC5)cn4)sc23)c(Cl)c1 ; Cl] | 17.3% | ¹H NMR (500 MHz, DMSO-d$_6$) δ 11.20 (brs, 1H), 10.65 (s, 1H), 8.81 (s, 1H), 8.59 (d, J = 5.0 Hz, 1H), 8.47 (s, 1H), 8.43 (d, J = 10.0 Hz, 1H), 8.23 (d, J = 10.0 Hz, 1H), 8.15 (d, J = 5.0 Hz, 1H), 7.88 (d, J = 10.0 Hz, 1H), 7.68 (d, J = 10.0, 1H), 7.52 (d, J = 10.0 Hz, 1H), 7.48-7.46 (m, 2H), 7.39-7.36 (m, 2H), 6.75 (d, J = 5.0 Hz, 1H), 6.53 (d, J = 5.0 Hz, 1H), 4.44 (s, 2H), 4.27 (qt, J = 5.0 H, 2H), 3.97-3.94 (m, 2H), 3.79-3.74 (m, 2H), 3.32-3.30 (m, 2H), 3.15-3.14 (m, 2H), 1.30 (t, J = 5.0 Hz, 3H) |

TABLE 2-continued

| Ex. | Chemical structure | Yield | ¹H NMR spectrum data |
|---|---|---|---|
| 37 | (structure shown) | 11.5% | ¹H NMR (500 MHz, DMSO-d$_6$) δ 11.17 (s, 1H), 8.77 (s, 1H), 8.59 (d, J = 5.0 Hz, 1H), 8.47 (s, 1H), 8.42 (d, J = 10.0 Hz, 1H), 8.35 (d, J = 10.0 Hz, 1H), 8.15 (d, J = 5.0 Hz, 1H), 7.96 (d, J = 10.0 Hz, 1H), 7.59 (s, 1H), 7.53-7.50 (m, 2H), 7.41-7.37 (m, 2H), 7.33 (d, J = 10.0 Hz, 1H), 6.82 (d, J = 5.0 Hz, 1H), 6.58 (d, J = 5.0 Hz, 1H), 4.45 (s, 2H), 4.30 (qt, J = 5.0 H, 2H), 3.98-3.95 (m, 2H), 3.72-3.67 (m, 2H), 3.43 (m, 2H), 3.19-3.15 (m, 2H), 1.37 (t, J = 5.0 Hz, 3H) |

In addition, the following known compounds were used for comparison.

Comparative Example 1

Compound 1 of U.S. Pat. No. 8,536,200 B2, N-{4-[(2-amino-3-chloro-4-pyridinyl)oxy]-3-fluorophenyl}-4-ethoxy-1-(4-fluorophenyl)-2-oxo-1,2-dihydro-3-pyridinecarboxamide, which is a well-known RON inhibitor, BMS-777607.

Comparative Example 2

Compound of Example 73 of U.S. Pat. No. 8,088,794 B2, N-(3-fluoro-4-(7-methoxyquinolin-4-yloxy)phenyl)-1-(2-hydroxy-2-methylpropyl)-5-methyl-3-oxo-2-phenyl-2,3-dihydro-1H-pyrazole-4-carboxamide.

Comparative Example 3

Compound of Example 1 of U.S. Pat. No. 8,030,302 B2, N-(3-fluoro-4-(1-methyl-6-(1H-pyrazol-4-yl)-1H-indazol-5-yloxy)phenyl)-1-(4-fluorophenyl)-6-methyl-2-oxo-1,2-dihydropyridine-3-carboxamide.

Experimental Example 1. Measurement of Enzyme Inhibitory Activity of Thienopyridine Derivatives The enzyme inhibitory activity (IC$_{50}$) of the thienopyridine derivative was measured using FRET (fluorescence resonance energy transfer) technique. RON kinase (Carna Bioscience) was diluted with a kinase assay buffer (50 mM HEPES pH 7.5, 1 mM EGTA, 10 mM MgCl$_2$, 2 mM DTT, and 0.01% Tween-20) to a concentration of 2× (0.4 nM) the final reaction concentration and the dilution was added to a 384-well plate at 5 μL/well.

As sample compounds, the compounds synthesized in the examples of the present invention and the compounds of the comparative examples were used. The sample compounds were respectively dissolved in 100% DMSO to obtain 1 mM stock solutions, which were then subjected to eight 10-fold serial dilutions. The sample compounds were diluted with the kinase assay buffer to a concentration of 4× the final reaction concentration, and the dilutions were added to the 384-well plate at 2.5 μL/well. The plate was incubated at room temperature for 15 minutes.

Next, 0.25 M ATP solution (Sigma Aldrich) was diluted with the kinase reaction buffer to a concentration of 4× (60 μM) the final reaction concentration, and a tyrosine peptide substrate (Perkin-Elmer) was diluted therein to a concentration of 4× (400 nM) the final reaction concentration. The dilution was added to the 384-well plate at 2.5 μL/well.

Then, the 384-well plate was incubated at room temperature and the reaction was allowed to proceed for 60 minutes. After 60 minutes, EDTA (Sigma Aldrich) was diluted with TR-FRET detection buffer (Perkin-Elmer) to a concentration of 4× (40 mM) the final reaction concentration.

A europium-labeled anti-phosphotyrosine antibody (Perkin-Elmer) was diluted in the above EDTA dilution to a concentration of 4× (8 nM) the final reaction concentration to prepare a stop solution of the RON kinase reaction. The stop solution was added to the 384-well plate at 10 μL/well to terminate the reaction, and the plate was incubated at room temperature for 60 minutes.

Thereafter, the plate was read on Victor X5 plate reader (Perkin-Elmer). At this time, the excitation wavelength was 340 nm and the emission wavelengths were 620 nm and 665 nm. The IC$_{50}$ values of the sample compounds were determined using GraphPad Prism™ 5 by expressing the emission energy at 665 nm as a function of the sample compound concentration. The results are shown in Table 3.

TABLE 3

| Item | IC$_{50}$ (nM) |
|---|---|
| Comp. Ex. 1 | 1.11 |
| Comp. Ex. 2 | 2.89 |
| Comp. Ex. 3 | 3.74 |
| Example 1 | 0.51 |
| Example 2 | 0.10 |
| Example 3 | 0.42 |
| Example 4 | 0.68 |

TABLE 3-continued

| Item | IC$_{50}$ (nM) |
| --- | --- |
| Example 5 | 1.15 |
| Example 6 | 21.95 |
| Example 7 | 0.28 |
| Example 8 | 0.01 |
| Example 9 | 0.08 |
| Example 10 | 5.66 |
| Example 11 | 0.26 |
| Example 12 | 2.10 |
| Example 13 | 1.14 |
| Example 14 | 0.45 |
| Example 15 | 2.93 |
| Example 16 | 3.43 |
| Example 17 | 1.59 |
| Example 18 | 0.77 |
| Example 19 | 3.66 |
| Example 20 | 2.47 |
| Example 21 | 0.56 |
| Example 22 | 0.44 |
| Example 23 | 8.05 |
| Example 24 | 24.18 |
| Example 25 | 0.23 |
| Example 26 | 3.70 |
| Example 27 | 1.93 |
| Example 28 | 0.56 |
| Example 29 | 1.21 |
| Example 30 | 0.88 |
| Example 31 | 0.39 |
| Example 32 | 0.81 |
| Example 33 | 0.26 |
| Example 34 | 0.23 |
| Example 35 | 2.55 |
| Example 36 | 2.28 |
| Example 37 | 10.29 |

As shown in Table 3 above, the compounds of the Examples have a very excellent inhibitory activity on the RON tyrosine kinase.

Experimental Example 2. Measurement of Cell Killing Efficacy of the Thienopyridine Derivatives According to their Concentrations Two colon cancer cell lines, RON-activated KM12C (80015, KCLB, MEM+10% FBS) and RON-mutated (Δ160) HT-29 (30038, KCLB, RPMI+10% FBS) were prepared in 6-well plates at 5×10$^4$ cells/well, respectively. After 24 hours, while freshly changing the medium, the sample compounds were added to the wells at a concentration of 1 μM or 5 μM and the plates were allowed to stand for 48 hours.

As the sample compounds, the compounds synthesized in the examples of the present invention and the compounds of the comparative examples were used.

After 48 hours, the cell suspensions were collected and centrifuged (1,500 rpm, 4 min.) to obtain the cells, and live cells and dead cells were quantitated (n=2) through a trypan blue (15250-061, Gibco) exclusion assay. The statistical analysis was performed using Excel™ T-test from Microsoft.

Figure 2:
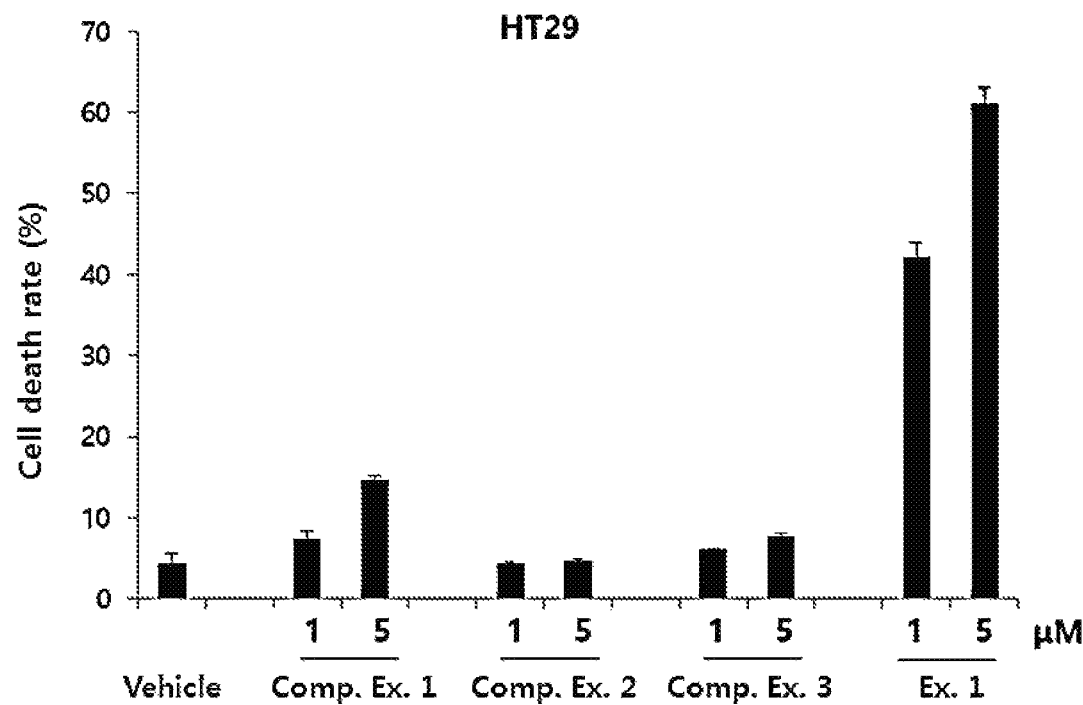

The measured cell death rates (%) of the compounds of Comparative Examples 1 to 3 and Example 1 are shown in FIGS. 1 and 2.

The cell death rates of the compounds of Examples and Comparative Examples were respectively measured and the results are shown in Table 4 as relative ratios to Comparative Example 1.

TABLE 4

| | Cell death rate (Relative to Comp. Ex. 1) | | | |
| --- | --- | --- | --- | --- |
| | KM12C cell | | HT29 cell | |
| Item | 1 μM | 5 μM | 1 μM | 5 μM |
| Comp. Ex. 1 | x 1.00 | x 1.00 | x 1.00 | x 1.00 |
| Comp. Ex. 2 | x 0.38 | x 0.31 | x 0.59 | x 0.32 |
| Comp. Ex. 3 | x 0.54 | x 0.33 | x 0.83 | x 0.52 |
| Example 1 | x 3.37 | x 2.47 | x 4.06 | x 2.41 |
| Example 2 | x 1.33 | x 0.74 | x 0.62 | x 1.15 |
| Example 3 | x 0.66 | x 1.26 | x 1.80 | x 2.22 |
| Example 4 | x 0.59 | x 0.80 | x 3.51 | x 3.63 |
| Example 7 | x 2.38 | x 1.32 | x 2.97 | x 2.90 |
| Example 8 | x 0.92 | x 1.19 | x 2.24 | x 2.52 |
| Example 9 | x 2.26 | x 2.87 | x 4.08 | x 3.53 |
| Example 11 | x 0.99 | x 1.65 | x 1.16 | x 0.94 |
| Example 14 | x 1.58 | x 1.43 | x 1.59 | x 3.81 |
| Example 18 | x 0.56 | x 1.09 | x 1.33 | x 1.37 |
| Example 20 | x 1.07 | x 1.11 | x 0.75 | x 1.13 |
| Example 21 | x 0.93 | x 4.06 | x 1.30 | x 4.10 |
| Example 22 | x 1.48 | x 1.61 | x 1.07 | x 1.71 |
| Example 25 | x 0.44 | x 0.69 | x 3.13 | x 2.97 |
| Example 28 | x 1.22 | x 1.58 | x 1.46 | x 2.65 |
| Example 30 | x 2.48 | x 2.06 | x 1.34 | x 1.07 |
| Example 31 | x 1.52 | x 1.17 | x 2.11 | x 1.21 |
| Example 32 | x 1.52 | x 1.11 | x 1.55 | x 1.45 |
| Example 33 | x 1.99 | x 2.13 | x 2.01 | x 1.50 |
| Example 34 | x 2.07 | x 1.11 | x 2.12 | x 1.66 |

As shown in Table 4 and FIGS. 1 and 2, the compounds of the Examples exhibited relatively high anticancer efficacy in the RON-activated (KM12C) and RON-mutated (HT129) colon cancer cell lines, as compared to the conventional compounds.

Experimental Example 3. Confirmation of the Cytotoxicity of Thienopyridine Derivatives Using MTS Assay In order to confirm the specific cytotoxicity of the drugs, the cultured cells were treated with 0.05% trypsin/EDTA (0.5% trypsin EDTA (10×), Product No.: 15400-054, GIBCO) to detach them from the culture dish, and 3,000 cells (KM12C) or 2,000 cells (HT29, Colo 320 HSR) were dispensed into each well.

After 24 hours, sample compounds were dissolved in DMSO (Product No.: D8418-250ML, SIGMA) to make 10 mM stock solutions. As the sample compounds, the compounds synthesized in the examples of the present invention and the compounds of the comparative examples were used.

The stock solutions were respectively diluted with DMSO to eight concentrations (for KM12C) starting from 10 mM by a factor of 1/10 and nine concentrations (for HT29) starting from 10 mM by a factor of ½, and the diluted sample compounds had a concentration of 100 μM based on the highest concentration. The cells were treated with the sample compound dilutions, and cultured in a 5% CO$_2$ incubator at 37° C. for 72 hours.

Thereafter, 20 μL of MTS solution (CellTiter™ 96 Aqueous One Solution Cell Proliferation Assay, Product No.: G3581, Promega) was dispensed into each well and mixed well, and the cells were incubated for 1 to 4 hours at 37° C. in a 5% CO$_2$ incubator. Then, the absorbance was measured at a wavelength of 490 nm using Victor X5 plate reader (Perkin-Elmer) and the IC$_{50}$ values were calculated therefrom. The results are shown in Table 5.

TABLE 5

| Item | KM12C IC$_{50}$ (μM) | HT29 IC$_{50}$ (μM) |
| --- | --- | --- |
| Comp. Ex. 1 | 0.511 | 10~20 |
| Comp. Ex. 3 | 0.1173 | 10.83 |
| Example 1 | 0.045 | 1.103 |
| Example 14 | 0.063 | 0.668 |
| Example 20 | 0.010 | >10 |
| Example 21 | 1.50 | 1.30 |
| Example 22 | 0.001 | 1.18 |
| Example 25 | 0.025 | 1.384 |
| Example 28 | 0.059 | 0.908 |
| Example 31 | 0.007 | 0.609 |
| Example 32 | 0.003 | 0.325 |
| Example 33 | 0.009 | 0.335 |
| Example 34 | 0.006 | 0.129 |

As shown in Table 5, the compounds of the Examples exhibited relatively high anticancer efficacy in the RON-activated (KM12C) and RON-mutated (HT29) colon cancer cell lines, as compared to the conventional compounds.

The invention claimed is:

1. A compound represented by the following Formula 1, or a pharmaceutically acceptable salt thereof:

Formula 1 wherein
$R_1$ and $R_2$ are each independently H, halogen, $C_{1-10}$ alkoxy, or halo $C_{1-10}$ alkyl;
X is —C(—$R_3$)= or —N=;
$R_3$ and $R_4$ are each independently H, halogen, $C_{1-10}$ alkyl, or $C_{1-10}$ alkoxy;
$R_5$ is H, halogen, or $C_{1-10}$ alkyl; and
$R_6$ and $R_7$ are each independently H, $C_{1-10}$ alkyl, or —(CH$_2$)$_n$—Y—$R_8$, or $R_6$ and $R_7$, taken together with the N atom to which they are bonded, form a 4- to 10-membered heterocycle,
wherein n is an integer of 0 to 10;
Y is —O—, —C(=O)—, —C(=O)—O—, —S—, or —S(=O)$_2$—;
$R_8$ is a linear or branched $C_{1-10}$ alkyl, wherein $R_8$ is unsubstituted or substituted with one or more substituents selected from the group consisting of halogen, amino, hydroxyl and $C_{1-6}$ alkoxy; and
said heterocycle optionally further contain one or two heteroatoms selected from the group consisting of N, O, and S, in addition to the N atom to which $R_6$ and $R_7$ are bonded, and is unsubstituted or substituted with one or more substituents selected from halogen and $C_{1-6}$ alkyl.

2. The compound or the pharmaceutically acceptable salt thereof according to claim 1, wherein $R_1$ and $R_2$ are each independently H, halogen, methoxy, or —CF$_3$.

3. The compound or the pharmaceutically acceptable salt thereof according to claim 1, wherein $R_3$ and $R_4$ are each independently H, halogen, methyl, methoxy, or ethoxy.

4. The compound or the pharmaceutically acceptable salt thereof according to claim 1, wherein X is —C(—$R_3$)=; and $R_3$ and $R_4$ are each independently H, halogen, methyl, methoxy, or ethoxy, but not simultaneously H.

5. The compound or the pharmaceutically acceptable salt thereof according to claim 1, wherein X is —N=; and $R_4$ is halogen, methyl, methoxy, or ethoxy.

6. The compound or the pharmaceutically acceptable salt thereof according to claim 1, wherein $R_5$ is H or halogen.

7. The compound or the pharmaceutically acceptable salt thereof according to claim 1, wherein $R_6$ and $R_7$ are each independently H, $C_{1-6}$ alkyl, —$C_{1-6}$ alkylene-O—$C_{1-10}$ alkyl, or —C(=O)—O—$C_{1-10}$ alkyl, but not simultaneously H.

8. The compound or the pharmaceutically acceptable salt thereof according to claim 1, wherein $R_6$ and $R_7$, taken together with the N atom to which they are bonded, form wherein $R_a$ and $R_b$ are each independently $C_{1-3}$ alkylene, A is —N(—$R_9$)— or —O—, and $R_9$ is $C_{1-6}$ alkyl.

9. The compound or the pharmaceutically acceptable salt thereof according to claim 1, wherein $R_1$ and $R_2$ are each independently H, halogen, methoxy, or —CF$_3$; $R_3$ and $R_4$ are each independently H, halogen, methyl, methoxy, or ethoxy; $R_5$ is H or halogen; and $R_6$ is —C$_2$H$_4$—O—CH$_3$ and $R_7$ is H, methyl, or t-butoxycarbonyl, or $R_6$ and $R_7$ are bonded together to form a morpholino or methylpiperazinyl group.

10. The compound or the pharmaceutically acceptable salt thereof according to claim 1, wherein the compound is selected from the group consisting of:
1) 4-Ethoxy-N-(3-fluoro-4-{[2-(5-{[(2-methoxyethyl)amino]methyl}pyridin-2-yl)thieno[3,2-b]pyridin-7-yl]oxy}phenyl)-2-oxo-1-phenyl-1,2-dihydropyridine-3-carboxamide;
2) N-(3-fluoro-4-{[2-(5-{[(2-methoxyethyl)amino]methyl}pyridin-2-yl)thieno[3,2-b]pyridin-7-yl]oxy}phenyl)-1-(4-fluorophenyl)-4-methoxy-2-oxo-1,2-dihydropyridine-3-carboxamide;
3) N-(3-fluoro-4-{[2-(5-{[(2-methoxyethyl)amino]methyl}pyridin-2-yl)thieno[3,2-b]pyridin-7-yl]oxy}phenyl)-4-methoxy-2-oxo-1-phenyl-1,2-dihydropyridine-3-carboxamide;
4) N-(3-fluoro-4-{[2-(5-{[(2-methoxyethyl)amino]methyl}pyridin-2-yl)thieno[3,2-b]pyridin-7-yl]oxy}phenyl)-1-(4-fluorophenyl)-2-oxo-1,2-dihydropyridine-3-carboxamide;
5) N-(3-fluoro-4-{[2-(5-{[(2-methoxyethyl)amino]methyl}pyridin-2-yl)thieno[3,2-b]pyridin-7-yl]oxy}phenyl)-2-oxo-1-phenyl-1,2-dihydropyridine-3-carboxamide;
6) t-Butyl {[6-(7-{4-[4-ethoxy-1-(4-fluorophenyl)-2-oxo-1,2-dihydropyridine-3-carboxamido]-2-fluorophenoxy}thieno[3,2-b]pyridin-2-yl)pyridin-3-yl]methyl}(2-methoxyethyl)carbamate;

7) 4-ethoxy-N-(3-fluoro-4-{[2-(5-{[(2-methoxyethyl)amino]methyl}pyridin-2-yl)thieno[3,2-b]pyridin-7-yl]oxy}phenyl)-1-(4-fluorophenyl)-2-oxo-1,2-dihydropyridine-3-carboxamide;

8) 1-(4-chlorophenyl)-4-ethoxy-N-(3-fluoro-4-{[2-(5-{[(2-methoxyethyl)amino]methyl}pyridin-2-yl)thieno[3,2-b]pyridin-7-yl]oxy}phenyl)-2-oxo-1,2-dihydropyridine-3-carboxamide;

9) N-(3-chloro-4-{[2-(5-{[(2-methoxyethyl)amino]methyl}pyridin-2-yl)thieno[3,2-b]pyridin-7-yl]oxy}phenyl)-1-(4-fluorophenyl)-4-methoxy-2-oxo-1,2-dihydropyridine-3-carboxamide;

10) N-(2-chloro-4-{[-2-(5-{[(2-methoxyethyl)amino]methyl}pyridin-2-yl)thieno[3,2-b]pyridin-7-yl]oxy}phenyl)-1-(4-fluorophenyl)-4-methoxy-2-oxo-1,2-dihydropyridine-3-carboxamide;

11) 1-(4-fluorophenyl)-4-methoxy-N-(4-{[2-(5-{[(2-methoxyethyl)amino]methyl}pyridin-2-yl)thieno[3,2-b]pyridin-7-yl]oxy)phenyl)-2-oxo-1,2-dihydropyridine-3-carboxamide;

12) 4-ethoxy-N-(3-fluoro-4-{[2-(5-{[(2-methoxyethyl)amino]methyl}pyridin-2-yl)thieno[3,2-b]pyridin-7-yl]oxy}phenyl)-2-oxo-1-(4-(trifluoromethyl)phenyl)-1,2-dihydropyridine-3-carboxamide;

13) 1-(4-chlorophenyl)-N-(3-fluoro-4-{[2-(5-{[(2-methoxyethyl)amino]methyl}pyridin-2-yl)thieno[3,2-b]pyridin-7-yl]oxy}phenyl)-4-methoxy-2-oxo-1,2-dihydropyridine-3-carboxamide;

14) 4-ethoxy-N-(3-fluoro-4-{[2-(5-{[(2-methoxyethyl)amino]methyl}pyridin-2-yl)thieno[3,2-b]pyridin-7-yl]oxy}phenyl)-1-(3-fluorophenyl)-2-oxo-1,2-dihydropyridine-3-carboxamide;

15) 4-ethoxy-N-(3-fluoro-4-{[2-(5-{[(2-methoxyethyl)amino]methyl}pyridin-2-yl)thieno[3,2-b]pyridin-7-yl]oxy}phenyl)-1-(4-methoxyphenyl)-2-oxo-1,2-dihydropyridine-3-carboxamide;

16) 4-ethoxy-N-(3-fluoro-4-{[2-(5-{[(2-methoxyethyl)amino]methyl}pyridin-2-yl)thieno[3,2-b]pyridin-7-yl]oxy}phenyl)-1-(3-methoxyphenyl)-2-oxo-1,2-dihydropyridine-3-carboxamide;

17) N-(3-fluoro-4-{[2-(5-{[(2-methoxyethyl)amino]methyl}pyridin-2-yl)thieno[3,2-b]pyridin-7-yl]oxy}phenyl)-2-(4-fluorophenyl)-5-methyl-3-oxo-2,3-dihydropyridazine-4-carboxamide;

18) N-(3-fluoro-4-{[2-(5-{[(2-methoxyethyl)amino]methyl}pyridin-2-yl)thieno[3,2-b]pyridin-7-yl]oxy}phenyl)-5-methyl-3-oxo-2-phenyl-2,3-dihydropyridazine-4-carboxamide;

19) N-(3-fluoro-4-{[2-(5-{[(2-methoxyethyl)amino]methyl}pyridin-2-yl)thieno[3,2-b]pyridin-7-yl]oxy}phenyl)-3-oxo-2-phenyl-2,3-dihydropyridazine-4-carboxamide;

20) N-(3-fluoro-4-[{2-(5-[{(2-methoxyethyl)amino}methyl]pyridin-2-yl)thieno[3,2-b]pyridin-7-yl}oxy]phenyl)-2-(4-fluorophenyl)-3-oxo-2,3-dihydropyridazine-4-carboxamide;

21) N-(3-fluoro-4-{[2-(5-{[(2-methoxyethyl)amino]methyl}pyridin-2-yl)thieno[3,2-b]pyridin-7-yl]oxy}phenyl)-6-methyl-2-oxo-1-phenyl-1,2-dihydropyridine-3-carboxamide;

22) N-(3-fluoro-4-{[2-(5-{[(2-methoxyethyl)amino]methyl}pyridin-2-yl)thieno[3,2-b]pyridin-7-yl]oxy}phenyl)-1-(4-fluorophenyl)-6-methyl-2-oxo-1,2-dihydropyridine-3-carboxamide;

23) 5-Bromo-N-(3-fluoro-4-{[2-(5-{[(2-methoxyethyl)amino]methyl}pyridin-2-yl)thieno[3,2-b]pyridin-7-yl]oxy}phenyl)-1-(4-fluorophenyl)-2-oxo-1,2-dihydropyridine-3-carboxamide;

24) 5-Chloro-N-(3-fluoro-4-{[2-(5-{[(2-methoxyethyl)amino]methyl}pyridin-2-yl)thieno[3,2-b]pyridin-7-yl]oxy}phenyl)-1-(4-fluorophenyl)-2-oxo-1,2-dihydropyridine-3-carboxamide;

25) N-(3-fluoro-4-{[2-(5-{[(2-methoxyethyl)amino]methyl}pyridin-2-yl)thieno[3,2-b]pyridin-7-yl]oxy}phenyl)-1-(4-fluorophenyl)-4-methyl-2-oxo-1,2-dihydropyridine-3-carboxamide;

26) N-(2-chloro-4-{[2-(5-{[(2-methoxyethyl)amino]methyl}pyridin-2-yl)thieno[3,2-b]pyridin-7-yl]oxy}phenyl)-4-ethoxy-1-(4-fluorophenyl)-2-oxo-1,2-dihydropyridine-3-carboxamide;

27) N-(3-fluoro-4-([2-(5-{[(2-methoxyethyl)amino)methyl]pyridin-2-yl}thieno[3,2-b]pyridin-7-yl)oxy]phenyl}-1-(4-fluorophenyl)-5,6-dimethyl-2-oxo-1,2-dihydropyridine-3-carboxamide;

28) N-(3-fluoro-4-{[-2-(5-{[(2-methoxyethyl)amino]methyl}pyridin-2-yl)thieno[3,2-b]pyridin-7-yl]oxy}phenyl)-4-methyl-2-oxo-1-phenyl-1,2-dihydropyridine-3-carboxamide;

29) N-(3-fluoro-4-{[-2-(5-{[(2-methoxyethyl)amino]methyl}pyridin-2-yl)thieno[3,2-b]pyridin-7-yl]oxy}phenyl)-1-(4-fluorophenyl)-5-methyl-2-oxo-1,2-dihydropyridine-3-carboxamide;

30) 4-Ethoxy-N-(3-fluoro-4-{[2-(5-{[(2-methoxyethyl)(methyl)amino]methyl}pyridin-2-yl)thieno[3,2-b]pyridin-7-yl]oxy}phenyl)-1-(4-fluorophenyl)-2-oxo-1,2-dihydropyridine-3-carboxamide;

31) 4-ethoxy-N-[3-fluoro-4-({2-[5-(morpholinomethyl)pyridin-2-yl]thieno[3,2-b]pyridin-7-yl}oxy)phenyl]-1-(4-fluorophenyl)-2-oxo-1,2-dihydropyridine-3-carboxamide;

32) 4-ethoxy-N-[3-fluoro-4-({2-[5-(morpholinomethyl)pyridin-2-yl]thieno[3,2-b]pyridin-7-yl}oxy)phenyl]-2-oxo-1-phenyl-1,2-dihydropyridine-3-carboxamide;

33) 4-ethoxy-N-{3-fluoro-4-[(2-{5-[(4-methylpiperazin-1-yl)methyl]pyridin-2-yl}thieno[3,2-b]pyridin-7-yl)oxy]phenyl}-1-(4-fluorophenyl)-2-oxo-1,2-dihydropyridine-3-carboxamide;

34) 4-ethoxy-N-{3-fluoro-4-[(2-{5-[(-methylpiperazin-1-yl)methyl]pyridin-2-yl}thieno[3,2-b]pyridin-7-yl)oxy]phenyl}-2-oxo-1-phenyl-1,2-dihydropyridine-3-carboxamide;

35) 1-(4-chlorophenyl)-4-ethoxy-N-[3-fluoro-4-({2-[5-(morpholinomethyl)pyridin-2-yl]thieno[3,2-b]pyridin-7-yl}oxy)phenyl]-2-oxo-1,2-dihydropyridine-3-carboxamide;

36) N-[3-chloro-4-({2-[5-(morpholinomethyl)pyridin-2-yl]thieno[3,2-b]pyridin-7-yl}oxy)phenyl]-4-ethoxy-1-(4-fluorophenyl)-2-oxo-1,2-dihydropyridine-3-carboxamide; and 37) N-[2-chloro-4-({2-[5-(morpholinomethyl)pyridin-2-yl]thieno[3,2-b]pyridin-7-yl}oxy)phenyl]-4-ethoxy-1-(4-fluorophenyl)-2-oxo-1,2-dihydropyridine-3-carboxamide.

11. A pharmaceutical composition comprising the compound or the pharmaceutically acceptable salt thereof according claim 1, and a pharmaceutically acceptable additive.

12. A method for inhibiting the activity of a protein kinase in a subject in need thereof, which comprises administering the compound or the pharmaceutically acceptable salt thereof according to claim 1 to the subject, wherein the protein kinase is RON tyrosine kinase.

13. A pharmaceutical composition comprising the compound or the pharmaceutically acceptable salt thereof according to claim 10, and a pharmaceutically acceptable additive.

14. A method of treating a cancer in a subject in need thereof, comprising administering the compound or the pharmaceutically acceptable salt thereof according to claim 10 to the subject, wherein the cancer is a colon cancer.

15. A method for inhibiting the activity of a protein kinase in a subject in need thereof, which comprises administering the compound or the pharmaceutically acceptable salt thereof according to claim 10 to the subject, wherein the protein kinase is RON tyrosine kinase.

* * * * *